US008153126B2

(12) United States Patent
Violette et al.

(10) Patent No.: US 8,153,126 B2
(45) Date of Patent: *Apr. 10, 2012

(54) ANTI-$\alpha_v\beta_6$ ANTIBODIES

(76) Inventors: Shelia M. Violette, Lexington, MA (US); Paul H. Weinreb, Andover, MA (US); Kenneth J. Simon, Cambridge, MA (US); Dean Sheppard, Oakland, CA (US); Diane R. Leone, Winchester, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/260,510

(22) Filed: Oct. 29, 2008

(65) Prior Publication Data

US 2009/0186036 A1 Jul. 23, 2009

Related U.S. Application Data

(62) Division of application No. 10/507,662, filed as application No. PCT/US03/08048 on Mar. 13, 2003, now Pat. No. 7,465,449.

(60) Provisional application No. 60/364,991, filed on Mar. 13, 2002, provisional application No. 60/426,286, filed on Nov. 13, 2002.

(51) Int. Cl.
A61K 39/395 (2006.01)
(52) U.S. Cl. .................. 424/133.1; 424/143.1
(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 5,019,368 A | 5/1991 | Epstein et al. | |
| 5,565,332 A | 10/1996 | Hoogenboom et al. | |
| 5,733,743 A | 3/1998 | Johnson et al. | |
| 5,789,650 A | 8/1998 | Lonberg et al. | |
| 5,827,690 A | 10/1998 | Meade et al. | |
| 6,075,181 A | 6/2000 | Kucherlapati et al. | |
| 6,150,584 A | 11/2000 | Kucherlapati et al. | |
| 6,162,963 A | 12/2000 | Kucherlapati et al. | |
| 6,180,370 B1 | 1/2001 | Queen et al. | |
| 6,291,650 B1 | 9/2001 | Winter et al. | |
| 6,300,064 B1 | 10/2001 | Knappik et al. | |
| 6,303,313 B1 | 10/2001 | Wigler et al. | |
| 6,307,026 B1 | 10/2001 | King et al. | |
| 6,358,710 B1 | 3/2002 | Graves et al. | |
| 6,692,741 B2 | 2/2004 | Huang et al. | |
| 7,544,358 B2 * | 6/2009 | Huang et al. | 424/155.1 |
| 2001/0056076 A1 | 12/2001 | Huang et al. | |

FOREIGN PATENT DOCUMENTS

| | | |
|---|---|---|
| EP | 239400 | 9/1987 |
| EP | 0719859 A1 | 7/1996 |
| EP | 843961 | 5/1998 |
| WO | 90/07861 | 7/1990 |
| WO | 99/07405 | 2/1999 |
| WO | 99/37683 | 7/1999 |

OTHER PUBLICATIONS

Ghannad F, Nica D, Fulle Mig, et al. Absence of avh6 integrin is linked to initiation and progression of periodontal disease. International Association for Dental Research, IADR, Abstract 85, Jul. 1-5, 2008.*
Horan et al. Partial inhibition of integrin alpha(v)beta6 prevents pulmonary fibrosis without exacerbating inflammation. Am J Respir Crit Care Med. Jan. 1, 2008;177(1):56-65.*
Puthawala et al. Inhibition of integrin alpha(v)beta6, an activator of latent transforming growth factor-beta, prevents radiation-induced lung fibrosis. Am J Respir Crit Care Med. Jan. 1, 2008;177(1):82-90.*
Neurohr et al., Activation of Transforming Growth Factor-beta by the Integrin alphaVbeta8 Delays Epithelial Wound Closure. Am J Respir Cell Mol Biol vol. 35. pp. 252-259, 2006.*
Sheppard, D. Integrin-Mediated Activation of Transforming Growth Factor-β1 in Pulmonary Fibrosis. Chest 2001;120;S49-S53.*
Huang et al., J. Cell Sci., 111(Pt 15):2189-2195 (1998).
Mitjans et al., J. Cell Sci., 108(Pt 8):2825-2838 (1995).
Rudikoff et al., Proc. Natl. Acad. Sci. USA, 79(6):1979-1983 (1982).
Weinreb et al., J. Biol. Chem., 279(17):17875-17887 (2004).
Wu et al., Proc. Natl. Acad. Sci. USA, 95(11):6037-6042 (1998).
Munger et al., Cell, 96(3):319-328 (1999).
Ludbrook et al., Biochem. J., 369(Pt 2):311-318 (2003).
Sheppard et al., J. Biol. Chem., 265(20):11502-11507 (1990).
Pittet et al., J Clin. Invest., 107(12):1537-1544 (2001).
Franko et al., Radiat. Res., 140(3):347-355 (1994).
Cosgrove et al., Am. J. Pathol., 157(5):1649-1659 (2000).
Ziyadeh et al., Proc. Natl. Acad. Sci. USA, 97(14):8015-8020 (2000).
Ma, LJ. et al., Lab Investigation, 81:189A (2001).
Ma LJ. et al., J. Am. Soc. Nephrol., 12:819A (2001).
Oft et al., Curr. Biol., 8(23):1243-1252 (1998).
Akhurst et al., Trends Cell Biol., 11(11):544-551 (2001).
Huang et al., J. Cell Biol., 133(4):921-928 (1996).
Huang et al., Am. J. Respir. Cell Mol. Biol., 13(2):245-251 (1995).
Abe et al., Anal. Biochem., 216(2):276-284 (1994).
Thomas et al., J. Invest. Dermatol., 117(1):67-73 (2001).
Brunton et al., Neoplasia, 3(3):215-226 (2001).
Agrez et al., Int. J. Cancer, 81(1)90-97 (1999).
Breuss et al., J. Cell Sci., 108(Pt 6):2241-2251 (1995).
Ma et al., Kidney Int., 53(4):937-944 (1998).
George et al., Proc. Natl. Acad. Sci. USA, 96(22):12719-12724 (1999).
George et al., Am. J. Pathol., 156(1):115-124 (2000).
Kunicki et al., J. Biol. Chem., 272(7):4103-4107 (1997).
Kunicki et al., J. Biol. Chem., 270(28):16660-16665 (1995).
Sheppard, Physiol. Rev., 83(3):673-686 (2003).
Knight et al., Am. J. Pathol., 161(3):771-779 (2002).
Sheppard, Chest, 120(1 Suppl):49S-53S (2001).
Kaminski et al., Proc. Natl. Acad. Sci. USA, 97(4):1778-1783 (2000).
Huang et al., Am. J. Respir. Cell Mol. Biol., 19(4):636-642 (1998).
Sheppard, Am. J. Respir. Cell Mol. Biol., 19(3):349-351 (1998).

(Continued)

*Primary Examiner* — Maher Haddad
(74) *Attorney, Agent, or Firm* — McAndrews, Held & Malloy Ltd.

(57) ABSTRACT

Monoclonal antibodies that specifically bind to □v□□. Also included are methods of using these antibodies to treat mammals having or at risk of having □v□6-mediated diseases, or to diagnose □V□6-mediated diseases.

16 Claims, 25 Drawing Sheets

OTHER PUBLICATIONS

Dixit et al., J. Biol. Chem., 271(42):25976-25980 (1996).
Weinacker et al., J. Biol. Chem., 269(9):6940-6948 (1994).
Agrez et al., J. Cell Biol., 127(2):547-556 (1994).
Busk et al., J. Biol. Chem., 267(9):5790-5796 (1992).
Palmer et al., Chest, 69:307-309 (1976).
Tsushima et al., Inter. Med., 48:621-630 (2009).
PLoS Medicine, Apr. 2006, vol. 3, Issue 4, p. 0420.
Xue et al., "Role of the αvβ6 Integrin in Human Oral Squamous Cell Carcinoma Growth in Vivo in Vitro." Biochemical and Biophysical Research Communications 288, 610-618, 2001.
European Patent Office, Communication Pursuant to Article 94(3) EPC, in EP application No. 03 755 325.2, dated Mar. 26, 2010 (5 pages).
Office Action in CA 2,478,833, dated Sep. 27, 2010.
Extended European Search Report in EP 10012545.9, dated Apr. 29, 2011.
Extended European Search Report in EP 10013155.6, dated Apr. 28, 2011.
Leone et al., "A blocking monoclonal antibody to integrin alphavbeta6 inhibits tumor growth in a human pharyngeal xenograft model," Proceedings of the Annual Meeting of the American Association for Cancer Research, vol. 44 (2003) XP008070338.
Office Action in KR 10-2004-7014307, dated Jun. 29, 2011.

* cited by examiner

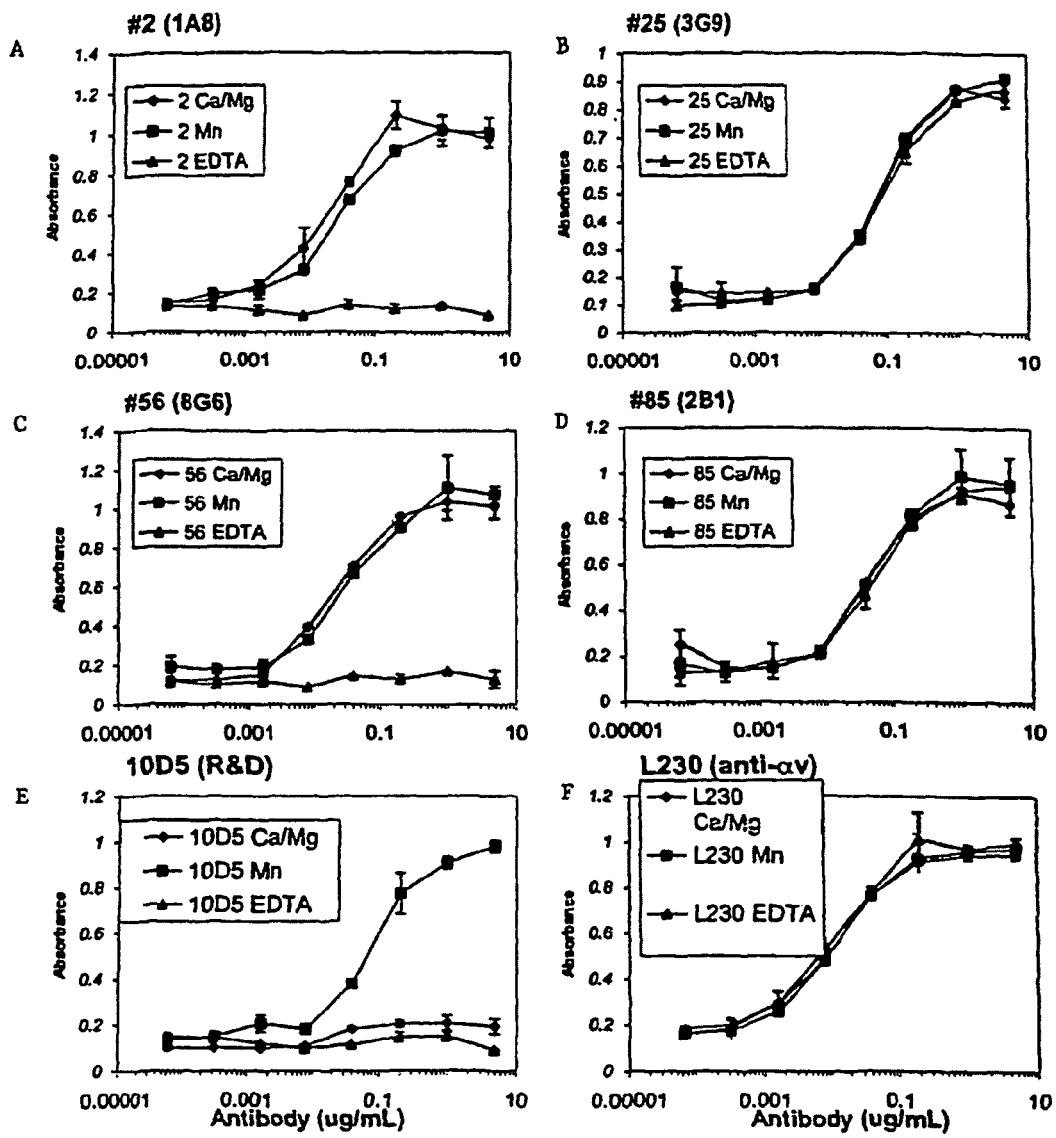
FIGS. 3 A-F
Cation-Dependence of Binding to Soluble αvβ6

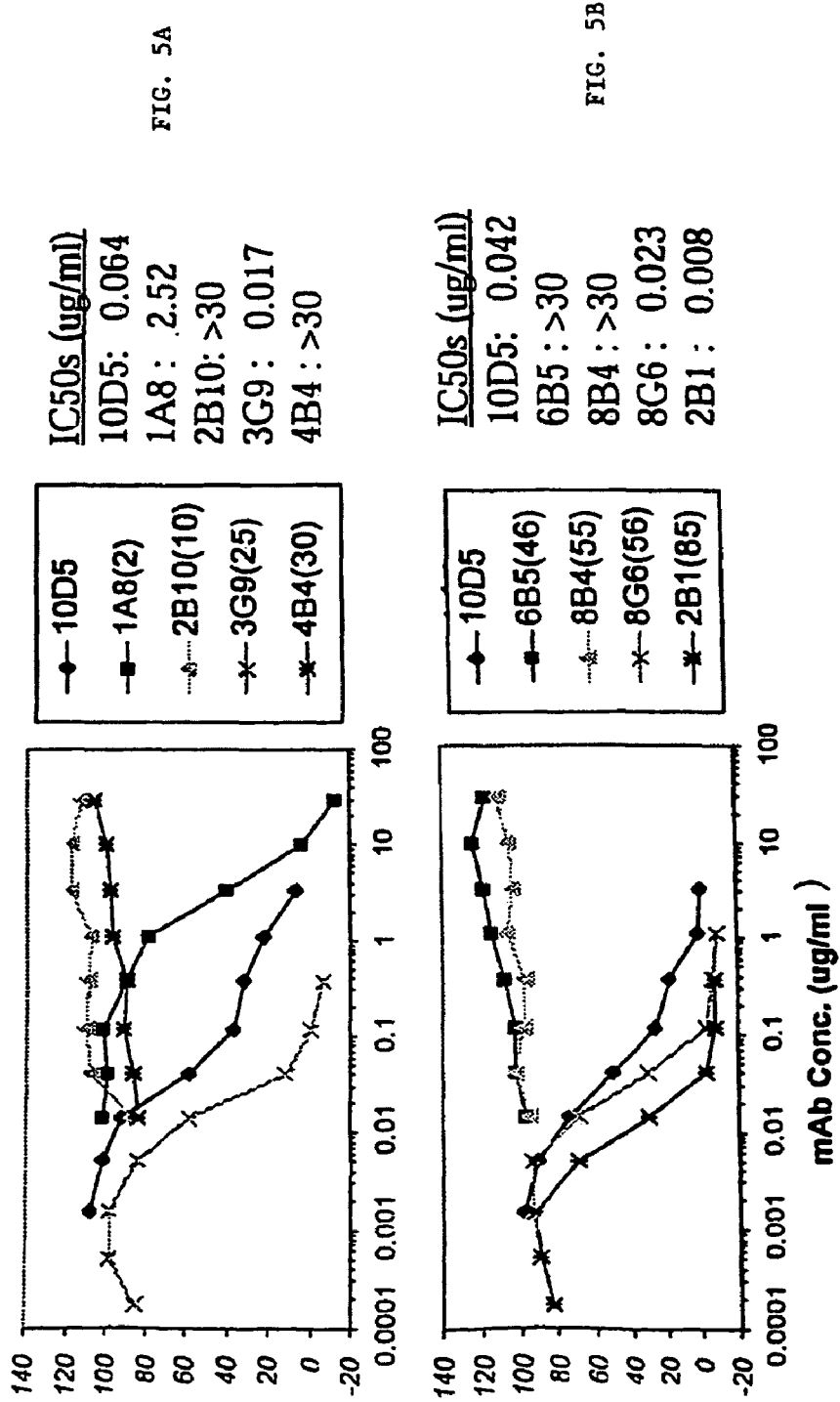

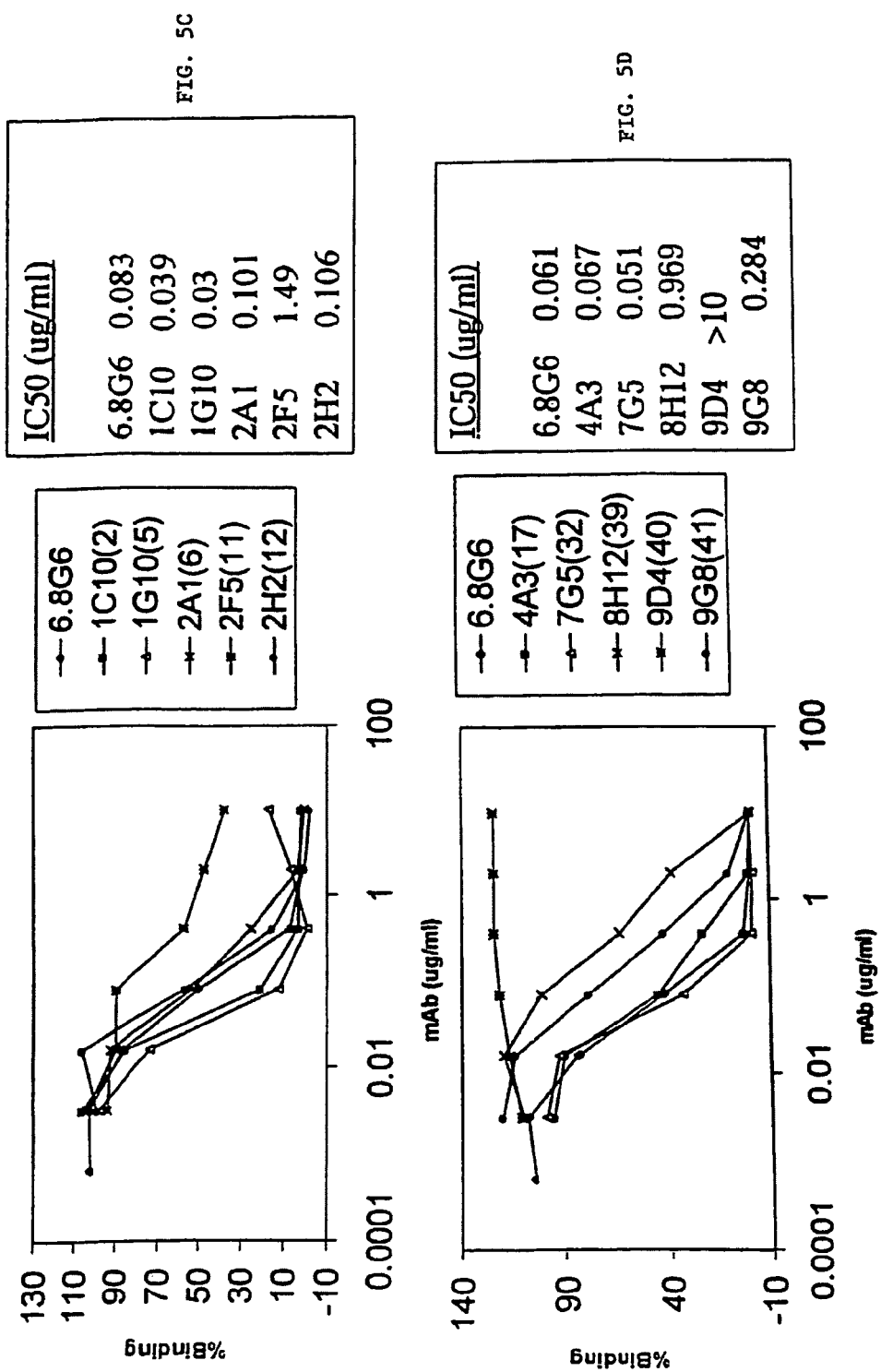

FIG. 7A

```
6.1A8   (1)  DIVLTQSPASLAVSLGQRATIS CRASQSVSIST-YSY IHWFQQKPGQPPKL IKYASN LESGVPARFSGSGSGTDFTLNIHPVEEEDTAIYYC
6.8G6   (1)  DIVLTQSPASLAVSLGQRAIIS CRASQSVSTSS-YSY MYWYQQKPGQSKPF LIKYASN LESGVPARFSGSGSGTDFTLNIHPVEEEDTATYYC
6.4B4   (1)  DVVMTQTPRSLPVSLGDQASMS CRSSQSLKHSNGDTY LHWYLQKPGQSPNL LIYKVSN RFSGVPDRFSGSGSGTEFTFKISRVEAEDLGVYFC
6.2A1   (1)  DIVMTQSHKFMSTSVGDRVSIT CKASLDVR------TA VAWYQQKPGQSPKL LIYSASY PYTGVPDRFTGSGSGTDFTFTNIRSVQAEDLAVYYC
6.2G2   (1)  DIVMTQSHKFMSTSVGDRVSVT CKASQAVN------TA VAWYQQKPGQSPKL LIYSASY QYTGVPDRFTGSGSGTDFTLTISSVQAEDLAVYYC
7.1C5   (1)  DIQMTQSPSSLSASLGERVNLT CRASQEISG-----YL SWLQQKPDGTIKR LIYAAST LDSGVPKRFSGSRSGSDYSLTISSLESEDFGDYYC
7.1G10  (1)  DIQMTQSPSSLSASLGERVSLT CRASQEISG-----YL SWLQQKPDGSIKR LIYAAST LDSGVPKRFSGSRSGADYSLTISSLBSEDFADYYC
6.2B10  (1)  QIVLTQSPAIMSASPGEKVTMT CSASSSVS------YM MHWYQQKSGTSPRR WIYDTSK LASGVPTRFSGSGSGTSYSLTINSMEAVDAATYYC
7.7G5   (1)  QIVLTQSPAIMSASPGEKVTMT CSASSSVS------YM MHWYQQKSGTSPKR WIYDTSK LASGVPTRFSGSGSGTSYSLTINSMEAEDAATYYC
6.2B1   (1)  QIVLTQSPAIMSASPGEKVTLT CSASSSVSS-----YL YWYQQKPGSSPKL WIYSTSN LASRVPARFSGSGSGTSYSLTISSMEAEDAASYFC
6.3G9   (1)  QIVLTQSPAIMSASPGEKVTLT CSASSSVSSS----YL YWYQQKPGSSSPKL MIYSTSN LASGVPVRFSGSGSGTSFSLTISSMEAEDAASYFC 6.1A8   (93) QHSWEIPYT FGGGTKVEIK    SEQ ID NO:37
6.8G6   (93) QHNWEIPFT FGGGTKLBIK    SEQ ID NO:38
6.4B4   (94) SQSTHVPYT FGGGTRLBIK    SEQ ID NO:39
6.2A1   (89) QQHYGIPWT FGGGTKLBIK    SEQ ID NO:63
6.2G2   (89) QHYGVPWT  FGGGTKLBIK    SEQ ID NO:64
7.1C5   (89) LQYASYPYT FGGGAKLBIK    SEQ ID NO:40
7.1G10  (89) LQYATYPYT FGGGTKLGIK    SEQ ID NO:41
6.2B10  (88) QQWTSNPFT FGSGTKLBLK    SEQ ID NO:42
7.7G5   (88) QQWSSHPPT FGAGTKLBLK    SEQ ID NO:43
6.2B1   (90) HQWSSYPPT FGGGTKLBIK    SEQ ID NO:44
6.3G9   (90) HQWSTYPPT FGGGTKLBIK    SEQ ID NO:45
```

FIG. 7B

Response of the subcutaneously implanted Detroit 562, human pharynx carcinoma cell Line to avß6 mAb therapy with 3G9.

Response of the subcutaneously implanted Detroit 562, human pharynx carcinoma cell Line to avß6 mAb therapy with 4B4.

ANTI-$\alpha_v\beta_6$ ANTIBODIES

This application is a divisional of U.S. Application No. 10/507,662 (now U.S. Pat. No. 7,465,449), which was filed on May. 20, 2005, as a U.S. National Phase application of PCT/US03/08048, which was filed on Mar. 13, 2003, claiming the benefit of priority of U.S. Provisional Application No. 60/364,991, which was filed Mar. 13, 2002 and U.S. Provisional Application No. 60/426,286, which was filed Nov. 13, 2002.

FIELD OF THE INVENTION

This invention relates generally to the field of molecular biology and specifically to antibodies to $\alpha_v\beta_6$ integrins.

This patent application contains material that is subject of a joint research agreement between THE REGENTS OF THE UNIVERSITY OF CALIFORNIA and to BIOGEN IDEC MA Inc.

BACKGROUND OF THE INVENTION

Integrins are a superfamily of cell surface receptors that mediate cell-cell and cell-matrix adhesion. These proteins are known to provide anchorage as well as signals for cellular growth, migration and differentiation during development and tissue repair. Integrins have also been implicated in cell dedifferentiation and invasion, notably where cells lose their specialized form and become metastasizing cancer cells.

Integrins are heterodimeric proteins composed of two non-covalently linked subunits, $\alpha$ and $\beta$. The binding specificity of integrins is dictated by the combination of some 18 different $\alpha$ chains with some 8 different $\beta$ chains. The $\alpha_v\beta_6$ integrin can bind to a number of ligands including fibronectin, tenascin, vitronectin, and the recently identified latency associated peptide "LAP," a 278 amino acid peptide synthesized as part of the precursor TGF-$\beta$ protein (Munger et al., Cell 96(3): 319-328 (1999)). LAP is cleaved from the mature form of TGF-$\beta$ as an N-terminal peptide during secretion but remains noncovalently associated with TGF-$\beta$ to maintain its latent state. This complex cannot bind to the TGF-$\beta$ receptor and hence is not biologically active. The $\alpha_v\beta_6$ integrin can bind directly to an RGD motif contained within LAP, resulting in release of LAP and activation of TGF-$\beta$. Since $\alpha_v\beta_6$'s binding to LAP may be important in the conversion of TGF-$\beta$ to its active state, blocking the binding may result in inhibition of $\alpha_v\beta_6$-mediated activation of TGF-$\beta$ and the associated fibrotic pathology.

SUMMARY OF THE INVENTION

This invention is based on the discovery and characterization of high affinity antibodies against $\alpha_v\beta_6$, including the identification and analysis of key amino acid residues in the complementary determining regions (CDRs) of such antibodies.

This invention embraces a monoclonal antibody that (a) specifically binds to $\alpha_v\beta_6$; (b) inhibits the binding of $\alpha_v\beta_6$ to its ligand such as LAP, fibronectin, vitronectin, and tenascin with an $IC_{50}$ value lower than that of 10D5 (International Patent Application Publication WO 99/07405); (c) blocks activation of TGF-$\beta$; (d) contains certain amino acid sequences in the CDRs (e.g., those shown in FIGS. 7A and 7B) that provide binding specificity to $\alpha_v\beta_6$; (e) specifically binds to the $\beta_6$ subunit; and/or (f) recognizes $\alpha_v\beta_6$ in immunostaining procedures, such as immunostaining of paraffin-embedded tissues.

It has been discovered that antibodies that bind to $\alpha_v\beta_6$ can be grouped into biophysically distinct classes and subclasses. One class of antibodies exhibits the ability to block binding of a ligand (e.g., LAP) to $\alpha_v\beta_6$ (blockers). This class of antibodies can be further divided into subclasses of cation-dependent blockers and cation-independent blockers. Some of the cation-dependent blockers contain an arginine-glycine-aspartate (RGD) peptide sequence, whereas the cation-independent blockers do not contain an RGD sequence. Another class of antibodies exhibits the ability to bind to $\alpha_v\beta_6$ and yet does not block binding of $\alpha_v\beta_6$ to a ligand (nonblockers).

Accordingly, in some embodiments of this invention, some antibodies of this invention are divalent cation-dependent for binding to $\alpha_v\beta_6$, while others are divalent cation-independent. Exemplary cations are $Ca^{2+}$, $Mg^{2+}$ and $Mn^{2+}$.

In some embodiments, the antibody comprises the same heavy and light chain polypeptide sequences as an antibody produced by hybridoma 6.1A8, 6.3G9, 6.8G6, 6.2B1, 6.2B10, 6.2A1, 6.2E5, 7.1G10, 7.7G5, or 7.1C5.

In some embodiments, the antibodies comprise a heavy chain whose complementarity determining regions (CDR) 1, 2 and 3 consist essentially (i.e., with the exception of some conservative variations) of the sequences of SEQ ID Nos:1, 4 and 7, respectively, and/or a light chain whose CDRs 1, 2 and 3 consist essentially of the sequences of SEQ ID NOs:10, 13 and 15, respectively.

In some embodiments, the antibodies comprise a heavy chain whose CDRs 1, 2 and 3 consist essentially of the sequences of SEQ ID NOs:3, 5 and 8, respectively, and/or a light chain whose CDRs 1, 2 and 3 consist essentially of the sequences of SEQ ID NOs:11, 14 and 17, respectively.

In some embodiments, the antibodies comprise a heavy chain whose CDRs 1, 2 and 3 consist essentially of the sequences of SEQ ID NOs:3, 6 and 9, respectively, and/or a light chain whose CDRs 1, 2 and 3 consist essentially of the sequences of SEQ ID NOs:12, 14 and 18, respectively.

In some embodiments, the antibodies comprise a heavy chain whose CDRs 1, 2 and 3 consist essentially of the sequences of SEQ ID NOs:2, 46 and 47, respectively, and/or a light chain whose CDRs 1, 2 and 3 consist essentially of the sequences of SEQ ID NOs:48, 13 and 16, respectively.

In some embodiments, the antibodies comprise a heavy chain whose CDRs 1, 2 and 3 consist essentially of the sequences of SEQ ID NOs:49, 51 and 53, respectively, and/or a light chain whose CDRs 1, 2 and 3 consist essentially of the sequences of SEQ ID NOs:55, 57 and 59, respectively.

In some embodiments, the antibodies comprise a heavy chain whose CDRs 1, 2 and 3 consist essentially of the sequences of SEQ ID NOs:50, 52 and 54, respectively, and/or a light chain whose CDRs 1, 2 and 3 consist essentially of the sequences of SEQ ID NOs:56, 58 and 60, respectively.

In some embodiments, the antibodies comprise a heavy chain variable domain sequence of any one of SEQ ID NOs: 19-36 and 61-62.

In some embodiments, the antibodies comprise heavy and light chain variable domain sequences of
(1) SEQ ID NOs:19 and 37;
(2) SEQ ID NO:20 or 21, and SEQ ID NO:38;
(3) SEQ ID NOs:22 and 43;
(4) SEQ ID NOs:23 and 44;
(5) SEQ ID NOs:24 and 45;
(6) SEQ ID NO:25 or 26 and SEQ ID NO:42;
(7) SEQ ID NO:27, 28, or 29, and SEQ ID NO:39;
(8) SEQ ID NO:34 or 35, and SEQ ID NO:40;
(9) SEQ ID NOs:36 and 41;

(10) SEQ ID NOs:61 and 63; or
(11) SEQ ID NOs:62 and 64,
respectively.

In some embodiments, the antibodies specifically binds to $\alpha_v\beta_6$ but does not inhibit the binding of $\alpha_v\beta_6$ to latency associated peptide (LAP). At least some of these antibodies are capable of binding to $\alpha_v\beta_6$ in paraffin-embedded tissue sections and therefore can be used for diagnostic purposes. Exemplary antibodies include 6.2A1 and 6.2E5.

This invention also embraces antibodies that bind to the same epitope as any of the above-described antibodies.

This invention also embraces compositions comprising one or more antibodies of this invention, and a pharmaceutically acceptable carrier. In some of these compositions, the antibodies are conjugated to a cytotoxic agent (i.e., an agent that impairs the viability and/or the functions of a cell) such as a toxin or a radionuclide. The antibodies in these compositions can be cation-dependent antibodies. The compositions can be administered to a subject (e.g., a mammal such as a human) having or at risk of having a disease mediated by $\alpha_v\beta_6$, so as to treat (e.g., alleviating, mitigating, reducing, preventing, postponing the onset of) the disease. Examples of such diseases include, but are not limited to: fibrosis (e.g., scleroderma, scarring, liver fibrosis, lung fibrosis, and kidney fibrosis); psoriasis; cancer (e.g., epithelial cancer; oral, skin, cervical, ovarian, pharyngeal, laryngeal, esophageal, lung, breast, kidney, or colorectal cancer); Alport's Syndrome; acute and chronic injuries of the lung, liver, kidney and other internal organs; and sclerosis of the lung, liver, kidney and other internal organs. Risks of having such diseases may result from genetic predisposition; certain lifestyles such as smoking and alcoholism; exposure to environmental pollutants such as asbestos; physiological conditions such as diabetes, hepatitis viral infection (e.g., hepatitis C viral infection), autoimmune diseases; and medical treatments such as radiation therapy.

This invention also embraces methods of detecting $\alpha_v\beta_6$ in a tissue sample from a mammal (e.g., a human), comprising contacting the tissue sample with the antibody of the invention, such as 6.2A1 and 6.2E5.

This invention also embraces cells of hybridomas 6.1A8, 6.2B10, 6.3G9, 6.8G6, 6.2B1, 6.2A1, 6.2E5, 7.1G10, 7.7G5, and 7.1C5; isolated nucleic acids comprising a coding sequence for any one of SEQ ID NOs:19-45 and 61-64; isolated polypeptides comprising an amino acid sequence of any one of SEQ ID NOs:19-45 and 61-64.

An antibody of this invention refers to a full antibody, e.g., an antibody comprising two heavy chains and two light chains, or to an antigen-binding fragment of a full antibody such as a Fab fragment, a Fab' fragment, a F(ab')$_2$ fragment or a F(v) fragment. An antibody of this invention can be a murine antibody or a homolog thereof, or a fully human antibody. An antibody of this invention can also be a humanized antibody, a chimeric antibody or a single-chained antibody. An antibody of this invention can be of any isotype and subtype, for example, IgA (e.g., IgA1 and IgA2), IgG (e.g., IgG1, IgG2, IgG3 and IgG4), IgE, IgD, IgM, wherein the light chains of the immunoglobulin may be of type kappa or lambda.

In some embodiments, the antibody of the invention may comprise a mutation (e.g., deletion, substitution or addition) at one or more (e.g., 2, 3, 4, 5, or 6) of certain positions in the heavy chain such that the effector function of the antibody (e.g., the ability of the antibody to bind to a Fc receptor or a complement factor) is altered without affecting the antibody's antigen-binding ability. In other embodiments, the antibody of this invention may contain a mutation at an amino acid residue that is a site for glycosylation such that the glycosylation site is eliminated. Such an antibody may have clinically beneficial, reduced effector functions or other undesired functions while retaining its antigen-binding affinity. Mutation of a glycosylation site can also be beneficial for process development (e.g., protein expression and purification). In still other embodiments, the heavy or light chains can contain mutations that increase affinity or potency.

Several of the Fusion #6 and Fusion #7 hybridomas were deposited at the American Type Culture Collection ("ATCC"; P.O. Box 1549, Manassas, Va. 20108, USA) under the Budapest Treaty. Hybridoma clones 6.1A8, 6.2B10, 6.3G9, 6.8G6, and 6.2B1 were deposited on Aug. 16, 2001, and have accession numbers ATCC PTA-3647, -3648, -3649, -3645, and -3646, respectively. Hybridoma clones 6.2A1, 6.2E5, 7.1G10, 7.7G5, and 7.1C5 were deposited on Dec. 5, 2001, and have accession numbers ATCC PTA-3896, -3897, -3898, -3899, and -3900, respectively. See Table 1, infra.

The antibodies of the invention are useful for treating any clinically undesirable condition or disease (as discussed herein) that is mediated by binding of $\alpha_v\beta_6$ to its ligand, such as LAP and fibronectin. These antibodies can be more potent, via higher affinity or avidity, and cation dependency or independency of binding to ligand, than previously known $\alpha_v\beta_6$ antibodies.

In addition to therapeutic applications of the antibodies of the invention, especially the blockers, the nonblocker class of antibodies can be used for diagnostic purposes, such as in antigen capture assays, enzyme-linked immunosorbent assays (ELISAs), immunohistochemistry, and the like.

Other features and advantages of the invention will be apparent from the following detailed description, drawings, and claims.

BRIEF DESCRIPTION OF THE DRAWINGS

FIGS. 3A-F are graphs showing the differential cation dependence of the binding of various anti-$\alpha_v\beta_6$ monoclonal antibodies to hs$\alpha_v\beta_6$.

FIGS. 5A-E are graphs showing that exemplary monoclonal antibodies of the invention inhibit the binding of β6-transfected FDC-P1 cells to LAP. FIGS. 5A and 5B display the results from Fusion #6 antibodies. FIGS. 5C-E display the results from Fusion #7 antibodies.

FIG. 7A depicts the amino acid sequences of the variable domains of the heavy chains of $\alpha_v\beta_6$ monoclonal antibodies 6.1A8, 6.8G6 (subclones A and B), 7.7G5, 6.2B1, 6.3G9, 6.2B10 (subclones A and B), 6.2G2, 6.2A1, 6.4B4 (subclones A, B and C), 7.10H2, 7.9H5, 7.4A3 (subclones A and B), 7.1C5 (subclones A and B) and 7.1G10. Antibodies 6.1A8, 6.8G6 and 7.7G5 are cation-dependent in binding to $\alpha_v\beta_6$, while antibodies 6.2B1, 6.2A1, 6.3G9, 6.2B10, 6.4B4, 7.1C5 and 7.1G10 are cation-independent (infra). The numbers in parentheses denote amino acid residue positions. The CDRs are in the large boxes, while the small boxes containing italicized amino acids represent polymorphism in different clones of a particular antibody.

FIG. 7B depicts the amino acid sequences of the variable domains of the light chains of $\alpha_v\beta_6$ monoclonal antibodies 6.1A8, 6.8G6, 6.4B4, 6.2A1, 7.1C5, 7.1G10, 6.2B10, 7.7G5, 6.2B1 and 6.3G9.

In FIG. 15C, the graph shows hydroxyproline content per lung.

DETAILED DESCRIPTION OF THE INVENTION

Figure 1A:
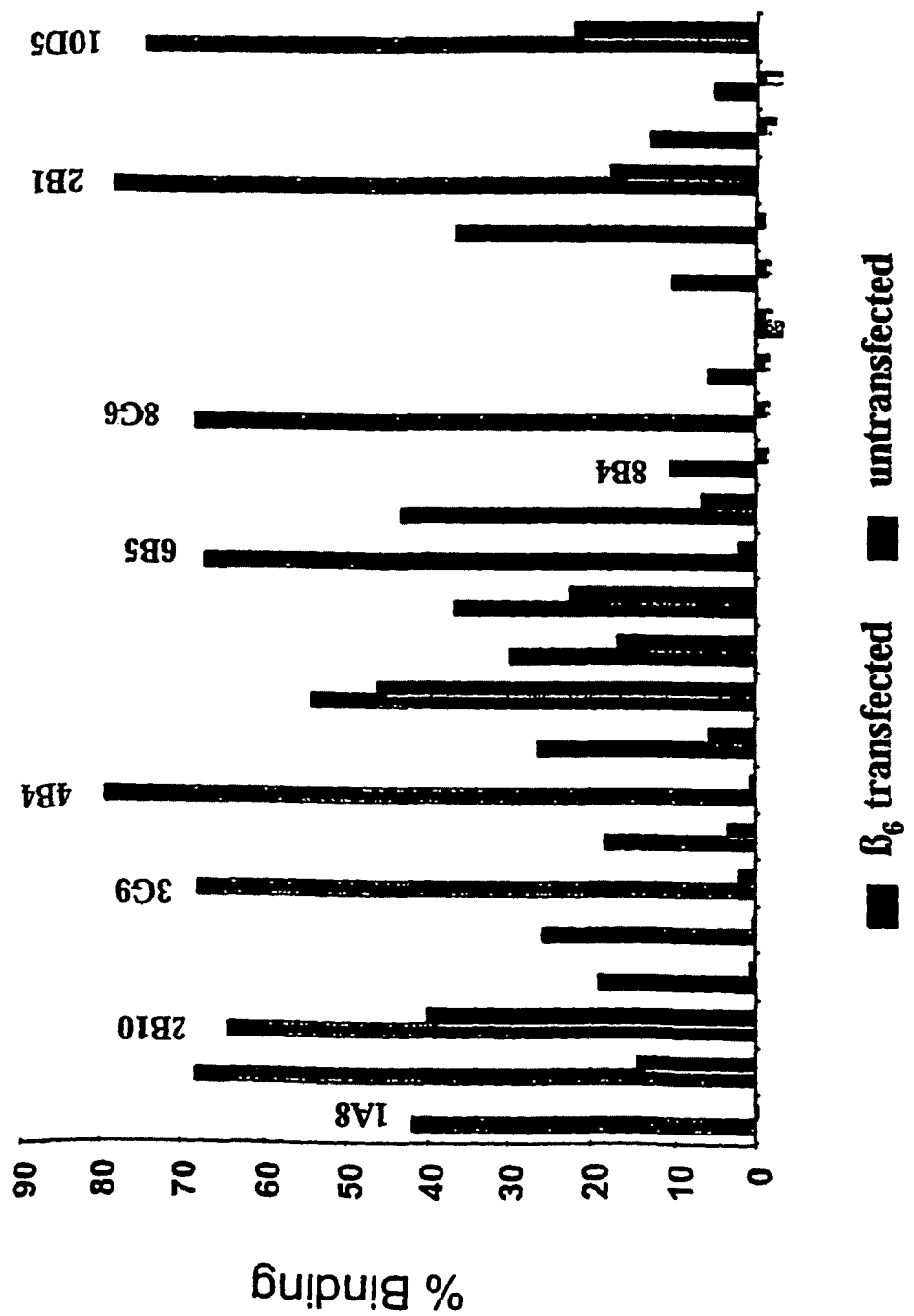
FIGS. 1A and 1B are bar graphs showing the results of a cell capture assay that determined the ability of various anti-$\alpha_v\beta_6$ monoclonal antibodies ("mAb") to bind $\beta_6$-transfected FDC-P1 cells (untransfected cells as control).

This invention features classes and subclasses of antibodies that are specific for the integrin $\alpha_v\beta_6$. At least one class of the antibodies (blockers) are capable of blocking the binding of $\alpha_v\beta_6$ to LAP or preventing the activation of TGF-β.

The following describes the various methods of making the antibodies of this invention. Methods that are known in the art but not specifically described herein are also within the scope of this invention. For instance, antibodies of this invention can also be identified using phage-displayed antibody libraries, such as those described in Smith, Science 228:1315-7 (1985); U.S. Pat. Nos. 5,565,332, 5,733,743, 6,291,650, and 6,303,313. Additional antibodies of this invention can be made by coupling the heavy chains identified herein with a noncognate light chain, e.g., a light chain identified by phage display technology.

Non-Human Hybridoma Antibodies

The monoclonal antibodies of this invention can be generated by well known hybridoma technology. To do so, $\beta_6$−/− animals (e.g., mice, rats or rabbits) are immunized with purified or crude $\alpha_v\beta_6$ preparations, cells transfected with cDNA constructs encoding $\alpha_v\beta_6$ or both antigens, cells that constitutively express $\alpha_v\beta_6$, and the like. The antigen can be delivered as purified protein, protein expressed on cells, protein fragment or peptide thereof, or as naked DNA or viral vectors encoding the protein, protein fragment, or peptide. Sera of the immunized animals are then tested for the presence of anti-$\alpha_v\beta_6$ antibodies. B cells are isolated from animals that test positive, and hybridomas are made with these B cells.

Antibodies secreted by the hybridomas are screened for their ability to bind specifically to $\alpha_v\beta_6$ (e.g., binding to $\beta_6$-transfected cells and not to untransfected parent cells) and for any other desired features, e.g., having the desired CDR consensus sequences, inhibiting (or not inhibiting in the case of nonblockers) the binding between LAP and $\alpha_v\beta_6$ with an $IC_{50}$ value lower than that of known anti-$\alpha_v\beta_6$ antibody 10D5, or inhibiting TGF-β activation.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

Chimeric Antibodies

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art.

The chimeric antibodies embraced in this invention may contain a heavy chain variable domain having a sequence identical (or substantially so) to any one of SEQ ID NOs:19-

36 and/or a light chain variable domain having a sequence identical (or substantially so) to any one of SEQ ID NOs:37-45.

Preferred human constant regions include those derived from IgG1 and IgG4.

Fully Human Antibodies

The monoclonal antibodies of this invention also include fully human antibodies. They may be prepared using in vitro-primed human splenocytes, as described by Boerner et al., *J. Immunol.* 147:86-95 (1991), or using phage-displayed antibody libraries, as described in, e.g., U.S. Pat. No. 6,300,064.

Some other methods for producing fully human antibodies involve the use of non-human animals that have inactivated endogenous Ig loci and are transgenic for un-rearranged human antibody heavy chain and light chain genes. Such transgenic animals can be immunized with $\alpha_v\beta_6$ and hybridomas are then made from B cells derived therefrom. These methods are described in, e.g., the various GenPharm/Medarex (Palo Alto, Calif.) publications/patents concerning transgenic mice containing human Ig miniloci (e.g., Lonberg U.S. Pat. No. 5,789,650); the various Abgenix (Fremont, Calif.) publications/patents with respect to XENOMICE (e.g., Kucherlapati U.S. Pat. Nos. 6,075,181, 6,150,584 and 6,162,963; Green et al., *Nature Genetics* 7:13-21 (1994); and Mendez et al., 15(2):146-56 (1997)); and the various Kirin (Japan) publications/patents concerning "transomic" mice (e.g., EP 843 961, and Tomizuka et al., *Nature Genetics* 16:133-1443 (1997)).

Humanized Antibodies

The monoclonal antibodies of this invention also include humanized versions of cognate anti-$\alpha_v\beta_6$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components.

The methods for making humanized antibodies are described in, e.g., Winter EP 239 400; Jones et al., *Nature* 321:522-525 (1986); Riechmann et al., *Nature* 332:323-327 (1988); Verhoeyen et al., *Science* 239: 1534-1536 (1988); Queen et al., *Proc. Nat. Acad. Sci. USA* 86:10029 (1989); U.S. Pat. No. 6,180,370; and Orlandi et al., *Proc. Natl. Acad. Sci. USA* 86:3833 (1989). Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g., γ1 for CH and k for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., *Proc. Nat. Acad. Sci. USA* 88:2869-2873 (1991), and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the non-human donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, *Biotechnology* 9: 266-271 (1991). Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

Other Moieties

The monoclonal antibodies of this invention may further comprise other moieties to effect the desired functions. For instance, the antibodies may include a toxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026) The antibodies may comprise a moiety (e.g., biotin, fluorescent moieties, radioactive moieties, histidine tag or other peptide tags) for easy isolation or detection. The antibodies may also comprise a moiety that can prolong their serum half life, for example, a polyethylene glycol (PEG) moiety.

Diseased Conditions And Animal Models

The antibodies of the invention are useful in the treatment, including prevention, of $\alpha_v\beta_6$-mediated diseases. For example, these antibodies can be used to treat fibrosis (e.g., lung fibrosis, acute lung injury, kidney fibrosis, liver fibrosis, Alport's Syndrome, and scleroderma) by blocking the activation of TGF-β or blocking the binding of $\alpha_v\beta_6$ to any other ligands, such as fibronectin, vitronectin, and tenascin. The novelty of this approach includes: (1) it blocks the activation of TGF-β rather than the binding of TGF-β to its receptor, (2) it can inhibit TGF-β locally (i.e., at sites of $\alpha_v\beta_6$ upregulation) rather than systemically, and (3) it inhibits binding of $\alpha_v\beta_6$ to a ligand. Other than fibrotic diseases or conditions, the antibodies of the invention are useful in treating cancer or cancer metastasis (including tumor growth and invasion), particularly epithelial cancers. A subset of epithelial cancers is squamous cell carcinoma, e.g., head and neck, oral, breast, lung, prostate, cervical, pharyngeal, colon, pancreatic and ovarian cancers. Our studies using the new $\alpha_v\beta_6$ monoclonal antibodies demonstrated that $\alpha_v\beta_6$ is highly expressed in many epithelial cancers, especially on the leading edge of the tumors. The new antibodies can also be used to any other diseases mediated by $\alpha_v\beta_6$, including psoriasis.

The treatments of this invention are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

The efficacy of the antibodies of the invention can be tested in various animal models. Mouse models for lung fibrosis include bleomycin- (Pittet et al., *J. Clin. Invest.* 107(12): 1537-1544 (2001); and Munger et al., supra) and irradiation-inducible lung fibrosis (Franko et al., *Rad. Res.* 140:347-355 (1994)). In bleomycin-treated mice, the expression of $\alpha_v\beta_6$ increases in the epithelial alveolar cells of the lungs. But $\beta_6$ knockout mice are protected from bleomycin-induced injury and fibrosis.

Mouse models for kidney fibrosis include COL4A3−/− mice (see, e.g., Cosgrove et al., *Amer. J. Path.* 157:1649-1659 (2000), mice with adriamycin-induced injury (Wang et al., *Kidney International* 58: 1797-1804 (2000); Deman et al., *Nephrol Dial Transplant* 16: 147-150 (2001)), db/db mice (Ziyadeh et al., *PNAS USA* 97:8015-8020 (2000)), and mice with unilateral ureteral obstruction (Fogo et al., *Lab Investigation* 81: 189A (2001); and Fogo et al., *Journal of the American Society of Nephrology* 12:819 A (2001)). In all of these models, the mice develop kidney injury and fibrosis that can progress to renal failure. $\alpha_v\beta_6$ is upregulated in the epithelial lining of the ascending and descending tubules of the kidneys of the COL4A3−/− mice, adriamycin-treated mice, and mice that undergo unilateral ureteral obstruction. It is likely that so $\alpha_v\beta_6$ expression also increases in a variety of kidney injury models.

Anti-$\alpha_v\beta_6$ monoclonal antibodies can also be tested for their ability to inhibit tumor growth, progression, and metastasis in such animal models as the standard in vivo tumor growth and metastasis models. See, e.g., Rockwell et al., *J. Natl. Cancer Inst.* 49:735 (1972); Guy et al., *Mol. Cell. Biol.* 12:954 (1992); Wyckoff et al., *Cancer Res.* 60:2504 (2000); and Oft et al., *Curr. Biol.* 8:1243 (1998). Important $\alpha_v\beta_6$ ligands in cancer may include TGF-β, which is involved in, metastasis (for review see Akhurst et al., *Trends in Cell Biology* 11:S44-S51 (2001)), fibronectin and vitronectin.

The efficacy of the treatments of this invention may be measured by a number of available diagnostic tools, including physical examination, blood tests, proteinuria measurements, creatinine levels and creatinine clearance, pulmonary function tests, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

Pharmaceutical Compositions

The pharmaceutical compositions of this invention comprise one or more antibodies of the present invention, or pharmaceutically acceptable derivatives thereof, optionally with any pharmaceutically acceptable carrier. The term "carrier" as used herein includes known acceptable adjuvants and vehicles.

According to this invention, the pharmaceutical compositions may be in the form of a sterile injectable preparation, for example a sterile injectable aqueous or oleaginous suspension. This suspension may be formulated according to techniques known in the art using suitable dispersing, wetting, and suspending agents.

The pharmaceutical compositions of this invention may be given orally, topically, intravenously, subcutaneously, intraperitoneally, intramuscularly, intramedullarily, intra-articularly, intra-synovially, intrasternally, intrathecally, intrahepatically, or intracranially as desired, or just locally at sites of inflammation or tumor growth. The pharmaceutical compositions of this invention may also be administered by inhalation through the use of, e.g., a nebulizer, a dry powder inhaler or a metered dose inhaler.

The dosage and dose rate of the antibodies of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, an antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

Diagnostic Methods

The antibodies of this invention can be used to diagnose diseased conditions associated with altered $\alpha_v\beta_6$ expression levels. A tissue sample from a subject, such as a tissue biopsy, body fluid sample or lavage (e.g., alveolar lavage), can be tested in an antigen capture assay, ELISA, immunohistochemistry assay, and the like using the antibodies. A tissue sample from a normal individual is used as control.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual*, 2nd edition (Sambrook et al., Eds.), 1989; *Oligonucleotide Synthesis*, (M. J. Gait, Ed.), 1984; U.S. Pat. No. 4,683,195 to Mullis et al.; *Nucleic Acid Hybridization*, (B. D. Hames and S. J. Higgins), 1984; *Transcription and Translation*, (B. D. Hames and S. J. Higgins), 1984; *Culture of Animal Cells* (R. I. Freshney, Ed.), 1987; *Immobilized Cells and Enzymes*, IRL Press, 1986; *A Practical Guide to Molecular Cloning* (B.

Perbal), 1984; *Methods in Enzymology*, Volumes 154 and 155 (Wu et al., Eds.), Academic Press, New York; *Gene Transfer Vectors for Mammalian Cells* (J. H. Miller and M. P. Calos, Eds.), 1987; *Immunochemical Methods in Cell and Molecular Biology* (Mayer and Walker, Eds.), 1987; *Handbook of Experiment Immunology*, Volumes I-IV (D. M. Weir and C. C. Blackwell, Eds.), 1986; *Manipulating the Mouse Embryo*, 1986.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention. All publications and other references mentioned herein are incorporated by reference in their entirety. In case of conflict, the present specification, including definitions, will control. The materials, methods, and examples are illustrative only and not intended to be limiting. Throughout this specification, the word "comprise," or variations such as "comprises" or "comprising" will be understood to imply the inclusion of a stated integer or group of integers but not the exclusion of any other integer or group of integers.

EXAMPLES

The following examples are meant to illustrate the methods and materials of the present invention. Suitable modifications and adaptations of the described conditions and parameters normally encountered in the antibody art that are obvious to those skilled in the art are within the spirit and scope of the present invention.

In the following examples, the 16−/− mice were generated as described in Huang et al., *J. Cell Biol.* 133:921 (1996). Recombinant human LAP was purchased from R & D Systems (Minneapolis, Minn.). Antibody 10D5 was purchased from Chemicon (Temecula, Calif.). The L230 hybridoma was purchased from ATCC and the secreted antibody was purified from the supernatant of saturated cultures by affinity chromatography on immobilized protein A. Isotyping of antibodies was carried out using the ISOSTRIP kit (Roche Diagnostics) according to the manufacturer's instructions. The $\beta_6$-transfected SW480 cell line was prepared as described in Weinacker et al., *J. Biol. Chem.* 269:6940-6948 (1994).

Example 1

Generation of $\beta_6$-Transfected Stable Cell Lines $\beta_6$-transfected NIH 3T3 and FDC-P1 cells were generated by electroporating parent cell lines with a DNA construct containing full length murine β6 cDNA and a neomycin selectable marker. Stably transfected cells were selected by passaging cells in culture medium containing G418 for 14 days followed by fluorescent activated cell sorting (FACS) to isolate cells expressing the highest level of surface B6. Transfected FDC-P1 cells were cultured in DMEM supplemented with 4 mM L-glutamine adjusted to contain 1.5 g/L sodium bicarbonate, 4.5 g/l glucose, and 1.0 mM sodium pyruvate, 10% FBS, 2.5% mouse IL-3 culture supplement, and 1.5 mg/ml active G418. Transfected NIH 3T3 cells were cultured in DMEM supplemented with 10% FBS, 2 mM L-glutamine, penicillin/streptomycin, and 1 mg/ml active G418.

Example 2

Purification of Human Soluble 6

The $\alpha_v\beta_6$ protein was purified essentially as described in Weinacker, supra. A CHO cell line expressing $hs\alpha_v\beta_6$ was cultured, and the resultant supernatant collected by centrifugation. The integrin was purified by affinity chromatography using anti-$\alpha_v$ antibody L230. Purified L230 was cross-linked to CNBr-activated Sepharose 4B (Sigma) at a ratio of 4.8 mg antibody/ml resin. The $\alpha_v\beta_6$ supernatant was loaded at 0.5 mg antibody/ml resin onto the L230 affinity column, and the column was washed with 10 column volumes of each of (1) 50 mM Tris-Cl, pH 7.5, 1 M NaCl, 1 mM $MgCl_2$; (2) 50 mM Tris-Cl, pH 7.5, 50 mM NaCl, 1 mM $MgCl_2$; and (3) 10 mM $Na_3PO_4$, pH 7.0. $Hs\alpha_v\beta_6$ was eluted with 100 mM glycine, pH 2.5 into 1:10 volume of 1 M $Na_3PO_4$, pH 8.0. The protein was dialyzed with several changes against phosphate buffered saline (PBS) and stored at −20° C.

Example 3

Immunization of $\beta_6$−/− Mice $\beta_6$−/− mice were immunized by intraperitoneal (IP) injection with 25 µg of purified recombinant human $\alpha_v\beta_6$ emulsified in complete Freund's adjuvant (CFA) at a volume ratio of 1:1 in a total volume of 200 µl. Alternatively, $\beta_6$−/− mice were immunized via IP injection with $4\times10^6$ $\beta_6$-transfected NIH 3T3 cells resuspended in 100 µl of PBS supplemented with 1 mg/ml of $CaCl_2$ and 1 mg/ml $MgCl_2$, and the same mice were injected at an adjacent site with 100 µl of CFA. Two weeks and four weeks after the initial immunization, the mice were boosted similarly with the same reagents with the exception that incomplete Freund's adjuvant was used in place of CFA. The mice were bled 7 days after the final boost and anti-$\beta_6$ titers were determined by binding of the serum to purified recombinant human $\alpha_v\beta_6$ or to $\beta_6$-transfected cells. In the case of mice immunized with purified recombinant human $\alpha_v\beta_6$, mice were rested for 3 months and reimmunized with the same antigen mixed with ImmunEasy (Qiagen). Three days prior to isolating spleens for hybridoma fusions, the mice were immunized with 12.5 µg of purified recombinant human $\alpha_v\beta_6$ protein by both IP and intravenous injection. On day of fusion, the animals were sacrificed, and their spleens were removed and teased into single cell suspensions. The splenocytes were immortalized by fusion to a drug-selectable cell fusion partner.

Example 4

Screening of Hybridomas

Figure 1B:
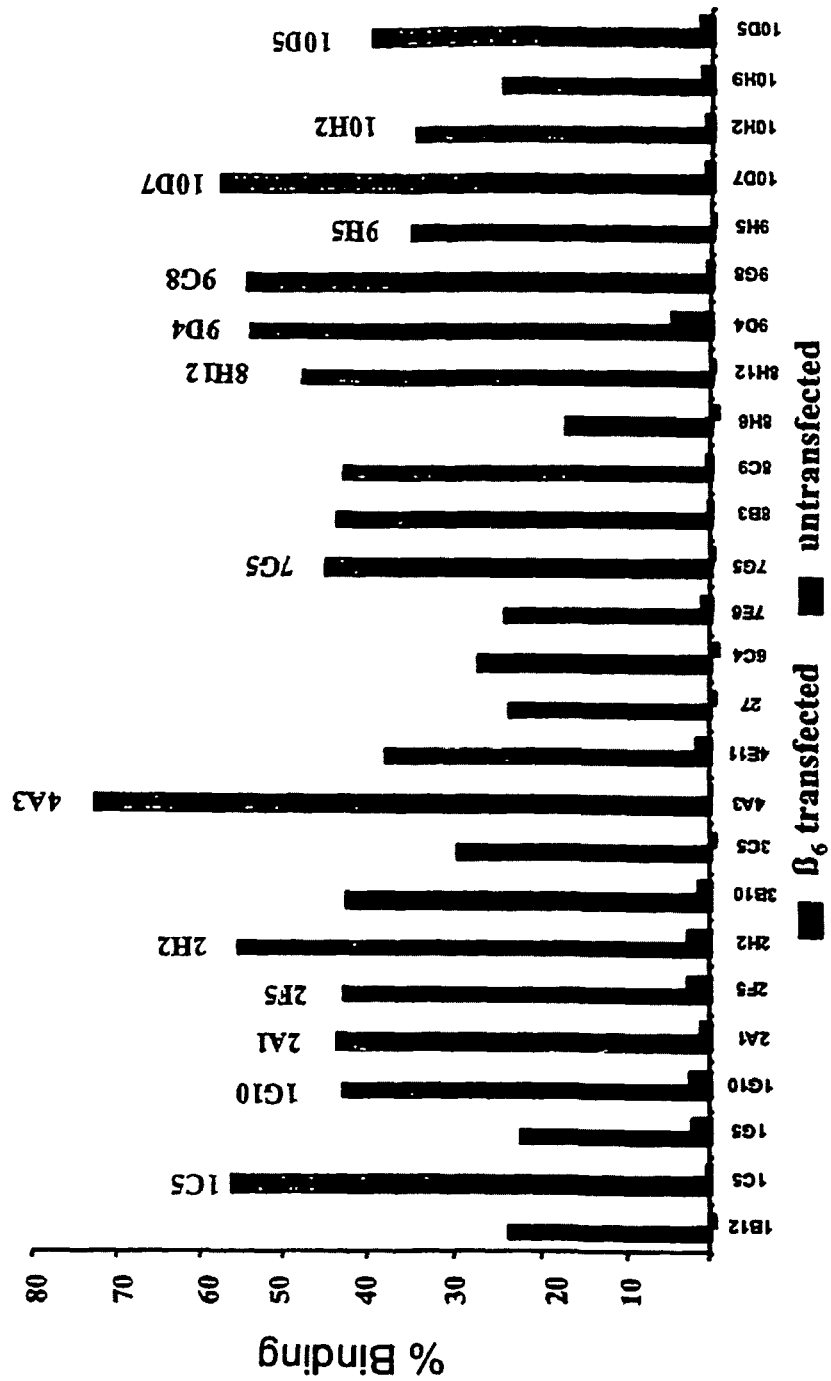

Two groups of antibodies were generated through the immunization of $\beta_6$−/− mice. One set of antibodies were generated through immunization with soluble human truncated $\alpha_v\beta_6$ (Fusion #6). The other set of antibodies were generated through immunization with murine β6-transfected NIH 3T3 cells (Fusion #7). Screening for anti-$\alpha_v\beta_6$ antibodies was carried out using both cell-based and cell-free binding and functional assays as described below. Initial selection of positive clones was based on binding to purified $hs\alpha_v\beta_6$ and $\beta_6$-transfected human and murine cells (untransfected cells as control). Selected clones were expanded and terminal cultures were re-evaluated for binding to both β6-transfected and untransfected cells in cell capture assays (Example 5b, infra) (representative examples shown in FIGS. 1A and 1B, where the prefixes "6." or "7." of the mAb names, which denote Fusion 6 and Fusion 7, respectively, are omitted; see also Table 2 below). Some antibodies bound preferentially to the β6-transfected cells, while others bound to both transfected and untransfected cells, indicating that only a subset of the antibodies had a preference for $\beta_6$ (FIGS. 1A and 1B). Further selection was based on the ability of the antibodies to block binding of both biotinylated hs$\alpha_v\beta_6$ and $\beta 6$-transfected murine cells to LAP. Select clones were subcloned using FACS and stored frozen until use.

Monoclonal antibodies were screened for specificity of binding to $\alpha_v\beta_6$ based on their ability to bind $\beta_6$-transfected cells and not untransfected parent cells. Monoclonal antibodies were further confirmed as specific binders of $\alpha_v\beta_6$ and not of other $\alpha_v$ integrins or non-specific integrins (i.e., non-e, integrins that bind to RGD-containing ligands) based on their lack of binding to cell lines expressing $\alpha_v\beta_3$, $\alpha_v\beta_8$, $\alpha_5\beta_1$, $\alpha_v\beta_1$ or $\alpha_5\beta_1$. These included stably transfected cells as well as untransfected JY, K562, SW480, NIH3T3, and FDCP1 cell lines.

Some of the antibodies that have been deposited with the ATCC are listed below in Table 1.

TABLE 1

Deposited Hybridomas

| Hybridoma clones | ATCC No. | Deposit Date |
|---|---|---|
| 6.1A8 | PTA-3647 | Aug. 16, 2001 |
| 6.2B10 | PTA-3648 | Aug. 16, 2001 |
| 6.3G9 | PTA-3649 | Aug. 16, 2001 |
| 6.8G6 | PTA-3645 | Aug. 16, 2001 |
| 6.2B1 | PTA-3646 | Aug. 16, 2001 |
| 6.2A1 | PTA-3896 | Dec. 5, 2001 |
| 6.2E5 | PTA-3897 | Dec. 5, 2001 |
| 7.1G10 | PTA-3898 | Dec. 5, 2001 |
| 7.7G5 | PTA-3899 | Dec. 5, 2001 |
| 7.1C5 | PTA-3900 | Dec. 5, 2001 |

Example 5

Assays for Screening and Characterization a. $\alpha_v\beta_6$ ELISA

A 96-well microtiter plate (Corning COSTAR EASY-WASH) was coated with 50 μl/well of 5 μg/ml hs$\alpha_v\beta_6$ at 4° C. overnight. The plate was washed with wash buffer (0.1% TWEEN-20 in PBS) four times in an automated plate washer. Then 180 μl/well of 3% BSA in TBS was added and incubated for 1 hr at 25° C. to block nonspecific binding. The plate was washed as above, and dilutions of either hybridoma supernatant (for screening assays) or purified antibody (for characterization) in TBS containing 1 mg/ml BSA, 1 mM CaCl$_2$, and 1 mM MgCl$_2$ were added (50 μl/well). The plate was incubated for 1 hr at 25° C., washed, and then incubated for 1 hr with 50 μl/well of peroxide-conjugated goat anti-mouse IgG+A+M antibody (Cappel). Bound antibody was detected using 3,3',5,5'-tetramethylbenzidine (TMB). Binding was indicated by the absorbency measured at 450 nm.

b. Cell Capture Assay

A 96-well microtiter plate was coated with 50 μl/well of secondary antibody (donkey anti-mouse IgG (Jackson Immunoresearch); 5 μg/ml diluted in 50 mM sodium bicarbonate, pH 9.2) at 4° C. overnight. Plates were washed twice with 100 μl/well of assay buffer (RPMI+2% BSA) and then blocked with 100 l/well of the assay buffer at 37° C. for 1 hr. For FDC-P1 cells and $\beta_6$-transfected FDC-P1 cells, plates were blocked with anti-mouse Ig (Jackson ImmunoResearch; 20 μg/ml) for 10 min at room temperature to decrease non-specific Fc receptor binding by secondary antibody (omitted for other cell types). While the plates were being blocked, the cells were labeled with 2 μM fluorescent dye (Calcein-AM, Molecular Probes) in the assay buffer at $5\times10^6$ cells/ml. The cells were incubated with the dye in the assay buffer with gentle shaking in a 37° C. water bath for 15 min, collected by centrifugation, and resuspended in assay buffer to $5\times10^6$ cells/ml. Following the blocking step, the buffer was discarded by flicking the plate, and 25 μl/well of supernatant or purified antibody was added to the plate. Following a 15 min incubation at 37° C., 25 μl/well of labeled cells were added, and the plate was incubated for 1 hr at 37° C. The plate was washed 3-5 times with the assay buffer (100 μl/well) and fluorescence emitted by captured cells on the plate was recorded. Percent binding was determined by comparing the fluorescence prior to the final wash step (i.e., total cells added) to that after washing (i.e. bound cells).

c. FACS

Cells were harvested by trypsinization, washed one time in PBS, and then resuspended in FACS buffer (1×PBS, 2% FBS, 0.1% NaN$_3$, 1 mM CaCl$_2$, and 1 mM MgCl2). $0.2\times10^5$ cells were then incubated on ice for 1 hr in FACS buffer containing hybridoma supernatant in a total volume of 100 μl. After incubation, the cells were washed two times with ice cold FACS buffer, resuspended in 100 μl of FACS buffer containing 5 μg/ml donkey anti-mouse IgG PE (Jackson ImmunoResearch), and incubated on ice for 30 min. The cells were then washed twice with ice cold FACS buffer and resuspended in 200 μl of FACS buffer. Binding of the PE labeled secondary antibody was monitored by flow cytometry.

d. Binding of Biotin-hs$\alpha_v\beta_6$ to LAP 96-well microtiter plates (Corning COSTAR EASY-WASH) were coated with 0.3 μg/ml recombinant human LAP (R&D Systems, Cat. # 246-LP) diluted in PBS (50 μl/well) at 4° C. overnight. After the coating solution was removed, the plates were blocked with 180 μl/well of 3% BSA/TBS at 25° C. for 1 hr. In a separate 96-well round-bottom plate, 60 μl/well of a 2× stock (0.5 μg/ml (1.25 nM) of biotin-$\alpha_v\beta_6$, 2 mM CaCl$_2$, and 2 mM MgCl$_2$ in TBS containing 1 mg/ml BSA) was combined with 60 μl/well of a 2× stock of either a hybridoma supernatant (for screening) or a purified antibody (also in TBS containing 1 mg/ml BSA) and incubated at 25° C. for 1 hr. After washing the LAP-coated plate with wash buffer (0.1% TWEEN-20 in PBS) 4 times in an automated plate washer, 100 μl of the antibody-$\alpha_v\beta_6$ mixture was transferred to the plate, and incubated for 1 hr at 25° C. The plate was washed as above and incubated with 50 μl/well of a 1:1000 dilution of extravidin-horseradish peroxidase conjugate (Sigma) in TBS (1 mg/ml BSA) for 1 hr at 25° C. Bound protein was detected using the TMB substrate.

e. Adhesion of $\beta_6$-FDC-P1 cells to LAP

A 96-well microtiter plate was coated with 50 μl/well of 0.5 μg/ml recombinant human LAP (R&D Systems) diluted in 50 mM sodium bicarbonate, pH 9.2 at 4° C. overnight. The plate was washed twice with PBS (100 μl/well) and blocked with 1% BSA in PBS (100 μl/well) for 1 hr at 25° C. The plate was washed twice with 100 μl/well of assay buffer (TBS complete plus 1 mM CaCl$_2$ and 1 mM MgCl$_2$). Next, to the individual wells of the plate were added 25 μl of a hybridoma supernatant (or a purified antibody) and 25 μl of $\beta_6$-FDC-P1 cells ($5\times10^6$ cells/ml, labeled with Calcein AM as described above). The plate was incubated at 25° C. for 1 hr, and then washed 4-6 times with the assay buffer (100 μl/well). The fluorescence emitted from cells captured on the plate was recorded. Percentage binding was determined by comparing the fluorescence signal prior to the final wash step (i.e., total cells added) to that after washing (i.e., bound cells).

f. TGF-β Bioassay

The TGF-β bioassay used herein was a variation of the Mink lung epithelial cell (MLEC) PAI-1 luciferase coculture assay described in Abe et al., *Anal. Biochem.* 216:276-284

(1994), in which $\beta_6$-transfected cells were cocultured with the reporter cells to monitor activation of TGF-$\beta$ by $\alpha_v\beta_6$ (Munger, supra). It is a quantitative bioassay for TGF-$\beta$ based on its ability to induce the expression of plasminogen activator inhibitor-1 (PAI-1). In this assay, MLEC cells are stably transfected with an expression construct containing a truncated PAI-1 promoter fused to the firefly luciferase reporter gene. Exposure of the transfected MLEC cells to active TGF-$\beta$ (0.2 to >30 pM) results in a dose-dependent increase in luciferase activity in the cell lysates.

To conduct this assay, TMLC (mink lung epithelial cell line Mv 1 Lu) cells were transfected with the PAI-1-luciferase construct. The transfected cells were grown in DMEM+10% FBS with L-Gln, Pen/Strep and 200 µg/ml G418. SW480 cells transfected with an integrin $\beta_6$ construct ("$\beta_6$-SW480" or "SW480 $\beta_6$" cells) were grown in DMEM+10% FBS with L-Gln and Pen/Strep. Cells were lifted from flasks with PBS+5 mM EDTA, washed in PBS+0.5% BSA, counted by hemocytometer and plated in 96-well plates. SW480-$\beta$6 cells were plated at $4 \times 10^4$ cells/well in the wash buffer. Monoclonal antibodies were diluted in DMEM (serum-free), added to the SW480-$\beta$6 cells and pre-incubated for 20 min at room temperature. TMLC cells were then added at $2 \times 10^4$ cells/well to a final volume of 100 µl. The plates were incubated for 20 hr in a humidified, $CO_2$-enriched incubator. Supernatant from the plates was discarded and replaced with 100 µl of PBS+1 mM $Ca^{2+}$ and 1 mM $Mg^{2+}$. Cells in the plates were then lysed, and the level of luciferase activity was detected with the glow-type reaction Packard LUCLITE kit (#6016911) and TROPIX microplate luminometer.

Example 6

Antibody Purification

Eight hybridoma clones from Fusion #6 (denoted by the prefix "6.") and fourteen hybridoma clones from Fusion #7 (denoted by the prefix "7.") were selected for further scale-up and characterization (Table 2).

A small-scale culture (150 ml) of each hybridoma was prepared, and the supernatant was collected by centrifugation. Antibodies were purified from these supernatants using Protein A affinity chromatography. For the IgG2a isotype antibodies, the supernatant was directly loaded onto Protein A Sepharose 4 Fast Flow (Amersham Pharmacia Biotech, AB, Uppsala, Sweden) (1 ml settled bed volume). The column was washed with PBS, and the IgG fraction was eluted using 25 mM phosphoric acid, 100 mM NaCl, pH 2.8 into 1:20 volume of 0.5 M $Na_3PO_4$, pH 8.6. For the murine IgG, antibodies, the supernatant was adjusted to 1.5 M glycine, 3 M NaCl, pH 8.9 prior to loading, and the column was washed with 25 mM $Na_3PO_4$, 3 M NaCl, pH 8.6 prior to elution. These preparations were used for the in vitro biochemical characterization described herein.

TABLE 2

Characterization of Hybridoma Clones

| Clone Name | Clone No. | Isotype | Blocker* |
|---|---|---|---|
| 6.1A8 | 2 | IgG2a | Y |
| 6.2B10 | 10 | IgG2a | Y |
| 6.3G9 | 25 | IgG1 | Y |
| 6.4B4 | 30 | IgG1 | N |
| 6.6B5 | 46 | IgG1 | N |
| 6.8B4 | 55 | IgG1 | N |
| 6.8G6 | 56 | IgG1 | Y |
| 6.2B1 | 85 | IgG1 | Y |
| 7.1C5 | 2 | IgG2a | Y |
| 7.1G10 | 5 | IgG2a | Y |
| 7.2A1 | 6 | IgG2a | Y |
| 7.2F5 | 11 | IgG2a | Y |
| 7.2H2 | 12 | IgG2a | Y |
| 7.4A3 | 17 | IgG2a | Y |
| 7.7G5 | 32 | IgG1 | Y |
| 7.8H12 | 39 | IgG2a | Y |
| 7.9D4 | 40 | IgG2a | N |
| 7.9G8 | 41 | IgG2a | Y |
| 7.9H5 | 43 | IgG2a | Y |
| 7.10D7 | 44 | IgG2a | Y |
| 7.10H2 | 46 | IgG2a | Y |

*A blocker is defined as an antibody that blocks the binding of $\alpha_v\beta_6$ to LAP as determined by blocking of ligand binding either to purified hs$\alpha_v\beta_6$ or to $\beta_6$-expressing cells.

For use in animal models, hybridoma clones were scaled up to 2 L of media and grown for 4 weeks in Lifecell Culture Bags-PL732 (Nexell, Cat. No. R4R2113). Antibodies from the hybridomas were purified first by Protein A affinity chromatography as described above, followed by an ion-exchange step on Q Sepharose (Amersham Pharmacia). The eluate from the Protein A chromatography step was adjusted to pH 8.6 using 2 M Tris base, diluted 10-fold with water, and loaded onto a Q Sepharose column (20 mg protein/ml resin) that had been equilibrated in 10 mM $Na_3PO_4$, 25 mM NaCl, pH 8.6. The column was washed with 5 column volumes of equilibration buffer, and bound protein was eluted using 25 mM $Na_3PO_4$, 150 mM NaCl, pH 7.2. The eluted proteins were sterile-filtered (0.45 µm) and stored at $-70°$ C. until use.

Example 7

Characterization of Purified Antibodies

The purified antibodies (Table 2, supra) were characterized quantitatively with respect to their ability to (1) bind hs$\alpha_v\beta_6$, (2) bind $\beta_6$-transfected SW480 and FDC-P1 cells, (3) inhibit binding of biotin-$\alpha_v\beta_6$ to LAP, (4) inhibit binding of $\beta_6$-transfected FDC-P1 cells to LAP, and (5) block $\alpha_v\beta_6$-mediated activation of TGF-$\beta$ in the MLEC assay (supra). The relative potency in each of these assays was compared to that of the known $\alpha_v\beta_6$ antibody 10D5 (Huang et al, *J. Cell Sci.* 111: 2189 (1998)) and, in some cases, the anti-$\alpha_v$ antibody L230. For the characterization of Fusion #7 antibodies, the Fusion #6 antibody 6.8G6 was also used as a positive control.

Figure 2A:
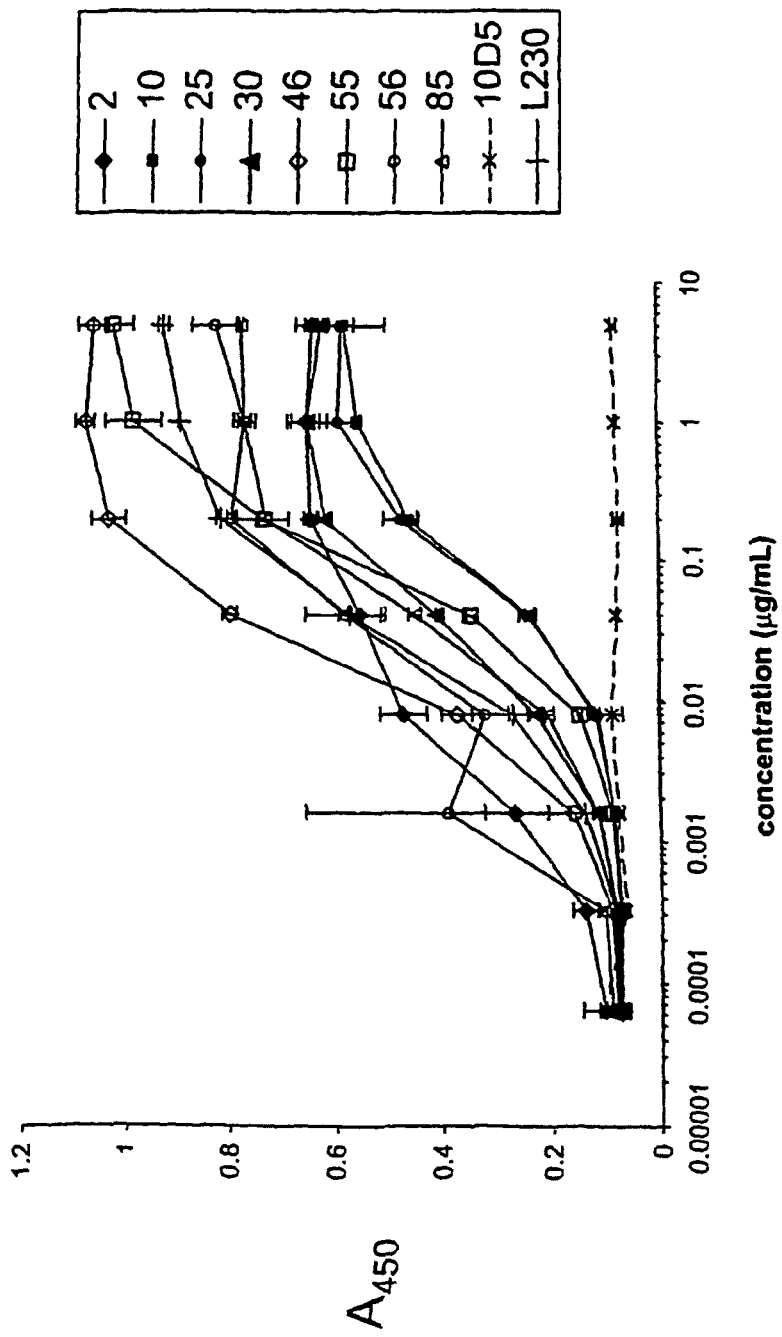
FIG. 2A is a graph showing the results of ELISA assays that determined the ability of various purified anti-$\alpha_v\beta_6$ "Fusion 6" monoclonal antibodies to bind soluble recombinant human $\alpha_v\beta_6$ ("hs$\alpha_v\beta_6$"). These antibodies were generated by immunizing $\beta_6$-/- mice with soluble human truncated $\alpha_v\beta_6$. The numbers in the legend indicate the clone numbers. For the corresponding clone names, see Table 2.
Figure 2B:
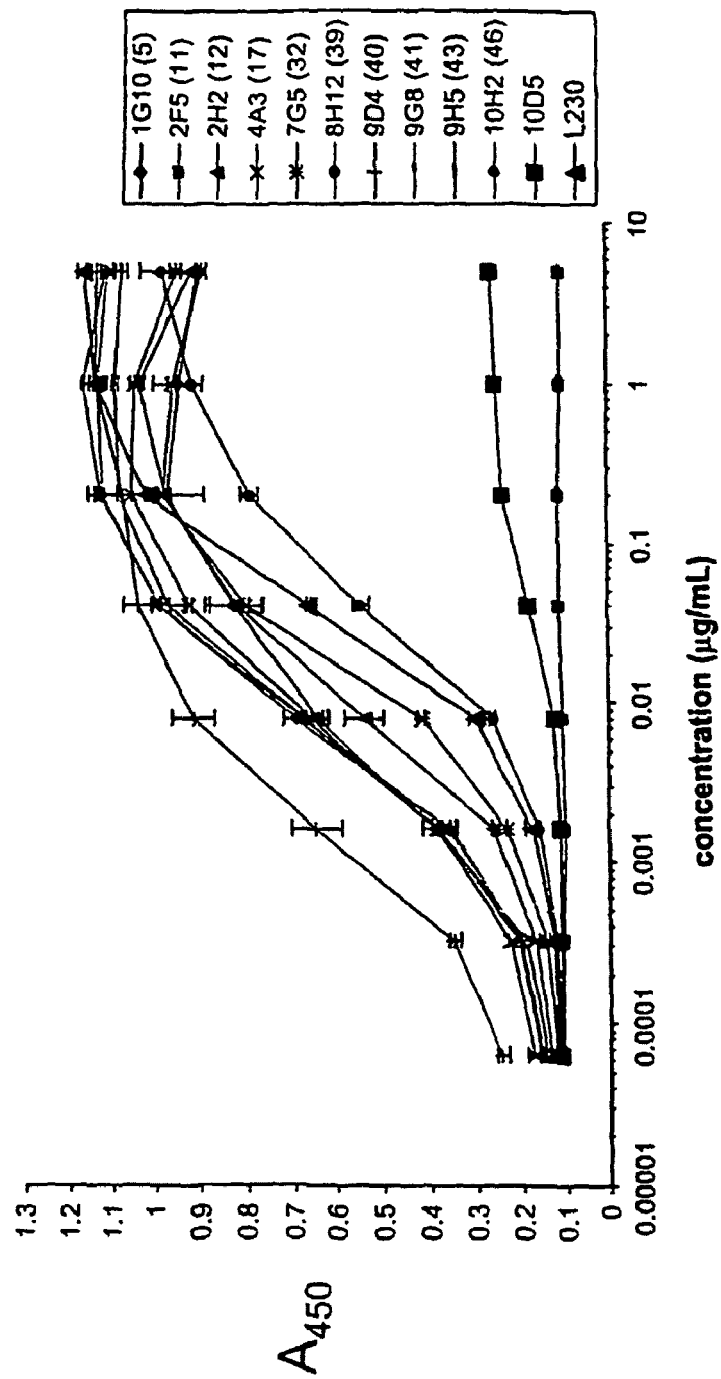
FIG. 2B is a graph showing the results of ELISA assays that determined the ability of various purified anti-$\alpha_v\beta_6$ "Fusion 7" monoclonal antibodies to bind soluble recombinant hs$\alpha_v\beta_6$. These antibodies were generated by immunizing $\beta_6$-/- mice with β6-transfected NIH 3T3 cells (Fusion #7).

An initial binding experiment (Example 5a, supra), carried out in the presence of 1 mM $Ca^{2+}$ and 1 mM $Mg^{2+}$, indicated that a majority of the purified antibodies bound to hs$\alpha_v\beta_6$ (FIGS. 2A and 2B). Unexpectedly, however, no binding was observed for 10D5 and clones 7.2F5 and 7.10D7. A subsequent experiment established that binding of 10D5 (FIG. 3E), 7.2F5, and 7.10D7 was supported only weakly by $Ca^{2+}/Mg^{2+}$, but much more strongly by 1 mM $MnCl_2$. Among the new clones, three (6.1A8 (FIG. 3A), 7.7G5, and 6.8G6 (FIG. 3C)) showed a requirement for divalent cations, although no difference between the $Ca^{2+}/Mg^{2+}$ state and the $Mn^{2+}$-bound state was observed.

The remaining clones showed no requirement for divalent cations, i.e. could bind to the antigen in the presence of 10 mM EDTA (FIGS. 3B, 3D and 3F). FACS analysis of antibody binding to $\beta_6$-transfected NIH 3T3 cells or SW480 cells revealed a similar pattern, with the exception that 10D5, in this context, bound equivalently in the $Ca^{2+}/Mg^{2+}$ and $Mn^{2+}$ states. The requirements for binding to soluble $\alpha_v\beta_6$ may differ from those for binding to cell surface-expressed $\alpha_v\beta_6$ due to a difference in protein conformation or avidity effects.

These results suggest that there are at least 3 different classes of $\beta_6$-blocking antibodies in this group. One of the classes (10D5) distinguishes between the $Ca^{2+}/Mg^{2+}$ and $Mn_{2+}$ conditions. Another class (including 6.1A8, 7.7G5, and 6.8G6) requires cation but does not distinguish between $Ca^{2+}/Mg^{2+}$ and $Mn^{2+}$. The last class (including anti-$\alpha_v$ antibody L230, 6.2B110, 6.3G9 (FIG. 3B), and 6.2B11 (FIG. 3D), 7.1C5, and 7.1G10) is cation-independent.

Figure 4A:
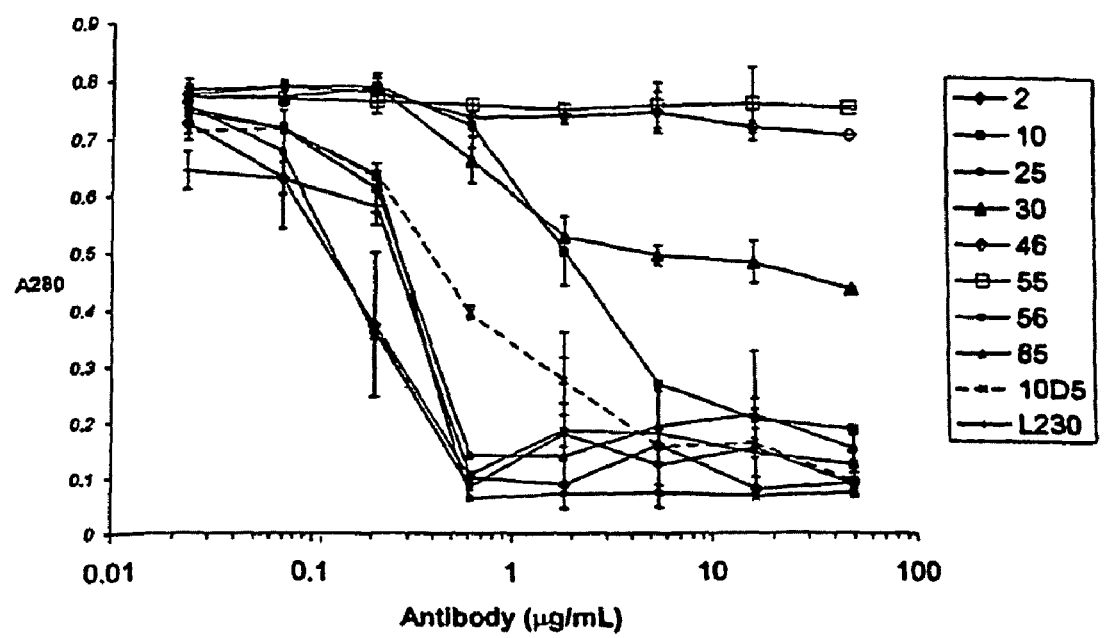
FIGS. 4A and 4B are graphs showing that Fusion #6 and Fusion #7 monoclonal antibodies, respectively, inhibit the binding of biotin-hs$\alpha_v\beta_6$ to LAP.
Figure 4B:
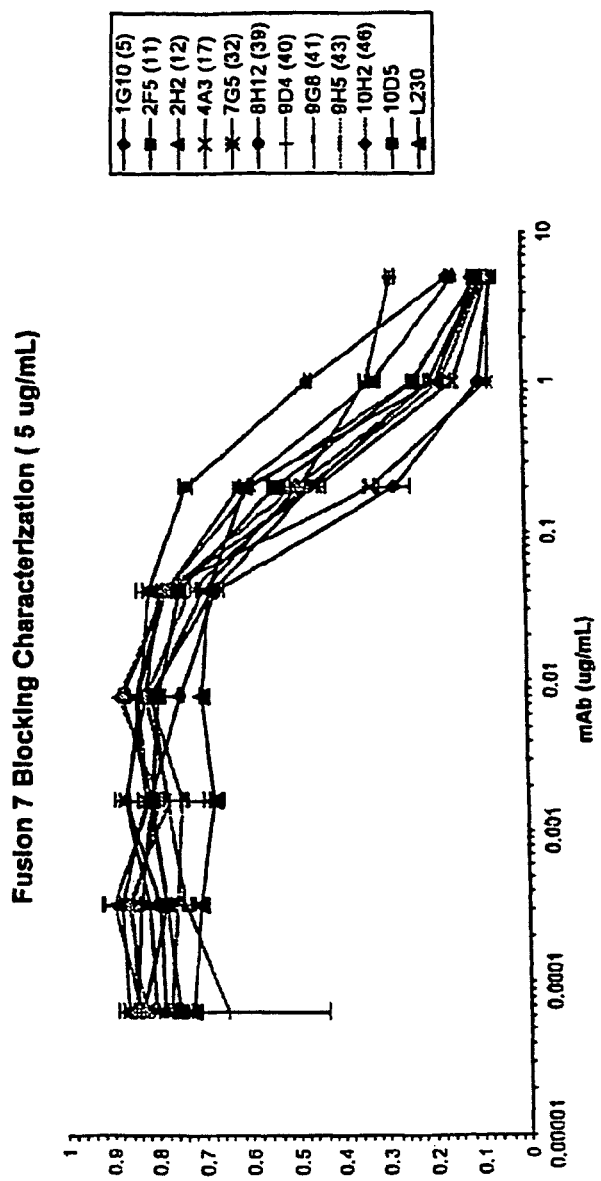
Figure 5E:
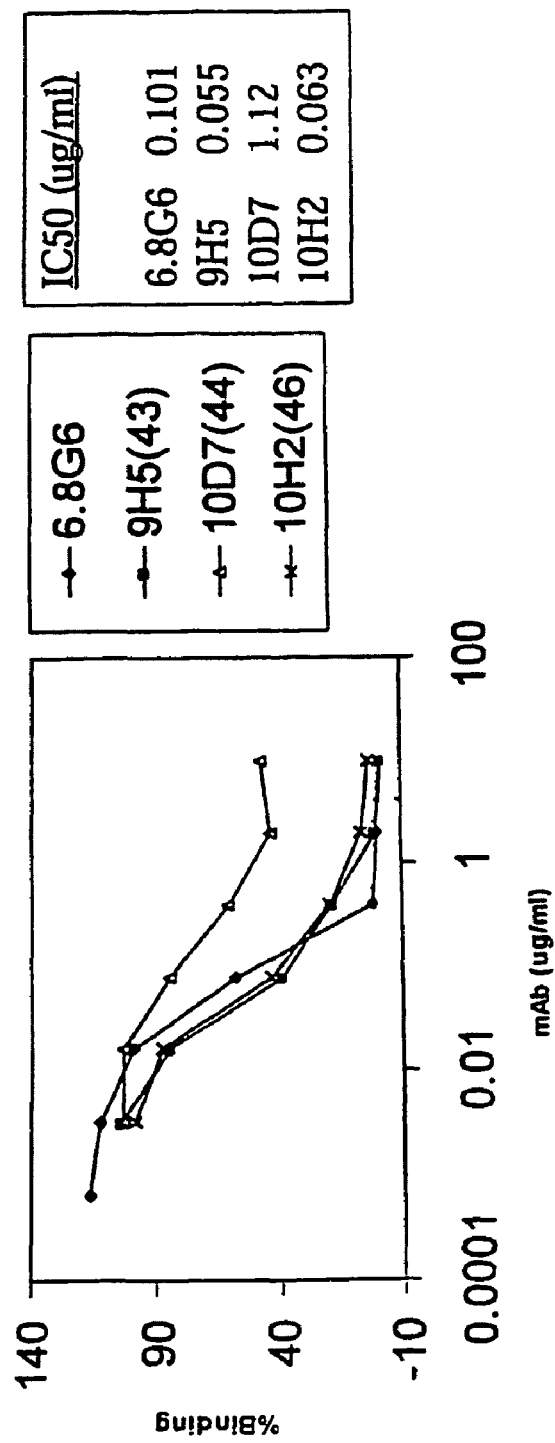

The purified antibodies were next evaluated for their ability to inhibit the $\alpha_v\beta_6$-LAP interaction. In the cell-free assay of Example 5d, supra, antibodies 6.1A8, 6.2B1, 6.3G9, and 6.8G6 showed $IC_{50}$ values lower than that of 10D5 (FIG. 4A; Table 3). 6.2B10 showed a higher $IC_{50}$ but still gave complete inhibition (FIG. 4A). 6.4B4 showed only partial inhibition, whereas 6.6B5 and 6.8B4 showed no inhibition (FIG. 4A). Using the same assay system, antibodies 7.1C5, 7.1G10, 7.2A1, 7.4A3, 7.7G5, 7.9G8, 7.9H5, and 7.10H2 showed $IC_{50}$ values lower than that of 10D5 (FIG. 4B; Table 3). Antibodies 7.2F5, 7.2H2 and 7.8H12 displayed nearly identical or higher $IC_{50}$ values and yet still gave complete inhibition (FIG. 4B).

In the cellular assay described in Example 5e, supra, a similar trend was observed, with the exceptions of 6.1A8, 6.2B110 and 7.9D4, which were much less potent on cells than on purified protein (FIGS. 5A-E; Table 3).

Collectively, these results indicate that we have successfully generated antibodies that specifically inhibit the interaction of both human and murine $\alpha_v\beta_6$ with LAP. Some of these antibodies bound to $\alpha_v\beta_6$ with high affinity (apparent Kd's $\leq$ 0.3 nM, as determined by flow cytometry), inhibited binding of $\beta_6$-transfected cells to LAP with an $IC_{50}$ of $\geq$ 0-0.05 nM (8 ng/mL), and prevented $\alpha_v\beta_6$-mediated activation of TGF-$\beta$1 with an $IC_{50}$ of 2.58 nM (87 ng/mL).

Figure 6A:
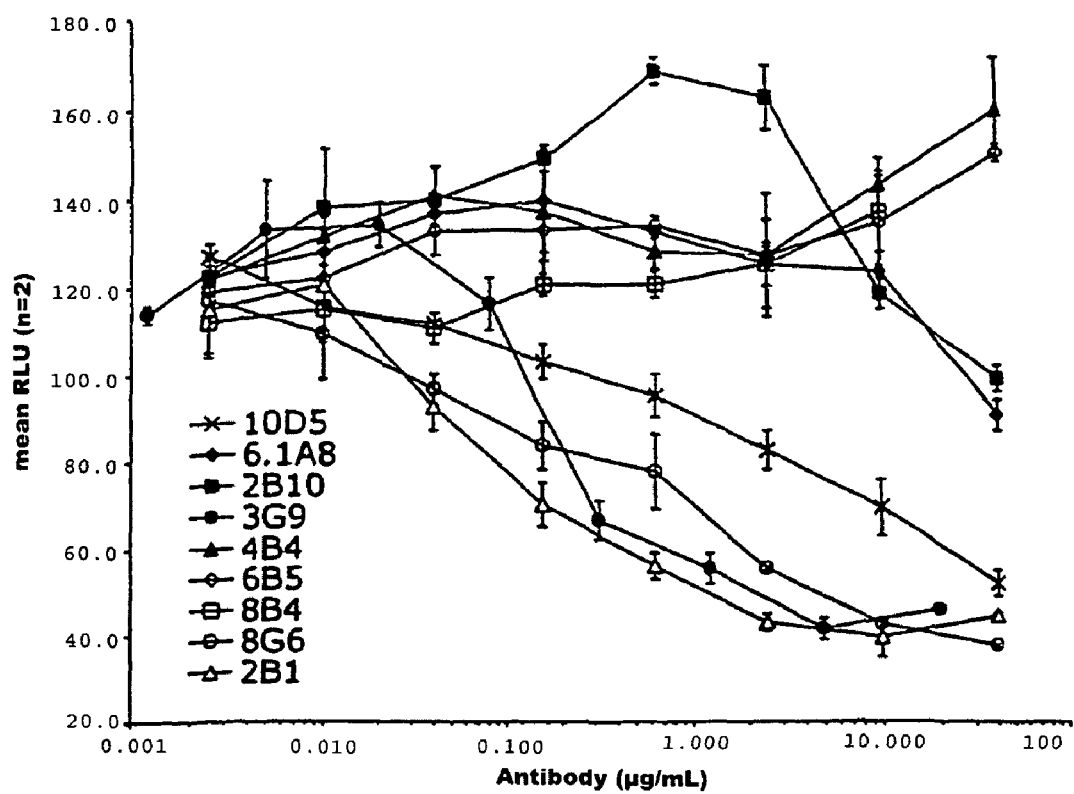
FIGS. 6A and 6B are graphs showing that Fusion #6 and Fusion #7 antibodies, respectively, inhibit the $\alpha_v\beta_6$-mediated activation of TGF-β, using a PAI-1 luciferase reporter gene assay to monitor TGF-β activation.
Figure 6B:
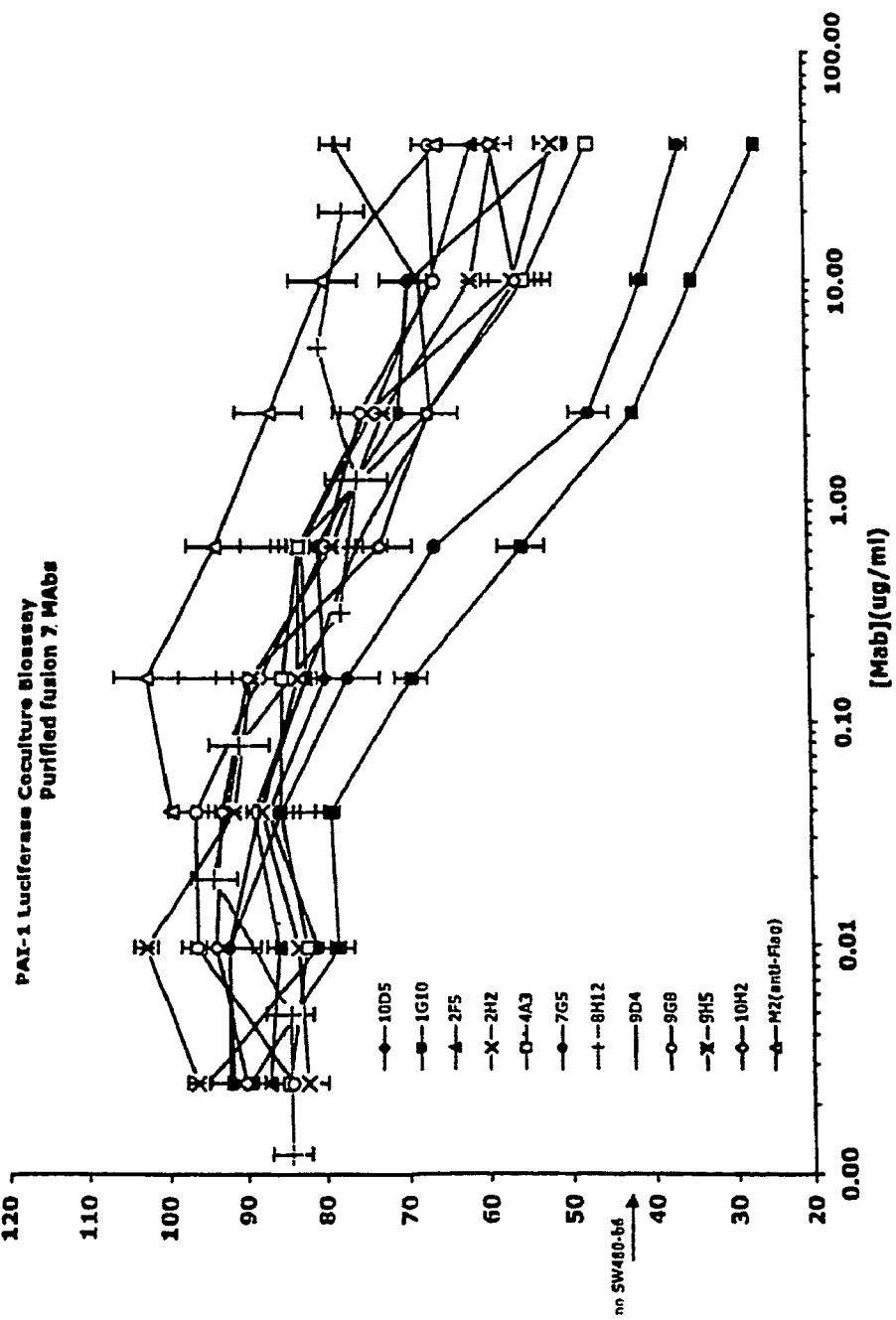

Finally, the purified antibodies were evaluated for their ability to block $\alpha_v\beta_6$-mediated activation of TGF-$\beta$ in the PAI-1/luciferase reporter gene assay (Example 5f, supra). Once again, 6.3G9, 6.8G6, 6.2B1, 7.1G1, and 7.7G5 were able to inhibit $\alpha_v\beta_6$-mediated activation of TGF-$\beta$ with $IC_{50}$ values lower than 10D5, while the remaining antibodies appeared to be significantly less potent in this assay (FIGS. 6A and 6B; Table 3). Thus, the ability to block $\alpha_v\beta_6$'s interaction with LAP correlates with the ability to inhibit activation of TGF-$\beta$ in vitro.

TABLE 3

Characterization of hybridoma clones

| Clone name | Clone No. | $\alpha_v\beta_6$-binding ELISA EC50 (ng/ml) | $\alpha_v\beta_6$-LAP blocking IC50 (ng/ml) | FDCP1-LAP blocking IC50 (ng/ml) | PAI-1 luciferase IC50 (ng/ml) |
|---|---|---|---|---|---|
| 6.2B1 | 85 | 34.7 | 225 | 8 | 87 |
| 6.3G9 | 25 | 76.7 | 271 | 17 | 375 |
| 6.8G6 | 56 | 17.5 | 169 | 23 | 312 |
| 10D5 | — | — | 605 | 50 | 2070 |
| 6.1A8 | 2 | 3.7 | 179 | 2520 | ~40,000 |
| 6.2B10 | 10 | 78.9 | 1950 | >30,000 | >40,000 |
| 6.4B4 | 30 | 25.4 | >50,000 | >30,000 | >40,000 |
| 6.6B5 | 46 | 17.1 | >50,000 | >30,000 | >40,000 |
| 6.8B4 | 55 | 94.4 | >50,000 | >30,000 | >40,000 |
| L230 | — | 27.1 | 229 | n.t.** | n.t. |
| 7.1G10 | 5 | 4.2 | 113 | 30 | 250 |
| 7.7G5 | 32 | 13.0 | 155 | 51 | 700 |
| 7.1C5 | 2 | 2.5* | 80* | 83 | n.t. |
| 7.2A1 | 6 | 5* | 300* | 101 | n.t. |
| 10D5 | — | 43* | 377 | n.t. | 2,000 |
| 7.4A3 | 17 | 5.7 | 204 | 67 | 3,500 |
| 7.10H2 | 46 | 6.6 | 254 | 63 | 3,500 |
| 7.2H2 | 12 | 9.3 | 370 | 106 | 5,500 |
| 7.9H5 | 43 | 7.3 | 230 | 55 | 7,000 |
| 7.9G8 | 41 | 6.2 | 264 | 284 | >20,000 |
| 7.8H12 | 39 | 46.0 | 1140 | 969 | >20,000 |
| 7.2F5 | 11 | >5000 | 529 | 1490 | >20,000 |
| 7.9D4 | 40 | 1.7 | incomplete | >10,000 | >20,000 |
| 7.10D7 | 44 | >5000 | 3000* | 1120 | n.t. |

*Data obtained from separate experiments.
**Not tested.
***: All experiments summarized in Table 3 were conducted in the presence of 1 mM $Ca^{2+}$ and 1 mM $Mg^{2+}$.
****: Antibodies in boldface are prior art antibodies 10D5 and L230, and new antibodies of particular high inhibitory potency for $\alpha_v\beta_6$.

Figure 9A:
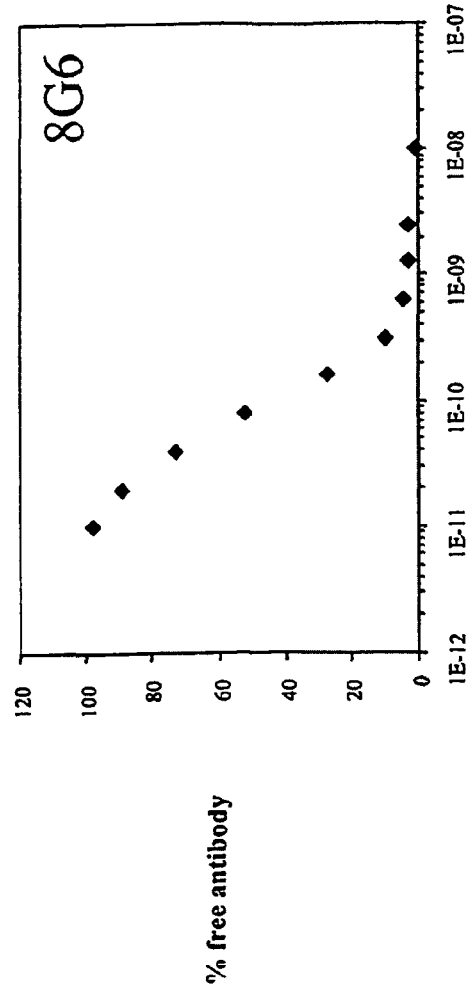
FIGS. 9A and 9B are quadratic curve graphs depicting the solution binding affinities of two anti-$\alpha_v\beta_6$ antibodies, 6.8G6 and 6.3G9, respectively, for soluble $\alpha_v\beta_6$.
Figure 9B:
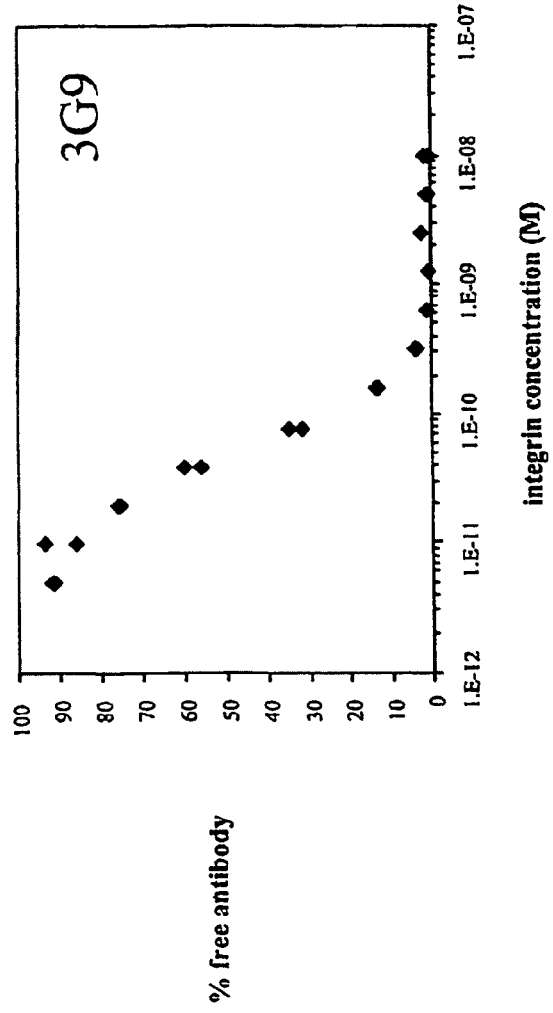

Next, the solution affinities of 6.3G9 and 6.8G6 for soluble $\alpha_v\beta_6$ were determined by using a kinetic exclusion assay (KinExA). A series of dilutions of the soluble integrin ($1\times10^{-8}$ M to $2.4\times10^{-12}$ M) were incubated with $1\times10^{-10}$ M of the antibody for 3 h. These samples were then passed through polymethylmethacrylate beads coated with the integrin using a KinExA instrument (Sapidyne Instruments, Inc., Boise, Id.). In the case of 6.8G6, 11 mM $CaCl_2$ and 11 nM $MgCl_2$ were included in the incubation and assay buffers. The amounts of bound and free antibody were determined using a Cy5-labeled anti-mouse secondary antibody. Quadratic curve fitting was performed using the KinExA software to attain a dissociation constant ($K_d$) for each interaction. The $K_d$'s determined using this method were 15.6 µM for 6.3G9 and 22.8 µM for 6.8G6 (FIGS. 9A and 9B). Thus, both of these antibodies had very high affinities for $\alpha_v\beta_6$.

We further identified classes of anti-$\alpha_v\beta_6$ antibodies that recognized "activated" states of the integrin. There are two potential activation states of $\alpha_v\beta_6$. In the first state, the activated integrin is defined as having a higher affinity for its ligand. Antibodies specific for this activated state showed enhanced binding to the integrin in the presence of activating cations such as 1 mM $MnCl_2$. A comparison of the extent of binding in 1 mM $MnCl_2$ and 1 mM $MgCl_2$ (non-activating cation) by flow cytometry indicated that some of the $\alpha_v\beta_6$ antibodies described here, including 6.1A8 and 6.6B5, showed significantly enhanced binding in the presence of $MnCl_2$.

In a second activated state of $\alpha v\beta 6$, the integrin can activate latent TGF-$\beta$ as described above. A cell line expressing truncated $\alpha_v\beta_6$ (SW480($\beta$6-770T)) was prepared. The cell line was able to bind LAP but could not activate TGF-$\beta$ in the TMLC luciferase assay (Munger et al., supra). Antibodies which bind to the full length #6-transfected SW480 cells, but not to the 770T truncated transfected cells, were thus specific to the form of ($\alpha_v\beta_6$ that is able to activate TGF-$\beta$. Antibodies 7.8B3 and 7.8C9 met this criteria.

Example 8

Epitope Mapping by Antibody Competition

The purified monoclonal antibodies were also tested for their ability to compete with 6.8G6 for binding to biotinylated $\alpha_v\beta_6$ in an ELISA format. In this assay, 6.8G6 was coated on an ELISA plate, and a mixture of the competing antibody and biotinylated $\alpha_v\beta_6$ was added in a buffer containing 1 mM each of $Ca^{2+}$ and $Mg^{2+}$. Bound integrin was detected using extravidin-HRP conjugate, and competing antibodies were scored for their ability to block binding. All consensus blockers (Table 2) except 6.2B10 (a weak blocker) were shown to be able to compete with 6.8G6 to various degrees (Table 4). These data confirm that these consensus blockers bind to the same or overlapping epitope as 6.8G6.

TABLE 4

Epitope Mapping by Antibody Competition

| Clone | Consensus Blocker? | Competition with 6.8G6 |
|---|---|---|
| 6.2A1 | N | − |
| 6.4B4 | N | − |
| 6.6B5 | N | − |
| 6.8B4 | N | − |
| 7.9D4 | Y/N | − |
| 10D5 | Y | ++ |
| L230 | Y | ++ |
| 6.1A8 | Y | ++ |
| 6.2B10 | Y (weak) | − |
| 6.3G9 | Y | + |
| 6.8G6 | Y | ++ |
| 6.2B1 | Y | ++ |
| 7.1C5 | Y | +++ |
| 7.1G10 | Y | +++ |
| 7.2A1 | Y | ++ |
| 7.2F5 | Y | ++ |
| 7.2H2 | Y | ++ |
| 7.4A3 | Y | ++ |
| 7.7G5 | Y | ++ |
| 7.8H12 | Y | ++ |
| 7.9G8 | Y | ++ |
| 7.9H5 | Y | ++ |
| 7.10D7 | Y | + |
| 7.10H2 | Y | ++ |

Figure 10A:
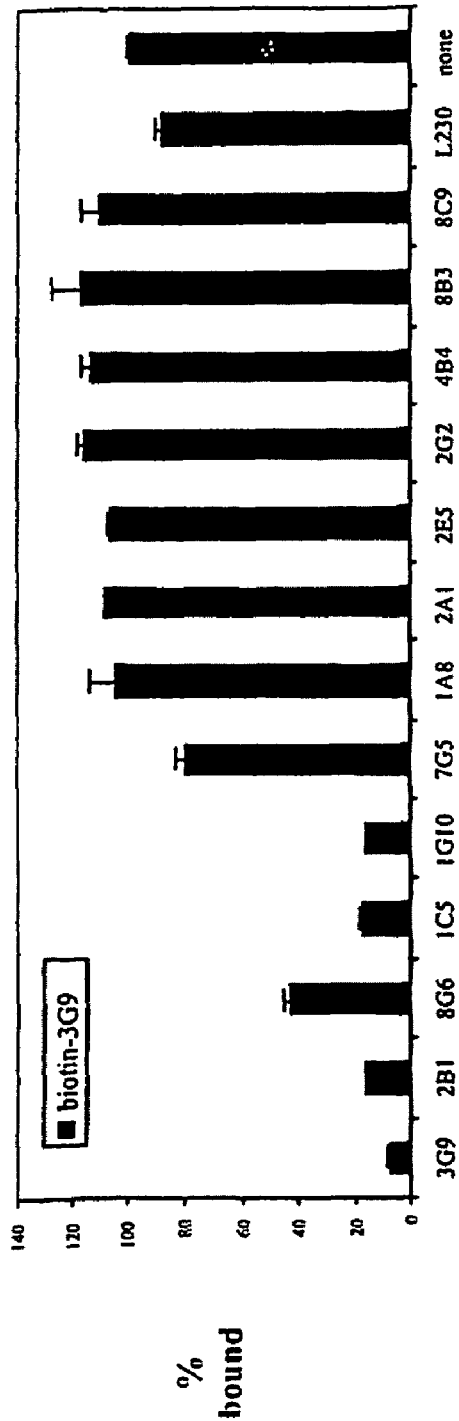
FIGS. 10A and 10B are bar graphs demonstrating the ability of purified monoclonal antibodies to compete with biotinylated 6.3G9 and biotinylated 6.8G6, respectively, for binding to $\alpha_v\beta_6$.
Figure 10B:
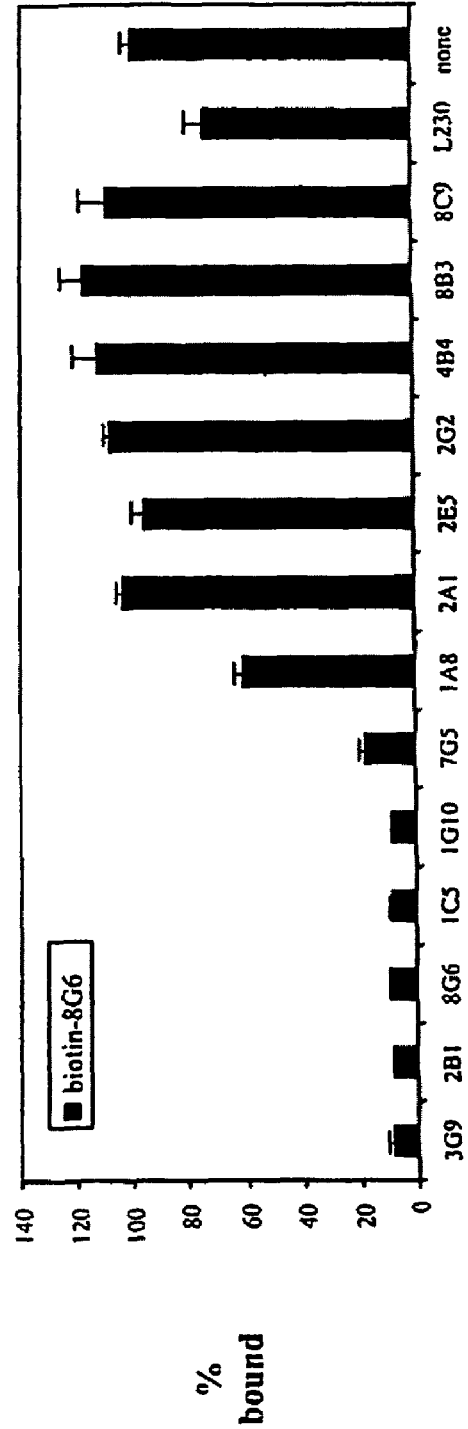

The purified monoclonal antibodies were tested for their ability to compete with biotinylated 6.3G9 or biotinylated 6.8G6 for binding to $\alpha_v\beta_6$ in ELISA. In this assay, unlabeled $\alpha_v\beta_6$ was coated on an ELISA plate, and a mixture of the competing antibody and the biotinylated antibody was added in a buffer containing 1 mM each of $Ca^{2+}$ and $Mg^{2+}$. Bound biotinylated antibody was detected by using neutravidin-HRP conjugate. The data showed that the most potent blocking antibodies (e.g., 6.2B1, 7.1C5, and 7.1 G10) competed with both 6.3G9 and 6.8G6 for binding to $\alpha_v\beta_6$ (Table 4.1, and FIGS. 10A and 10B). Antibodies 6.1A8 and 7.7G5 showed less competition, probably due to their lower affinity for $\alpha_v\beta_6$. None of the non-blocking antibodies or the anti-$\alpha$, antibody L230 showed any competition with 6.3G9 or 6.8G6 in this assay. These results indicate that the $\alpha_v\beta_6$-specific blocking antibodies bind to the same or overlapping epitopes on $\alpha_v\beta_6$.

TABLE 4.1

Epitope Mapping by Antibody Competition

| Clone | Consensus Blocker? | Competition with biotinylated 6.8G6 | Competition with biotinylated 6.3G9 |
|---|---|---|---|
| 6.3G9 | Y | +++ | +++ |
| 6.2B1 | Y | +++ | +++ |
| 6.8G6 | Y | +++ | ++ |
| 7.1C5 | Y | +++ | +++ |
| 7.1G10 | Y | +++ | +++ |
| 7.7G5 | Y | ++ | + |
| 6.1A8 | Y | ++ | + |
| 6.2A1 | N | − | − |
| 6.2E5 | N | − | − |
| 6.2G2 | N | − | − |
| 6.4B4 | N | − | − |
| 7.8B3 | N | − | − |
| 7.8C9 | N | − | − |
| L230 | Y | − | − |

Example 9

CDR Sequences

Figure 7A:
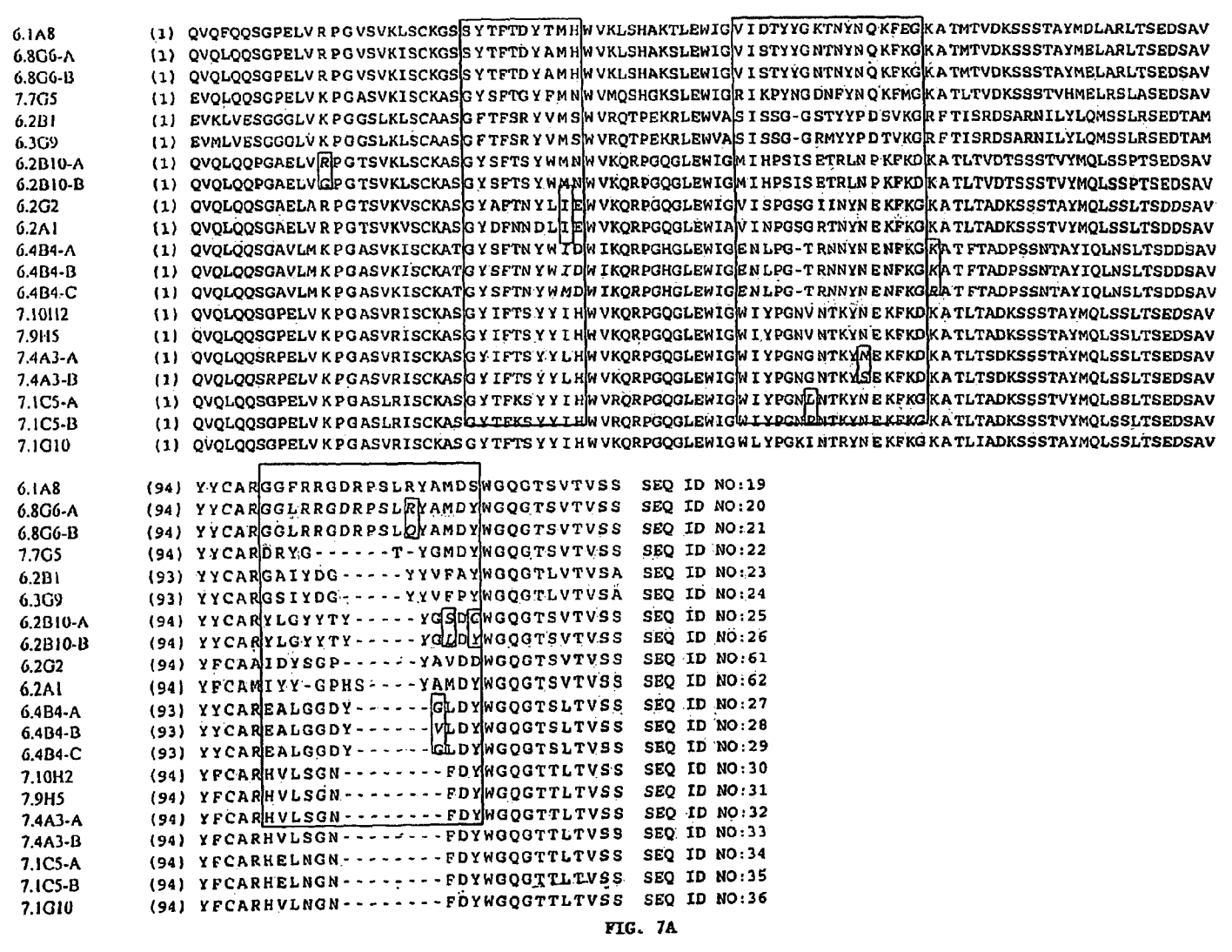

The cDNAs for some of the purified monoclonal antibodies were isolated and sequenced using standard techniques as described in Coligan et al. (eds), *Current Protocols in Immunology*, Wiley, Media, Pa. (2001). The deduced amino acid sequences are shown in FIGS. 7A and 7B.

Amino acid sequences of the heavy chain CDRs of high affinity binders 6.8G6, 6.1A8, 6.2B1, 6.3G9 and 6.2A1 and of nonblocker 6.2G2 are compared as follows (dashes indicate gaps).

```
                  CDR1
6.8G6    SYTFTDYAMH              (SEQ ID NO: 1)

6.1A8    SYTFTDYTMH              (SEQ ID NO: 2)

6.2B1    GFTFSRYVMS              (SEQ ID NO: 3)

6.3G9    GFTFSRYVMS              (SEQ ID NO: 3)

6.2A1    GYDFNNDLIE              (SEQ ID NO: 49)

6.2G2    GYAFTNYLIE              (SEQ ID NO: 50)

CDR2
6.8G6    VISTYYGNTNYNQKFKG       (SEQ ID NO: 4)

6.1A8    VIDTYYGKTNYNQKFEG       (SEQ ID NO: 46)

6.2B1    SISSG-GSTYYPDSVKG       (SEQ ID NO: 5)

6.3G9    SISSG-GRMYYPDTVKG       (SEQ ID NO: 6)

6.2A1    VINPGSGRTNYNEKFKG       (SEQ ID NO: 51)

6.2G2    VISPGSGIINYNEKFKG       (SEQ ID NO: 52)

CDR3
6.8G6    GGLRRGDRPSLRYAMDY       (SEQ ID NO: 7)

6.1A8    GGFRRGDRPSLRYAMDS       (SEQ ID NO: 47)

6.2B1    GAIYDG-----YYVFAY       (SEQ ID NO: 8)

6.3G9    GSIYDG-----YYVFPY       (SEQ ID NO: 9)

6.2A1    IYYGPH-----SYAMDY       (SEQ ID NO: 53)

6.2G2    ID-YSG-----PYAVDD       (SEQ ID NO: 54)
```

In SEQ ID NO:7, the "R" in boldface (the twelfth residue) indicates that it is subject to polymorphism and can be, for example, a Q.

Amino acid sequences of the light chain CDRs of these four high affinity binders and of nonblocker 6.2G2 are compared as follows.

```
              CDR1
6.8G6    RASQSVSTSS-YSYMY    (SEQ ID NO: 10)

6.1A8    RASQSVSIST-YSYIH    (SEQ ID NO: 48)

6.2B1    SASSSVSSS----YLY    (SEQ ID NO: 11)

6.3G9    SANSSVSSS----YLY    (SEQ ID NO: 12)

6.2A1    KASLDVRTAVA         (SEQ ID NO: 55)

6.2G2    KASQAVNTAVA         (SEQ ID NO: 56)
              CDR2
6.8G6    YASNLES             (SEQ ID NO: 13)

6.1A8    YASNLES             (SEQ ID NO: 13)

6.2B1    STSNLAS             (SEQ ID NO: 14)

6.3G9    STSNLAS             (SEQ ID NO: 14)

6.2A1    SASYRYT             (SEQ ID NO: 57)

6.2G2    SASYQYT             (SEQ ID NO: 58)
              CDR3
6.8G6    QHNWEIPFT           (SEQ ID NO: 15)

6.1A8    QHSWEIPYT           (SEQ ID NO: 16)

6.2B1    HQWSSYPPT           (SEQ ID NO: 17)

6.3G9    HQWSTYPPT           (SEQ ID NO: 18)

6.2A1    QQHYGIPWT           (SEQ ID NO: 59)

6.2G2    QHHYGVPWT           (SEQ ID NO: 60)
```

As shown in FIGS. 7A and 7B, the mAbs that fall into the divalent cation-dependent class (e.g., 6.1A8 and 6.8G6) seem to contain very similar amino acid sequences within the CDRs, while the divalent cation-independent mAbs (e.g., 6.2B1 and 6.3 G9) contain another set of motifs in their CDRs.

The potency and specificity of anti-$\alpha_v\beta_6$ monoclonal antibodies may be governed by subtly different amino acid residues. In the case of 6.1A8 and 6.8G6, the amino acid sequences of the variable domains are very similar, containing 10 amino acid differences in the heavy chain, three of which are conservative, and 11 amino acid differences in the light chain. Yet these antibodies have a roughly 100-fold difference in activity in in vitro assays. The amino acid differences are dispersed throughout the variable domains of the polypeptide chains and these residues may function alone or synergistically with residues on the same chain or the partner chain to affect the potency of the antibodies. In the heavy chain, seven residues are located such that they are likely to be in close proximity to, or play an active role in binding to, $\alpha_v\beta_6$.

An RGD motif is found in a number of integrin-binding proteins (ligands). This motif has been shown to mediate their interaction with integrins by directly contacting the binding pocket on the integrin. Because RGD itself is fairly common among integrin-binding proteins, flanking residues outside the motif must play a role in conferring binding specificity to the integrin-ligand interaction. In 6.1A8 and 6.8G6, one such flanking residue is at position 101 in the heavy chain, within CDR3. This amino acid residue flanks the RGD motif and may be located at the site of antigen recognition, contributing to binding potency and specificity.

Other different residues within the same heavy chain CDRs of 6.1A8 and 6.8G6 include those at positions 33 (CDR1); positions 52, 57, and 65 (CDR2); and position 115 (CDR3). Another difference in the heavy chain lies at position 4 in framework 1, which is near the N-terminus. This residue is predicted by crystallographic models to fold close to the CDRs of the antibody and may play an important role in $\alpha_v\beta_6$ binding. The three remaining differences between 6.1A8 and 6.8G6 are conservative differences at positions 20 (framework 1), 44 (framework 2) and 82 (framework 3).

The amino acid sequences of the cation-independent antibodies are also highly homologous. They can be divided into two classes: those that compete with the RGD-containing antibody 6.8G6 (i.e., 6.2B1, 6.3G9, 7.10H2, 7.9H5, 7.1C5, 7.1G10, and 7.4A3); and those that do not (i.e., 6.2A1, 6.2B10 and 6.4B4). The 6.8G6-competing class contains a FXY motif in CDR3 of the heavy chain, whereas the non-competing class does not. This difference suggests that the FXY motif is important for mediating cation-independent binding to $\alpha_v\beta_6$. Additionally, this FXY-containing class of antibodies probably bind to an epitope on $\alpha_v\beta_6$ that is overlapping with, yet distinct from, the RGD-binding pocket. Antibodies 6.2B10 and 6.4B4 do not contain an FXY motif and are poor $\alpha_v\beta_6$ blockers. They were shown to bind to the $\alpha_v\beta_6$ I-domain-like portion and define yet another epitope to which anti-$\alpha_v\beta_6$ antibodies bind. Interestingly, the monoclonal antibody 6.2A1 belongs to the cation-independent class but does not contain the RGD sequence, as with other cation-independent mAbs.

Monoclonal antibody 7.7G5 belongs to the cation-dependent class. However, the light chain sequence of 7.7G5 is highly homologous to the cation-independent, I-domain binding antibody 6.2B10. The heavy chain of 7.7G5 is also similar to cation-independent antibodies in CDR1. Yet its CDR2 and CDR3 are more similar to those of the cation-dependent class. This observation suggests that specific CDRs confer specificity to an antibody. This is particularly true for CDR3 of the heavy chain, presumably due to the high degree of variability within this part of the antibody. In fact, two out of three cation-dependent and seven out of nine cation-independent antibodies contain heavy chain CDR3 sequences that are likely to play an important role in $\alpha_v\beta_6$ recognition. Of note, 7.7G5 lacks an RGD motif but contains an XGD motif in its heavy chain CDR2. This XGD motif may function in a similar fashion to RGD and confer binding affinity/specificity to 7.7G5.

The above sequence observations and inferences made therefrom provide a basis for rational design of specific variable region amino acid sequences that confer specific binding properties.

Example 10

Diagnostic Antibodies

Antibodies that can detect $\alpha_v\beta_6$ expression in paraffin-embedded tissue sections or other tissue samples may be useful as diagnostics. These diagnostic tools can be used to, e.g., detect upregulated $\alpha_v\beta_6$ in tissue sections for such indications as cancer or fibrosis.

In order to identify antibodies that detect $\alpha_v\beta_6$ in paraffin-embedded tissues, we first screened a panel of antibodies for binding to HPLC-purified $\beta_6$ subunit. Antibodies which bind this subunit are likely recognizing linear peptide epitopes, and were therefore expected to have a greater likelihood for success in paraffin-embedded tissues. Binding to purified $\beta_6$ subunit was carried out using an ELISA format identical to that described for measuring $\alpha_v\beta_6$ binding (supra), except with the purified $\beta_6$ integrin, rather than the $\alpha_v\beta_6$ protein, immobilized on the plate. Using this method, a number of Fusion 6 antibodies capable of binding both the purified $\alpha_v\beta_6$ protein and the purified $\beta_6$ subunit were identified. See Table 5, infra, where the prefix "6." in the clone names is omitted.

TABLE 5

Antibody Binding to Purified $\alpha_v\beta_6$ or Purified $\beta_6$ Subunit

| Clone name | Binding to αvβ6 | Binding to HPLC-purified β6 subunit |
|---|---|---|
| 1A1 | + | 6 |
| 1A8 | + | − |
| 1A11 | + | + |
| 1E1 | + | + |
| 1E6 | + | + |
| 1H10 | +/− | − |
| 2A1 | + | + |
| 2A10 | − | − |
| 2B8 | − | − |
| 2B10 | + | − |
| 2C4 | + | + |
| 2C7 | + | + |
| 2E5 | + | + |
| 2G3 | + | − |
| 3A6 | + | − |
| 3B1 | + | − |
| 3B2 | + | + |
| 3B11 | + | + |
| 3C2 | + | + |
| 3D5 | + | − |
| 3D10 | + | + |
| 3F1 | + | − |
| 3G3 | − | − |
| 3G5 | + | − |
| 3G9 | + | − |
| 3H2 | + | − |
| 3H11 | + | − |
| 4A4 | +/− | + |
| 4B2 | + | − |
| 4B4 | + | − |
| 4B10 | + | − |
| 4D2 | + | − |
| 4E4 | + | + |
| 4G3 | + | − |
| 4G4 | + | + |
| 4H4 | + | + |
| 4H12 | + | − |
| 5A2 | + | − |
| 5B6 | + | + |
| 5D6 | + | + |
| 5D8 | − | − |
| 5G9 | + | + |
| 5G10 | + | + |
| 5H3 | + | + |
| 6B1 | + | + |
| 6B5 | + | + |
| 6C4 | + | − |
| 6D12 | + | + |
| 6E6 | + | − |
| 6E10 | + | − |
| 6G3 | +/− | − |
| 7C7 | + | + |
| 7E5 | + | − |
| 7F8 | + | − |
| 8B4 | + | + |
| 8G6 | + | − |
| 9B5 | + | + |
| 9B7 | + | + |
| 9B9 | + | − |
| 9B10 | + | − |
| 9D11 | + | + |
| 9E12 | + | + |
| 9F5 | + | + |
| 9F7 | − | − |
| 9G1 | + | − |
| 9H11 | + | − |
| 10A2 | + | − |
| 10A3 | +/− | − |
| 10A4 | + | − |

TABLE 5-continued

Antibody Binding to Purified $\alpha_v\beta_6$ or Purified $\beta_6$ Subunit

| Clone name | Binding to αvβ6 | Binding to HPLC-purified β6 subunit |
|---|---|---|
| 10A8 | + | − |
| 10A9 | + | − |
| 10B10 | + | − |
| 10D3 | + | − |
| 10D11 | + | − |
| 10E4 | + | + |
| 10F1 | + | − |
| 10F12 | + | − |
| 10G1 | + | − |
| 10G2 | − | − |
| 10H11 | + | + |
| 1A7 | + | − |
| 1D6 | + | − |
| 1D9 | + | − |
| 1F6 | + | − |
| 2B1 | + | − |
| 2D9 | + | + |
| 2G2 | + | + |
| 3D9 | + | + |
| 3E5 | + | − |
| 4C12 | + | − |
| 4E6 | + | + |
| 4G5 | + | − |
| 5A3 | + | − |
| 5B3 | + | − |
| 5B8 | + | + |
| 5B9 | + | − |
| 5F7 | + | − |
| 6C10 | + | + |
| 6D8 | + | − |
| 6F4 | + | − |
| 6G9 | + | − |
| 6H8 | + | + |
| 6H9 | + | − |
| 7A5 | + | + |
| 7A11 | + | − |
| 7E6 | + | + |
| 7G9 | − | + |
| 7H3 | + | − |
| 9A2 | − | − |
| 9A3 | + | + |
| 9A4 | − | − |
| 9A9 | + | − |
| 9D2 | − | − |
| 9D3 | − | − |
| 9E4 | − | − |
| 9F1 | + | − |
| 9F12 | − | − |
| 9G11 | − | − |
| 10B5 | + | − |
| 10B7 | + | − |
| 10B9 | +/− | − |
| 10C5 | +/− | − |
| 10C7 | +/− | − |
| 10D6 | +/− | − |
| 10E12 | +/− | − |
| 10F7 | − | − |

As shown above, some antibodies bound to purified $\beta_6$ subunit. They will have a high likelihood to bind to denatured $\alpha_v\beta_6$ and thus can be useful in detecting $\alpha_v\beta_6$, in paraffin-embedded tissue sections. Other antibodies bound to soluble $\alpha_v\beta_6$ but not the $\beta_6$ subunit. Both types of antibodies were used to stain denatured paraffin-embedded $\beta_6$-transfected SW480 cells and untransfected parent cells, and the data are shown in Table 6.

To stain paraffin-embedded tissues or cells, the sample slides were first de-paraffinized by incubation in the following solutions: (1) Xylene, 5 min, twice; (2) 100% ethanol, 2 min, twice; (3) 95% ethanol, 2 min, twice; (4) 50% ethanol, 2 min, once; and (5) distilled water, 2 min, once. The slides were then incubated in a solution consisting of 200 ml of methanol and 3 ml of 30% $H_2O_2$ for 15 min to block endogenous peroxidase. The slides were rinsed twice in PBS for 2 min each time. The paraffin sections on the slides were then unmasked with pepsin (Zymed 00-3009) for 5 min at 37° C. The slides were rinsed again twice in PBS for 2 min each time. Next, the slides were blocked with avidin and then biotin (Vector SP-2001; Vector Laboratories, Burlingame, Calif.), 10 min each at room temperature, with washing between each incubation as described above. After the blocking solution was drained off the slides, the primary antibody (hybridoma culture supernatant) diluted in PBS/0.1% BSA was applied to the slides and incubated overnight at 4° C.

The next day, the slides were rinsed in PBS as described above. Meanwhile, the avidin-biotin complex-horseradish peroxidase solution (ABC reagent) was prepared as follows: 1 ml of PBS was mixed with 20 µl of solution A (1:50) and 20 µl of solution B (1:50) from Vector Kit PK-6102; and the mixture was incubated for 30 min at room temperature before use. During this time, the slides were incubated for 30 min at room temperature with anti-mouse-biotinylated antibody (1:200) from the Vector Kit with 15 µl/ml normal serum. The slides were then rinsed twice in PBS, 2 min each time. Then the above-described ABC reagent was applied to the slides and incubated for 30 min at room temperature. The slides were rinsed again as described above. Then the substrate (Vector SK-4100), 100 µl of DAB (3,3'-diaminobenzidine), were applied to the slides and incubated for 5 min at room temperature. DAB was prepared as follows: to 5 ml of $H_2O$, add 2 drops of Buffer Stock Solution, mix well; then add 4 drops of DAB Stock solution, mix well; and then add 2 drops of $H_2O_2$ Solution, mix well. Then the slides were rinsed in running water for 2 min. Next, the DAB signal was enhanced for all slides as follows: rinse the paraffin sections in 0.05 M sodium bicarbonate, pH 9.6, for 10 min; blot excess buffer, apply the DAB Enhancing Solution 15 seconds; and then quickly rinse with water for 1 min to stop reaction. The slides were then stained in Mayer's Hematoxylin (a nuclear counterstain) for 1 min. The slides were rinsed in running water for 1 min, and then submerged in PBS for 1 min so that the hematoxylin turned blue. The slides were then rinsed again in running water for 1 min and dehydrated and cleared as follows: submerge in (1) 95% ethanol for 1 min, twice; (2) 100% ethanol for 1 min, twice; and (3) Xylene for 2 min, twice. Coverslips were then applied to the slides using permount.

The results suggested that Fusion 6 antibodies 1A1, 2C4, 3B2, 3B11, 5D6, 5G9, 5H3, 6D12, 7C7, 9B5, 9B7, 9D11, 9F5, 10E4, 10H11, 6H8, 7A5, 7G9, 9A3, 2A1, 2E5, 4E4, 4H4, 8B4, 2G2, and 4E6, all of which could bind to purified $\beta_6$ subunit (Table 5), indeed stained paraffin-embedded $\beta_6$-transfected SW480 cells strongly, while not staining untransfected parent cells (Table 6).

TABLE 6

Antibody Binding to Paraffin-Embedded SW480 Cells

| ID# | Clone name | Binding to SW480/β6+ | Binding to SW480 |
|---|---|---|---|
| 1 | 1A1 | +++ | − |
| 2 | 1A8 | + | + |
| 3 | 1A11 | ++ | − |
| 4 | 1E1 | + | − |
| 5 | 1E6 | ++ | + |
| 7 | 2A1 | +++ | − |
| 10 | 2B10 | − | − |
| 11 | 2C4 | +++ | − |
| 12 | 2C7 | − | − |
| 13 | 2E5 | +++ | − |

TABLE 6-continued

Antibody Binding to Paraffin-Embedded SW480 Cells

| ID# | Clone name | Binding to SW480/β6+ | Binding to SW480 |
|---|---|---|---|
| 17 | 3B2 | +++ | − |
| 18 | 3B11 | ++ | − |
| 25 | 3G9 | − | − |
| 30 | 4B4 | + | + |
| 33 | 4E4 | +++ | − |
| 35 | 4G4 | − | − |
| 36 | 4H4 | +++ | − |
| 39 | 5B6 | + | − |
| 40 | 5D6 | +++ | − |
| 42 | 5G9 | +++ | − |
| 43 | 5G10 | − | − |
| 44 | 5H3 | +++ | − |
| 46 | 6B5 | − | − |
| 48 | 6D12 | +++ | − |
| 52 | 7C7 | ++ | − |
| 54 | 7F8 | − | − |
| 55 | 8B4 | +++ | − |
| 56 | 8G6 | − | − |
| 57 | 9B5 | ++ | − |
| 58 | 9B7 | ++ | − |
| 61 | 9D11 | ++ | − |
| 62 | 9E12 | + | − |
| 63 | 9F5 | ++ | − |
| 68 | 10A3 | − | − |
| 75 | 10E4 | +++ | − |
| 80 | 10H11 | ++ | − |
| 85 | 2B1 | + | + |
| 87 | 2G2 | +++ | − |
| 91 | 4E6 | +++ | − |
| 95 | 5B8 | − | − |
| 98 | 6C10 | + | − |
| 102 | 6H8 | ++ | − |
| 104 | 7A5 | +++ | − |
| 107 | 7G9 | +++ | − |
| 110 | 9A3 | +++ | − |

Example 11

Diagnosis of Cancer $\alpha_v\beta_6$ is normally expressed at negligible to low levels in healthy adult tissues. However, $\alpha_v\beta_6$ expression is upregulated in injury, fibrosis, and cancer (see, e.g., Thomas et al., *J. Invest. Dermatology* 117:67-73 (2001); Brunton et al., *Neoplasia* 3: 215-226 (2001); Agrez et al., *Int. J. Cancer* 81:90-97 (1999); Breuss, *J. Cell Science* 108:2241-2251 (1995)). Thus, antibodies that bind specifically to $\alpha_v\beta_6$ expressed on paraffin-embedded tissues can be used in standard immunohistochemistry techniques to detect $\alpha_v\beta_6$ expression for diagnosis of fibrosis, cancer and any other diseases in which $\alpha_v\beta_6$ is upregulated.

Figure 8:
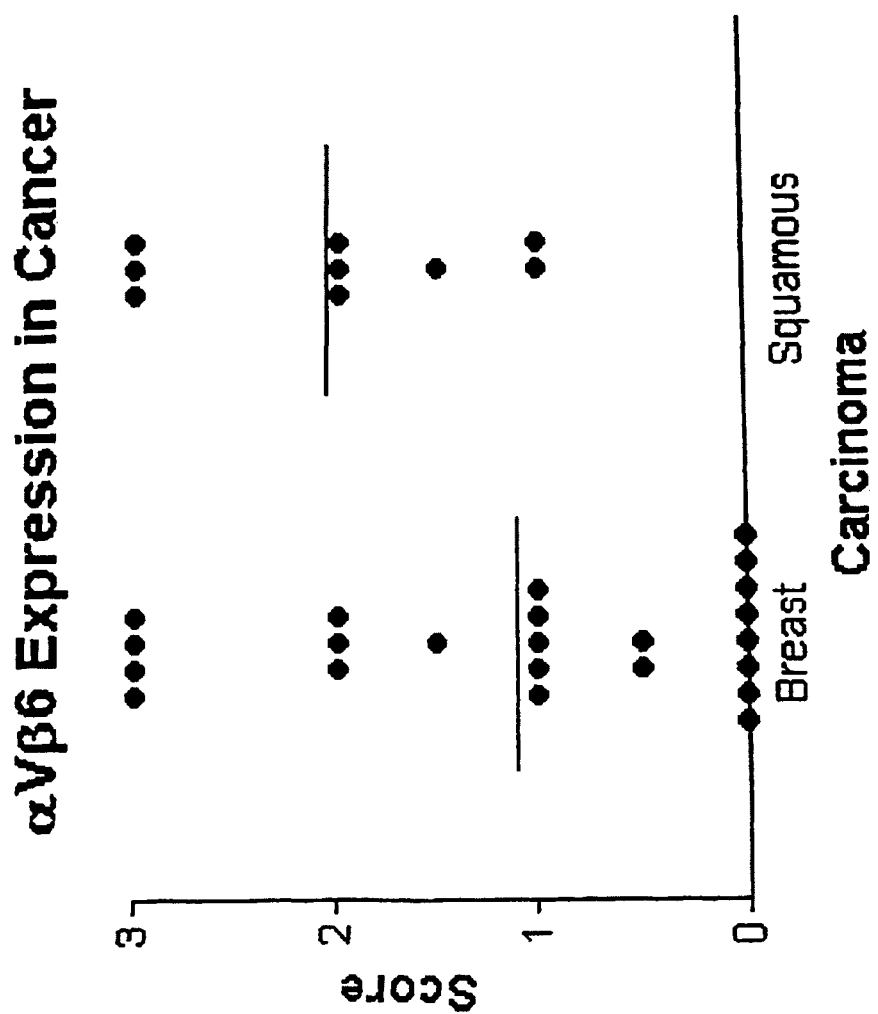
FIG. 8 is a scatter plot showing the expression of $\alpha_v\beta_6$ in human breast cancer and human squamous carcinoma tissue sections. Normal human tissues show only negligible expression levels of $\alpha_v\beta_6$.

As described above, certain antibodies of the present invention bind to HPLC-purified $\beta_6$ integrin and paraffin-embedded and fixed $\beta_6$-transfected cells. These antibodies were also shown to bind to representative squamous and breast cancer tissues in immunostaining. See, e.g., FIG. 8, where monoclonal antibody 6.2A1 was used to show relative staining of paraffin-embedded breast and squamous carcinomas. Thus, these new antibodies are useful as diagnostic tools.

Example 12

Effects of Anti-$\alpha_v\beta_6$ Blocking mAbs in Alport Mice

The collagen 4A3 (COL4A3) knockout (Alport) mice have been established as an in vivo model for kidney fibrosis and used to test the therapeutic effects of pharmacological agents (supra). We tested mAb 6.8G6 (cation-dependent) and 6.3G9 (cation-independent) in Alport mice to determine if they would inhibit the fibrosis normally observed in seven week old Alport mice. As shown above, these two antibodies were found to inhibit $\alpha_v\beta_6$ binding to LAP and to inhibit activation of TGF-$\beta$ in a bioassay. Antibody 1E6 was used as a negative control.

Three week old Alport mice were given intraperitoneal injections 3 times a week with one of the following antibodies: (1) 6.8G6, 4 mg/kg (7 mice); (2) 6.3G9, 4 mg/kg (4 mice); and (3) 1E6, 1 mg/kg (6 mice). The injections were continued for 4 weeks. The mice were then sacrificed, and their kidneys retrieved.

Paraffin-embedded sections of the kidneys were made as described above, and then stained to detect smooth muscle actin, a marker for myoblasts and matrix deposition in kidney fibrosis. We found a significant decrease in smooth muscle actin staining in both the interstitial and glomerular regions of the kidney from the Alport mice treated with mAb 6.8G6 or 6.3G91 as compared to mice treated with 1E6.

Figure 11:
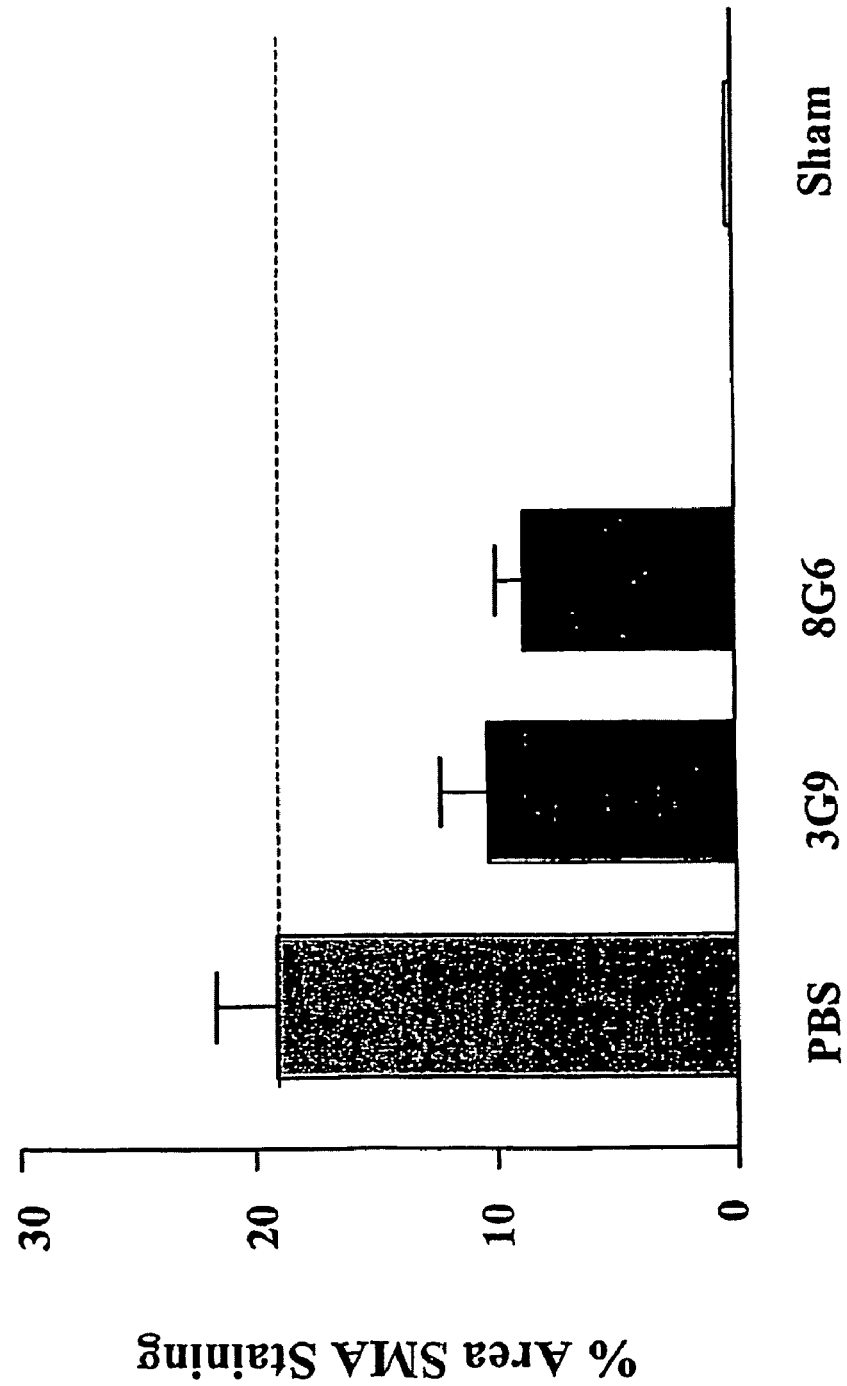
FIG. 11 is a bar graph showing percent smooth actin staining in kidneys from UUO animals treated with anti-$\alpha_v\beta_6$ mAb treatment.

FIGS. 11A and 11B show a dot plot of smooth muscle actin staining in the glomerular and interstitial regions of the Alport kidney. There was significantly reduced smooth muscle actin staining in the kidneys of the Alport mice treated with 6.8G6 and 6.3G9, as compared to negative control 1E6-treated mice.

Example 13

Effectiveness of Anti-$\alpha_v\beta_6$ mAbs in Preventing Unilateral Ureteral Obstruction-Induced Nephrosclerosis We used another mouse model for renal fibrotic progression to test the antifibrotic efficacy of 6.8G6 and 6.3G9. In this mouse model, a ureter of the animal is ligated, resulting in unilateral ureteral obstruction (UUO). UUO causes progressive nephrosclerosis without near-term renal failure in mice because the unobstructed kidney can maintain relatively normal renal function. While the obstructed kidney undergoes rapid global fibrosis, the unobstructed kidney undergoes adaptive hypertrophy.

This study quantitated morphometrically the impact of anti-$\alpha_v\beta_6$ treatment on UUO-induced renal fibrosis. Male, 8-12 week old, viral antigen-free C57BL mice of 25.5±0.2 g in weight (Jackson Laboratories, Bar Harbor, Me.) were used. The mice were allowed to accommodate for seven days prior to beginning the study. The mice had ad libitum access to irradiated standard mouse chow and sterile water throughout the accommodation and experimental period. Body weight was measured at intervals as part of animal health monitoring. The results showed that age-matched unoperated mice gained about 10% body weight over the two-week study period. UUO mice lost about 9% body weight by day 2 but gradually regained the lost body weight by day 14. This weight change pattern occurred irrespective of therapeutic treatment.

To induce renal fibrosis, the left ureter was aseptically isolated via a left-of-midline laparotomy under ketamine: xylazine (100:10 mg/kg s.c.) anesthesia. Two tight, occlusive 6-0 silk ligatures were placed on the ureter at the level of the lower pole of the kidney, and the ureter cut between the ligatures. The abdominal wall was closed with 4-0 Vicryl suture and the skin closed with 4-0 nylon. The animals were allowed to recover on a heating pad and given 0.05 mg/kg s.c. buprenorphine twice daily on days 0 and 1. The procedure was adapted from Ma et al., *Kidney Int.* 53 (4):937-944 (1998).

The mice were then divided into the following study groups:

| Group | Treatment | Dose (mg/kg, i.p.) | n* |
|---|---|---|---|
| 1 | 6.8G6 (cation dependent anti-$\alpha_v\beta_6$ mAb) | 4 | 9 |
| 2 | 6.3G9 (cation-independent anti-$\alpha_v\beta_6$ mAb) | 4 | 8 |
| 3 | 1E6 (negative Control mAb) | 4 | 10 |
| 4 | PBS Vehicle Control | (100 µl) | 8 |
| 5 | Unoperated, Untreated Control | — | 8 |

*Number of animals.

All animals except those in Group 5 were dosed twice weekly beginning on the day before surgery.

The animals were then euthanized with carbon dioxide at day 10 after ligation and dissected. In UUO mice, the renal pelvis and ureter were markedly swollen and fluid-filled above the obstructing ligature. The degree of swelling and extent of remaining renal tissue mass varied among treatment groups. Group 2 showed about half as much swelling as negative control groups. Ligated kidneys were pale in color. Contralateral kidneys were bright red and enlarged by about one third.

Next, both kidneys (left ligated, right unligated) of the animals were removed and halved transversely through the center of the renal pelvis. One half of each kidney was placed in 10% neutral buffered formalin for fixed-tissue staining. The other half of each kidney was placed in 15% sucrose, followed by 30% sucrose, for immunohistochemical staining.

Formalin-fixed kidney sections were immunostained for myofibroblasts (smooth muscle actin), a marker of fibrosis. Images were captured using standardized lighting conditions and digital cameral exposure settings, corrected for background, and calibrated to distance standards. Images of contiguous fields covering the entire left kidney section were taken from each animal for quantitation.

Smooth muscle actin was expressed as a percent of total tissue area within the measured fields. These included all cortical and medullary tissue from the section except the renal papilla.

In conclusion, mice treated with 6.3G9 and 6.8G6 show a significant reduction in fibrosis.

Example 14

Effectiveness of Anti-$\alpha_v\beta_6$ Blocking mAbs Against Bleomycin-Induced Lung Fibrosis in Mice Bleomycin-induced lung fibrosis in mice has been established as an in vivo model for lung fibrosis and used to test the therapeutic effects of pharmacological agents. Inflammation is normally evident 5-15 days following bleomycin treatment. In 129 strain mice, the degree of pulmonary fibrosis progressively increases for up to 60 days after bleomycin treatment. Matrix accumulation usually becomes detectable around day 15. In this example, mAb 6.3G9 was injected intraperitoneally at a concentration of 4 mg/kg/dose into mice with bleomycin-induced lung fibrosis starting at day 0 or day 15, three times weekly. Lung fibrosis was induced at day 0 by administering a single intratracheal dose of bleomycin at a concentration of 0.03 units/kg in 50 µl of sterile saline. The animals were sacrificed at day 30 and the extent of lung fibrosis was assessed. Antibody 1E6 was used as a negative control.

Figure 15A:
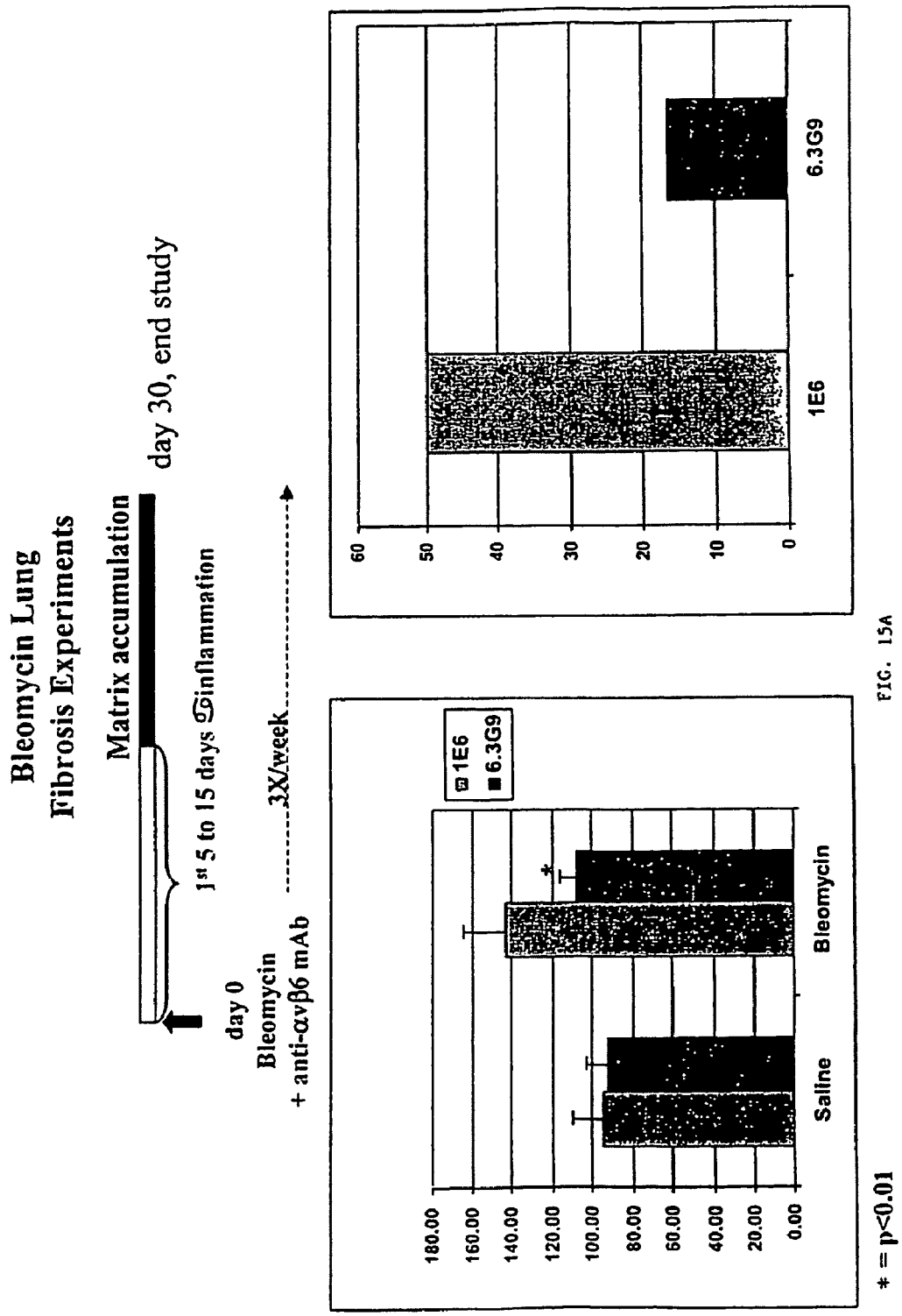
FIGS. 15A-C are graphs showing the effects of anti-$\alpha_v\beta_6$ mAb on bleomycin-induced lung fibrosis. (A) Antibody treatment using 6.3G9 mAb was started on day 0 at the time of bleomycin administration and was monitored over a 30 day period; (B) Antibody treatment using 6.3G9 mAb was started 15 days after bleomycin treatment and was monitored over a 30 day period; (C) Antibody treatment using 6.3G9, 6.8G6 and 6.4B4 mAbs was started 15 days after bleomycin treatment and was monitored over an extended 60 day period. In both FIGS. 15A and 15B, the bar graphs on the left represent μg hydroxyproline/lung while the bar graphs on right show percent increase in hydroxyproline above saline treated mice (no bleomycin).
Figure 15B:
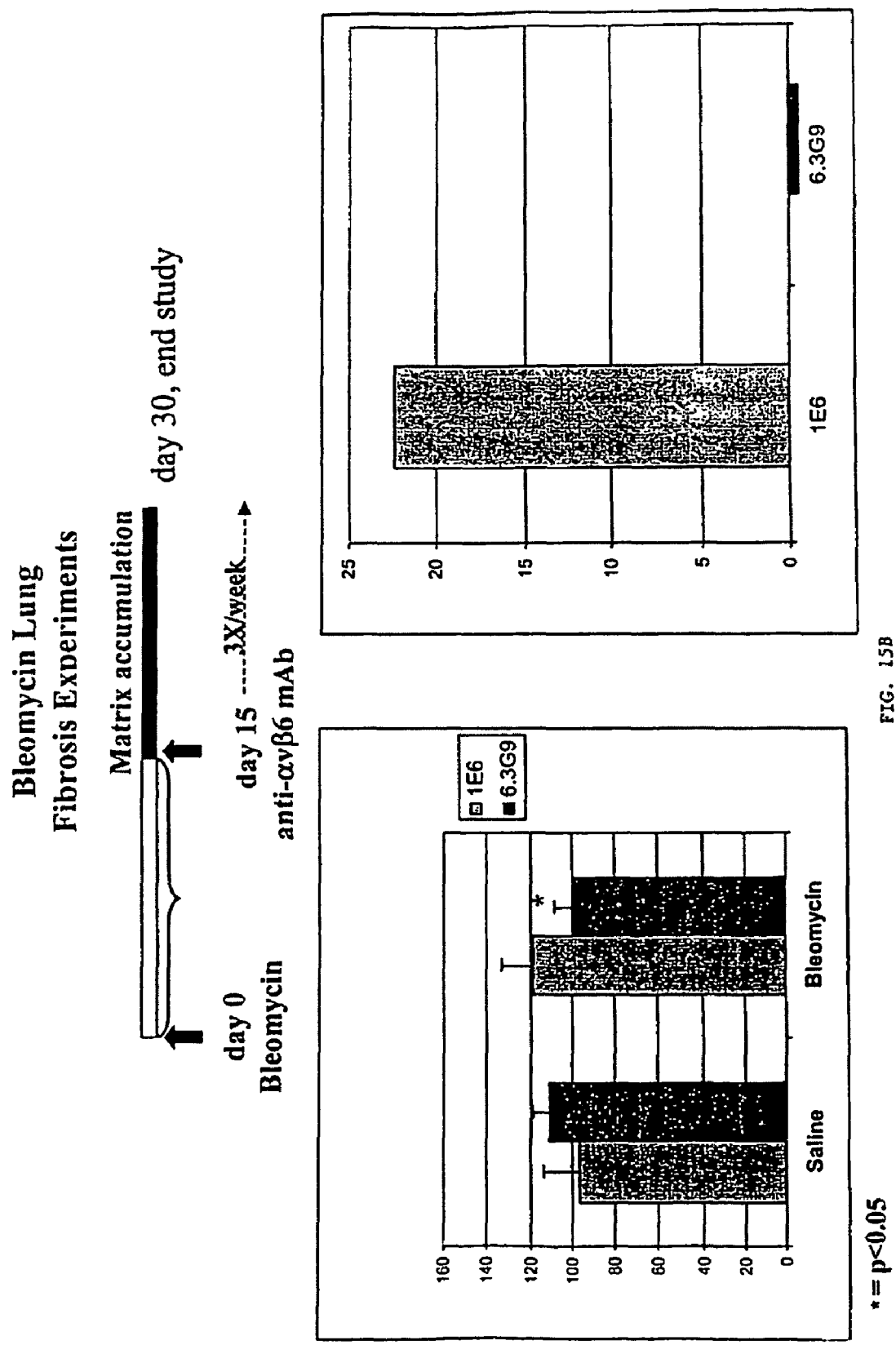

Lungs were harvested from each animal and hydroxyproline content was measured as an index of lung collagen deposition, as described in Munger et al., supra. As shown in FIG. 15A, treatment with 6.3G9 beginning at day 0 significantly inhibited the bleomycin-induced increase in lung hydroxyproline content. Importantly, the 6.3G9 treatment was at least as effective when it began 15 days after bleomycin administration, a time when collagen deposition had already begun.

Figure 15C:
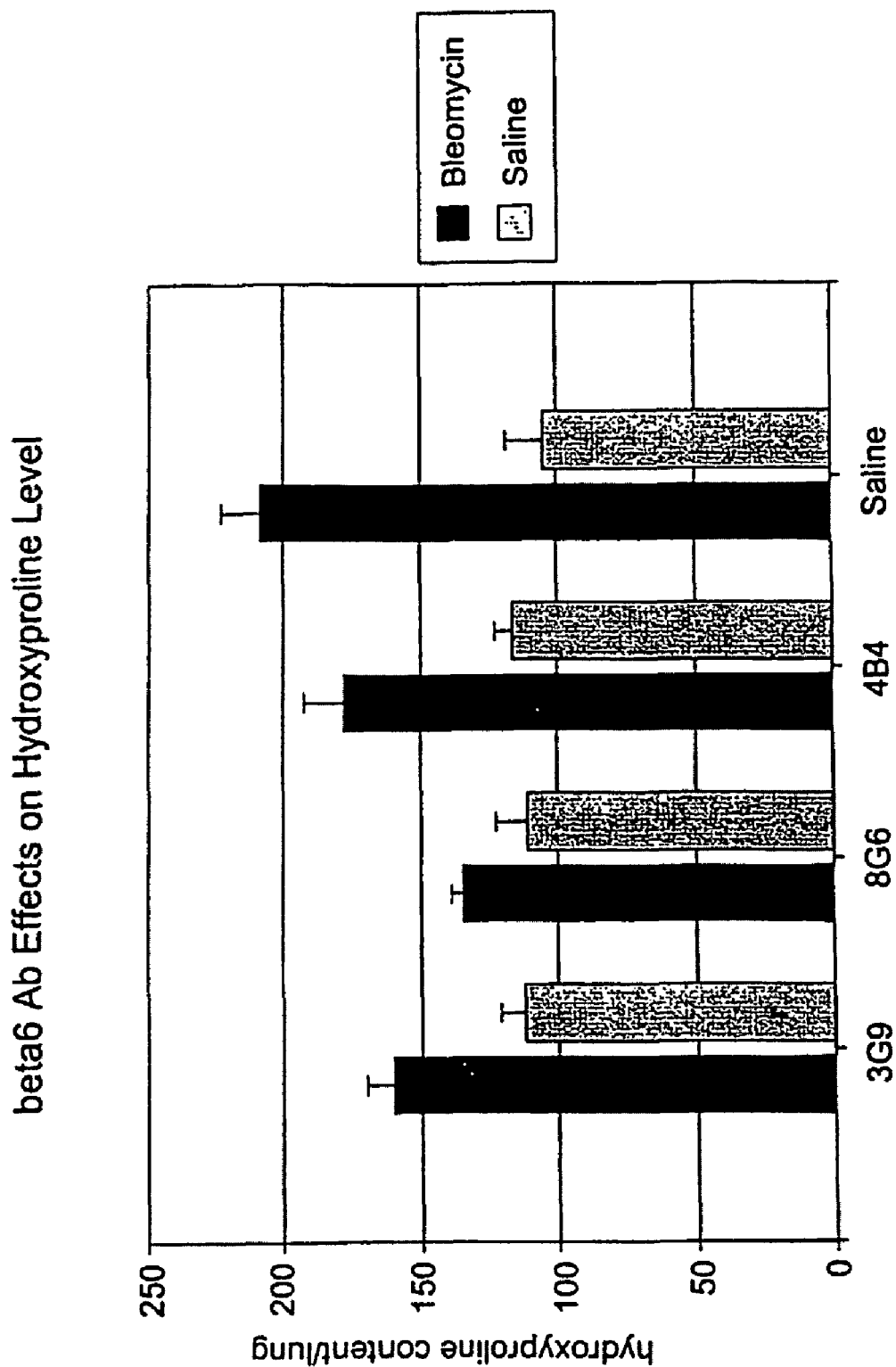

We also examined the effects of 6.3G9, cation-dependent 6.8G6, and the non-blocking antibody 6.4B4 in inhibiting more substantial degrees of lung fibrosis in an extended bleomycin-induced fibrosis protocol (lasting 60 days). To do this, we started the antibody treatments 15 days after bleomycin administration (day 15). Lungs were then harvested at day 60 to determine hydroxyproline content. As shown by FIG. 15C, treatment with 6.8G6 significantly inhibited bleomycin-induced fibrosis (a more than 70% reduction in hydroxyproline content compared to animals treated with bleomycin and saline). Treatment with 6.3G9 also showed a trend toward protection, but these results did not reach statistical significance (FIG. 15C).

In conclusion, both cation-dependent and cation-independent anti-$\alpha_v\beta_6$ blocking mAbs reduced lung fibrosis in mice treated with bleomycin. Furthermore, this intervention was effective even when antibody treatment was not initiated until after the initial onset of fibrosis.

Example 15

Upregulation of $\alpha_v\beta_6$ in Human Psoriasis Lesions

In order to determine whether $\alpha_v\beta_6$ is involved in psoriasis, $\alpha_v\beta_6$ expression was examined on lesional and nonlesional skin biopsies from five psoriasis patients and four normal individuals. Using mAb 6.2A1 immunostaining, we found a significant increase in $\alpha_v\beta_6$ expression in psoriatic lesions, as compared to nonlesional skin from psoriatic patients and normal controls. Thus, the upregulation of $\alpha_v\beta_6$ in psoriatic lesions suggests both diagnostic and therapeutic implication for the use of anti-$\alpha_v\beta_6$ antibodies.

Example 16

Upregulation of $\alpha_v\beta_6$ in Mouse and Human Liver with Biliary Duct Disease As previously discussed, $\alpha_v\beta_6$ expression has been implicated in tissue injury. In this study, expression of $\alpha_v\beta_6$ was investigated in mouse and human liver injured by biliary duct disease.

Hepatic injury in mice was induced by ligation of the biliary duct. See, e.g., George et al., PNAS 96:12719-24 (1999); George et al., *Am J Pathol* 156:115-24 (2000). Using mAb 6.2G2, we found that expression of $\alpha_v\beta_6$ was significantly elevated at days 9, 14 and 16 following biliary duct ligation.

Similarly, human liver sections from patients with biliary duct disease displayed upregulated expression of $\alpha_v\beta_6$, as determined by immunohistochemistry using the mAb 6.2G2. Elevated expression of $\alpha_v\beta_6$ was observed for example, in liver samples from a 44 year old male with acute cholestasis, a post-transplant 59 year old male with acute bile duct obstruction, a 22 year old male with biliary atresia, and a 24 year old male with chronic bile duct obstruction.

In sum, the new anti-$\alpha_v\beta_6$ antibodies are useful diagnostic and therapeutic tools for liver diseases.

Example 17

Upregulation of $\alpha_v\beta_6$ in Various Human Cancers

Integrin $\alpha_v\beta_3$ is normally expressed at negligible to low levels in healthy adult tissues. A variety of human tumor tissues was evaluated for $\alpha_v\beta_6$ expression using the antibody 6.2A1 and methods generally described herein. The results showed that $\alpha_v\beta_6$ integrin expression was significantly upregulated in several human epithelial cancers. Notably, immunohistology showed that $\alpha_v\beta_6$ was expressed especially prominently on the edges of tumor islands in many of the epithelial cancers. To further study expression of $\alpha_v\beta_6$ in epithelial cancer cells, Detroit 562 cells (pharynx carcinoma) and SCC-14 cells (tongue squamous cell carcinoma) as well as SW48096 cells (supra) were stained with 6.3G9 and 6.4B4 and analyzed by flow cytometry.

Figure 12:
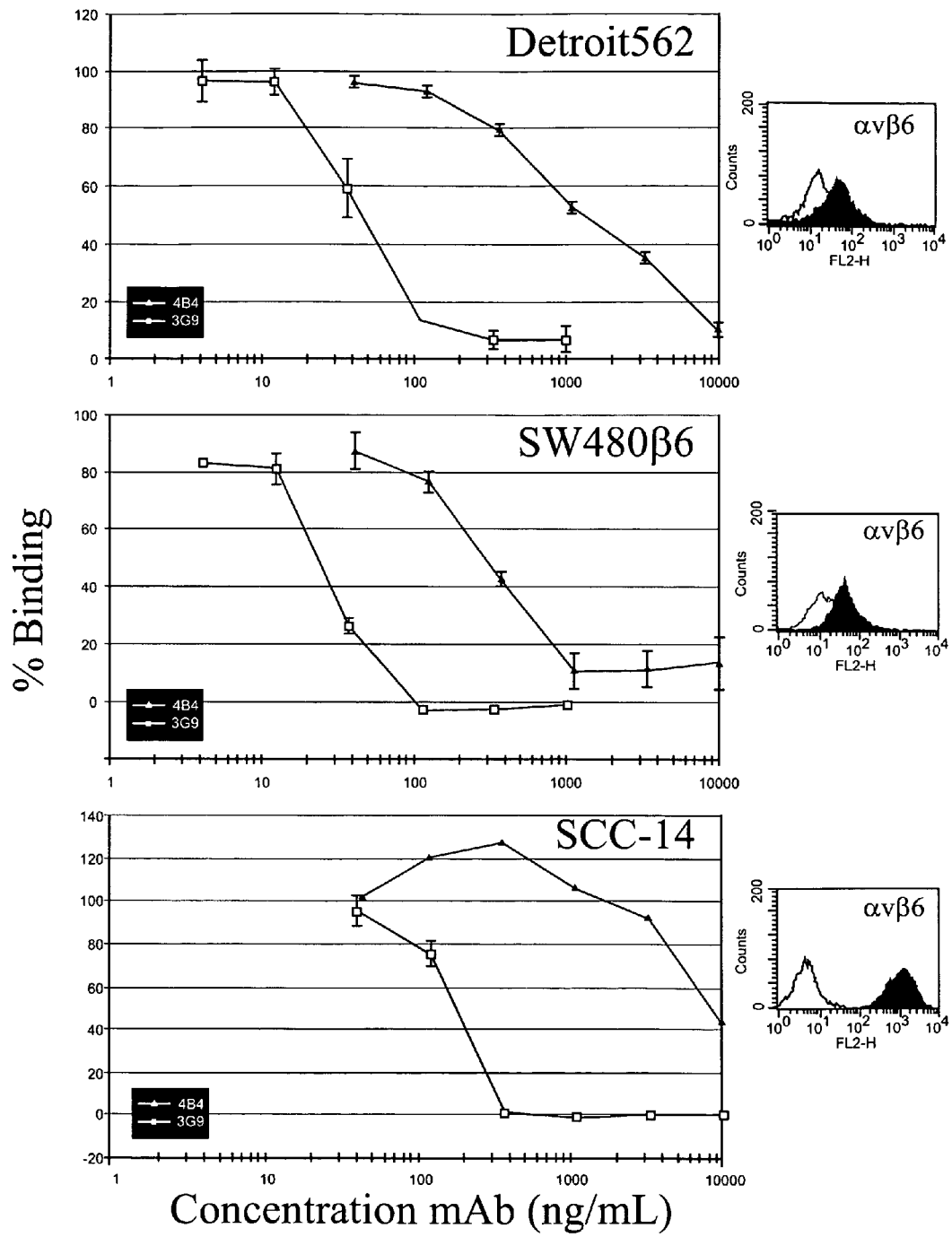
FIG. 12 shows $\alpha_v\beta_6$ expression on tumor cell lines by FACS analysis (right side of figure) and inhibition of tumor cell lines binding to the LAP ligand by mAbs 6.3G9 and 6.4B4 (left side of figure).
Figure 13:
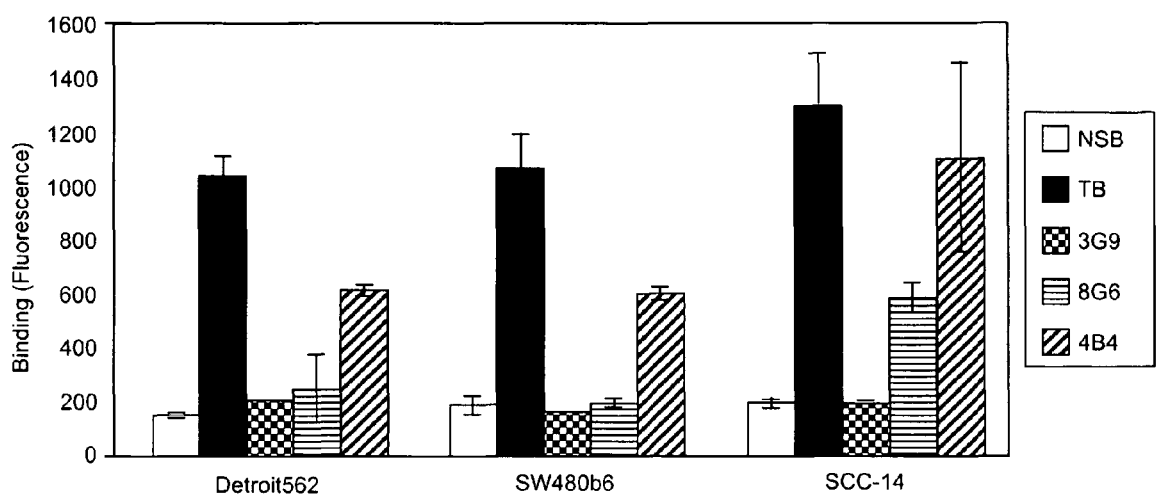
FIG. 13 is a bar graph demonstrating inhibition of three tumor cell lines binding to the LAP ligand by anti-$\alpha_v\beta_6$ mAbs 6.3G9, 6.8G6 and 6.4B4. The mAb binding was compared to total binding without the addition of test mAbs (TB) and nonspecific binding to BSA control alone (NSB).
Figure 14A:
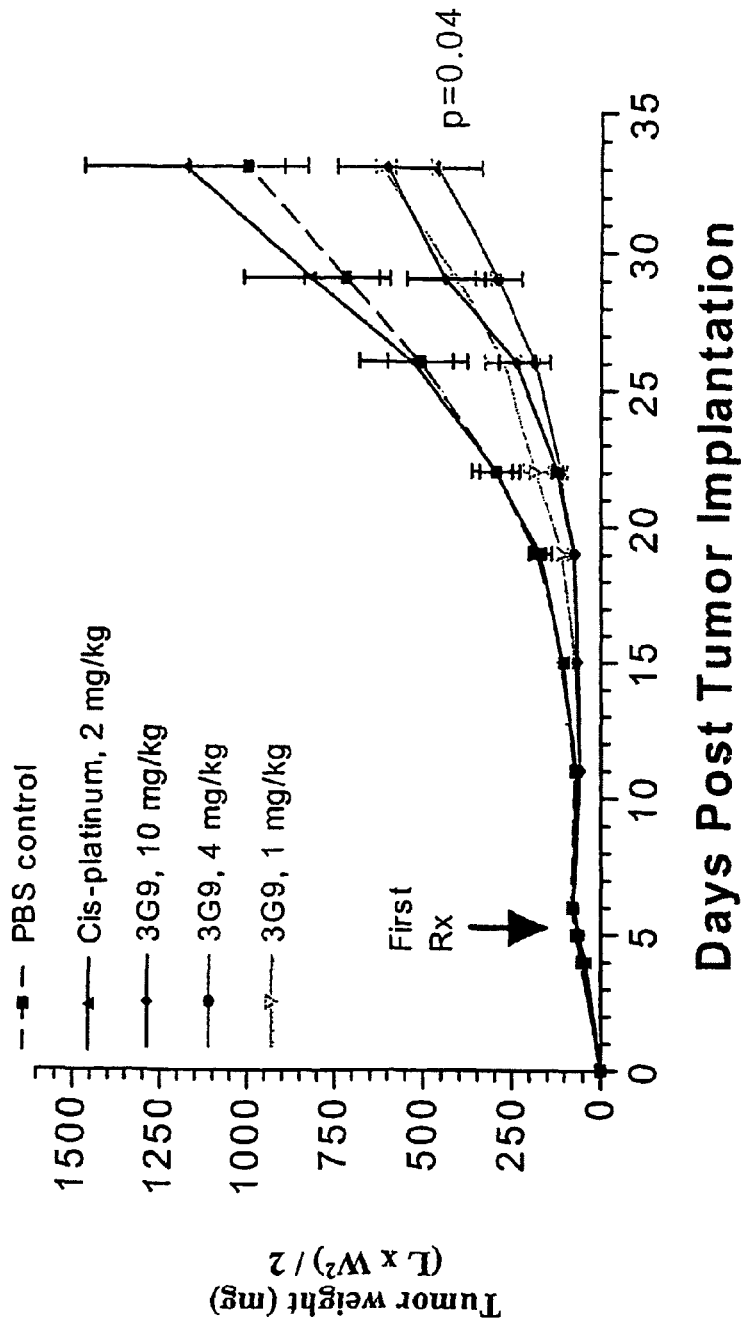
FIGS. 14A and 14B are graphs showing the effects of anti-$\alpha_v\beta_6$ mAb 6.3G9 and 6.4B4, respectively, over a 33 day study period on tumors arising from subcutaneously implanted Detroit 562 cells.
Figure 14B:
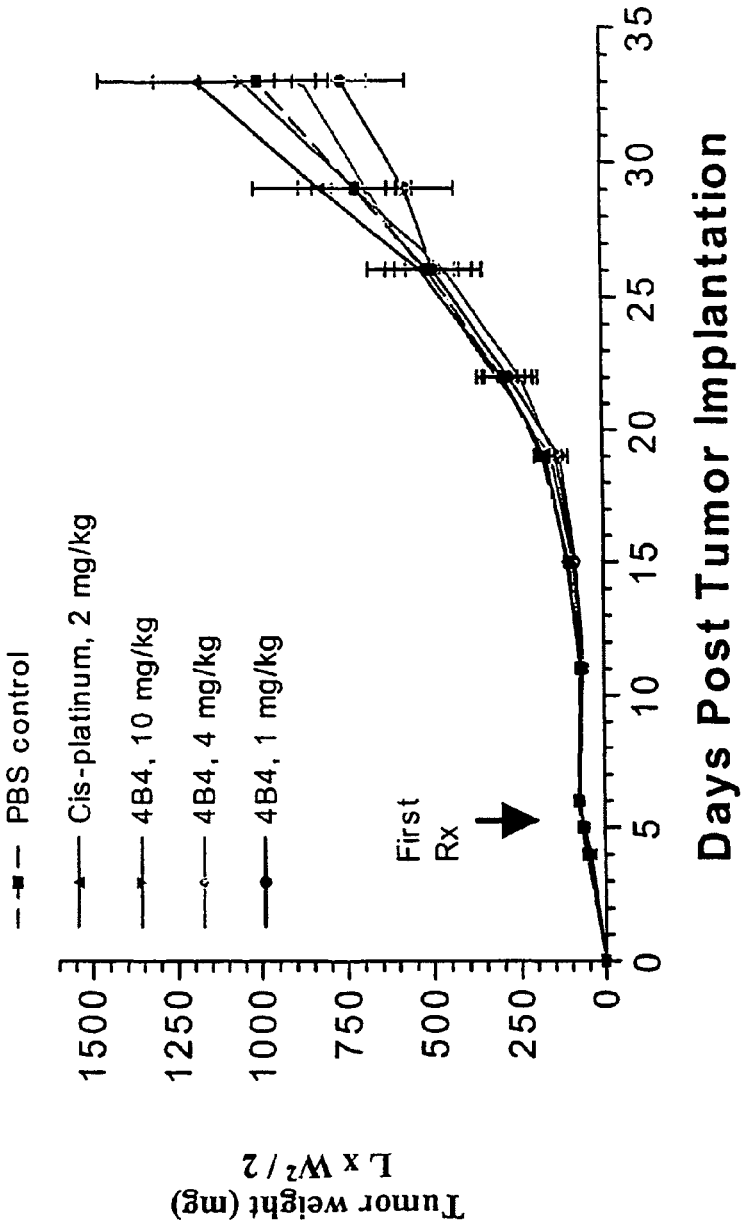

The right side of FIG. 12 shows $\alpha_v\beta_6$ expression on the different tumor cell lines as indicated by 6.3G9 binding in fluorescence activated cell sorting (FACS). The solid peak represents 6.3G9 binding while the open peak represents background binding of the secondary mAb alone. The line graph on the left side of FIG. 12 shows inhibition of the tumor cell lines' binding to the LAP ligand by increasing concentrations of 6.3G9 or 6.4B4. 6.4B4 was a significantly less potent inhibitor of $\alpha_v\beta_6$ binding to LAP, compared to 6.3G9 (>10-fold $IC_{50}$ for Detroit 562, >30-fold $IC_{50}$ for SW480B6, and >100-fold $IC_{50}$ for SCC-14). This is consistent with previous in vitro results indicating that 6.3G9 is a potent blocking mAb and 6.4B4 is a weak blocking mAb. This data is also consistent with negligible inhibitory activity of 6.4B4 in the Detroit xenograft model (FIG. 14B). FIG. 13 further shows the relative inhibition of tumor cell lines' binding to LAP by various anti-$\alpha_v\beta_6$ mAbs. Both 6.3G9 and 6.8G6 displayed equivalent inhibiting activity (consistent with all previous data) while 6.4B4 was a significantly less potent inhibitor of $\alpha_v\beta_6$ binding to LAP.

Example 18

Effects of anti-$\alpha_v\beta_6$ Blocking mAbs in a Human Tumor Xenograft Model Immunodeficient animals (e.g., nude mice and SCID mice) transplanted with human tumor xenografts have been established as a useful in vivo model system to test the therapeutic effects of anti-cancer agents (see, e.g., van Weerden et al., *Prostate* 43(4):263-71 (2000); Bankert et al., *Front Biosci* 7:c44-62 (2002)). Thus, the blocking anti-$\alpha_v\beta_6$ monoclonal antibodies of the present invention can be tested in vivo in a xenograft model for their ability to inhibit tumor growth. In this experiment, we tested the ability of some of the new $\alpha_v\beta_6$ antibodies to inhibit tumor growth in athymic nude female mice transplanted with cancerous human pharyngeal (Detroit 562 cell line) xenograft.

To do this, Detroit 562 cells (ATCC) were passed in vitro in Minimum essential medium (Eagle) with 2 mM L-glutamine and Earle's BSS adjusted to contain 1.5 g/L sodium bicarbonate, 0.1 mM nonessential amino acids, and 1.0 mM sodium pyruvate, and 10% fetal bovine serum, without antibiotics. About $5 \times 10^6$ cells/0.2 ml media (without serum) were implanted subcutaneously into nude mice on the right flank. Three to four days later, tumor size measurements were started and continued until the tumors were about 5 mm (length) by 5 mm (width). The mice were randomized and injected intraperitoneally with the test antibodies or control solutions on day 1, followed by three injections weekly for a period of 33 days. The test antibodies and control solutions were: (1) 6.3G9, 1 mg/kg, 10 mice; (2) 6.3G9, 4 mg/kg, 10 mice; (3) 6.3G9, 10 mg/kg, 10 mice; (4) 6.4B4, 1 mg/kg, 10 mice; (5) 6.4B4, 4 mg/kg, 10 mice; (6) 6.4B4, 10 mg/kg, 10 mice; and (7) vehicle control (PBS), 0.2 ml/per mouse, 30 mice. In addition, cis-platinum was injected into 10 mice subcutaneously at 2 mg/kg as a chemotherapeutical control. The cis-platinum injections were done on day 1 and then every 2 days for a total of six treatments. At the end of the 33 day period, animal weights and tumor sizes were measured, $\alpha_v\beta_6$ expression assessed by immunohistology, and serum anti-$\alpha_v\beta_6$ levels measured.

Immunohistological staining showed that the implanted tumor cells strongly expressed $\alpha_v\beta_6$ in vivo. Tumor weight data further showed that blocking mAb 6.3G9 effectively inhibited tumor growth at all three concentrations tested (FIG. 14A). In contrast, weak blocking mAb 6.4B4 did not inhibit tumor growth (FIG. 14B).

In sum, blocking antibodies inhibited tumor growth by 40-50% in the treated mice. In contrast, a weak blocking anti-$\alpha_v\beta_6$ antibody did not inhibit tumor growth.

Example 19

$\alpha_v\beta_6$ Antibody Internalization

Antibodies that are internalized by cells offer an advantage for certain clinical indications such as cancer, because the antibodies can then be conjugated with toxins, radioactive compounds or other anti-cancer agents to selectively target and inhibit growth of cancer cells. The ability of anti-$\alpha_v\beta_6$ antibodies to be internalized was studied in SW480B6 (supra) and SCC-14 cells.

Cells were split 1:5 and plated onto 4-chambered glass slides for overnight incubation at 37° C., 5% $CO_2$. The next day, mAbs 6.8G6, 6.1A8, 6.3G9, 7.1C5, 6.4B4, 10D5, and 8B3 were diluted to a final concentration of 20 μg/mL. The mAbs or medium alone were added to appropriate wells. A time course of internalization was run from 0 h to 48 h. Time points included were 0, 5, 10 and 30 min, and 1, 4, 24 and 48 h. A secondary antibody (anti-murine-Alexa 594) was added as a negative control. Internalization was stopped at each time point by removing the antibody and washing the cell layer with buffer. Wheat Germ Agglutinin-Alexa-488 was added for 20 min at 18° C. to stain the outer edge of the cells with green fluorescence. After the cells were washed, Cytofix/Cytoperm solution was added for 20 min at 18° C. to fix and permeabilize the cells. The cells were washed again and the secondary anti-mouse-Alexa 594 (red fluorescence) was added for 20 min at 18° C. to label the bound or internalized murine $\alpha_v\beta_6$ antibody. The cells were then washed and fixed by addition of 2% paraformaldehyde and examined by confocal microscopy. Images were then taken with a Leitz Plan-Apochromatic 63x (1.32 numerical aperture, ail immersion) objective (Leica) with a 2× digital zoom. Each frame represented a single optical section from the middle section of the cells observed for internalization under all conditions. There was no staining observed in the nucleus.

Internalization was observed for cation-dependent mAbs (RGD-containing ligand mimetics) such as 6.8G6 and 6.1A8. No internalization was observed for cation-independent mAbs such as 6.3G9, 7.1C5, and 6.4B4.

What is claimed is:

1. A method for treating a subject having or at risk of having a fibrosis disease mediated by αvβ6, comprising administering to the subject a composition comprising
a monoclonal antibody that is an αvβ6 blocking antibody, or an antigen binding fragment thereof and a pharmaceutically acceptable carrier;
thereby alleviating, or postponing the onset of, the fibrosis disease wherein the monoclonal antibody or antigen binding fragment in said composition is selected from the group consisting of:
(a) an antibody or an antigen binding fragment of an antibody that comprises the same heavy and light chain polypeptide sequences as an antibody produced by hybridoma 6.1A8 (ATCC accession number PTA-3647);
(b) an antibody that comprises the same heavy and light chain polypeptide sequences as an antibody produced by hybridoma 6.3G9 (ATCC accession number PTA-3649);
(c) an antibody or an antigen binding fragment of an antibody that comprises the same heavy and light chain polypeptide sequences as an antibody produced by hybridoma 6.8G6 (ATCC accession number PTA-3645);
(d) an antibody or an antigen binding fragment of an antibody that comprises the same heavy and light chain polypeptide sequences as an antibody produced by hybridoma 6.2B1 (ATCC accession number PTA-3646);
(e) an antibody or an antigen binding fragment of an antibody that comprises comprises the same heavy and light chain polypeptide sequences as an antibody produced by hybridoma 7.1G10 (ATCC accession number PTA-3898);
(f) an antibody or an antigen binding fragment of an antibody that comprises the same heavy and light chain polypeptide sequences as an antibody produced by hybridoma 7.7G5 (ATCC accession number PTA-3899); and
(g) an antibody or an antigen binding fragment of an antibody that comprises the same heavy and light chain polypeptide sequences as an antibody produced by hybridoma 7.1 C5 (ATCC accession number PTA-3900).

2. The method of claim 1, wherein the subject is a human.

3. The method of claim 1, wherein the disease is fibrosis.

4. The method of claim 3, wherein the fibrosis is scleroderma, scarring, liver fibrosis, kidney fibrosis or lung fibrosis.

5. The method of claim 1 wherein the antibody in said composition is one in which the binding between the antibody and αvβ6 is divalent cation-independent.

6. The method of claim 1, wherein the antibody in said composition is selected from the group consisting of:
(a) an anti-αvβ6 antibody whose heavy chain complementarity determining regions (CDR) 1, 2 and 3 comprise the sequences of SEQ ID NOs:1, 4 and 7, respectively, and whose light chain CDRs 1, 2 and 3 comprise the sequences of SEQ ID NOs:10, 13 and 15, respectively;
(b) an anti-αvβ6 antibody whose heavy chain complementarity determining regions (CDR) 1, 2 and 3 comprise the sequences of SEQ ID NOs:3, 5 and 8, respectively, and whose light chain CDRs 1, 2 and 3 comprise the sequences of SEQ ID NOs:11, 14 and 17, respectively;
(c) an anti-αvβ6 antibody whose heavy chain complementarity determining regions (CDR) 1, 2 and 3 comprise the sequences of SEQ ID NOs:3, 6 and 9, respectively, and light chain CDRs 1, 2 and 3 comprise the sequences of SEQ ID NOs:12, 14 and 18, respectively;
(d) an anti-αvβ6 antibody whose heavy chain complementarity determining regions (CDR) 1, 2 and 3 comprise the sequences of SEQ ID NOs:2, 46 and 47, respectively, and whose light chain CDRs 1, 2 and 3 comprise the sequences of SEQ ID NOs:48, 13 and 16, respectively;
(e) an anti-αvβ6 antibody whose heavy chain complementarity determining regions (CDR) 1, 2 and 3 comprise the sequences of SEQ ID NOs:49, 51, and 53, respectively, and light chain CDRs 1, 2 and 3 comprise the sequences of SEQ ID NOs:55, 57 and 59, respectively;
(f) an anti-αv β6 antibody whose heavy chain complementarity determining regions (CDR) 1, 2 and 3 comprise the sequences of SEQ ID NOs:50, 52, and 54, respectively, and whose light chain CDRs 1, 2 and 3 comprise the sequences of SEQ ID NOs:56, 58 and 60, respectively;
(g) an anti-αvβ6 antibody comprising a heavy chain variable domain sequence of any one of SEQ ID NOs:19-36 or SEQ ID NOs 61-62;

(h) an anti-αvβ6 antibody or an antigen binding fragment thereof comprising a heavy chain variable domain sequence of SEQ ID NO:19 and the light chain variable domain sequence of SEQ ID NO:37;

(i) an anti-αvβ6 antibody or an antigen binding fragment thereof comprising a heavy chain variable domain sequence of SEQ ID NO:20 or 21, and the light chain variable domain sequence of SEQ ID NO:38;

(j) an anti-αvβ6 antibody or an antigen binding fragment thereof comprising a heavy chain variable domain sequence of SEQ ID NO:22 and the light chain variable domain sequence of SEQ ID NO:43;

(k) an anti-αvβ6 antibody or an antigen binding fragment thereof comprising a heavy chain variable domain sequence of SEQ ID NO:23 and the light chain variable domain sequence of SEQ ID NO:44;

(l) an anti-αvβ6 antibody or an antigen binding fragment thereof comprising a heavy chain variable domain sequence of SEQ ID NO:24 and the light chain variable domain sequence of SEQ ID NO:45;

(m) an anti-αvβ6 antibody or an antigen binding fragment thereof comprising a heavy chain variable domain sequence of SEQ ID NO:25 or 26 and the light chain variable domain sequence of SEQ ID NO:42;

(n) an anti-αvβ6 antibody or an antigen binding fragment thereof comprising a heavy chain variable domain sequence of SEQ ID NO:27, 28, or 29, and the light chain variable domain sequence of SEQ ID NO:39;

(o) an anti-αvβ6 antibody or an antigen binding fragment thereof comprising a heavy chain variable domain sequence of SEQ ID NO:34 or 35, and the light chain variable domain sequence of SEQ ID NO:40;

(p) an anti-αvβ6 antibody or an antigen binding fragment thereof comprising a heavy chain variable domain sequence of SEQ ID NO:36, and the light chain variable domain sequence of SEQ ID NO:41;

(q) an anti-αvβ6 antibody or an antigen binding fragment thereof comprising a heavy chain variable domain sequence of SEQ ID NO:61, and the light chain variable domain sequence of SEQ ID NO:63; and (r) an anti-αvβ6 antibody or an antigen binding fragment thereof comprising a heavy chain variable domain sequence of SEQ ID NO:62, and the light chain variable domain sequence of SEQ ID NO:64.

7. The method of claim 1, wherein the antibody is selected from the group consisting of:

an anti-αvβ6 antibody or an antigen binding fragment thereof which comprises the same heavy and light chain polypeptide sequences as an antibody produced by hybridoma 6.2A1 (ATCC accession number PTA-3896);

an anti-αvβ6 antibody or an antigen binding fragment thereof which comprises the same heavy and light chain polypeptide sequences as an antibody produced by hybridoma 6.2E5 (ATCC accession number PTA-3897);

an anti-αvβ6 antibody or an antigen binding fragment thereof which comprises the same heavy and light chain polypeptide sequences as an antibody produced by hybridoma 6.2B10 (ATCC accession number PTA-3648).

8. The method of composition of claim 1, wherein the antibody is conjugated to a cytotoxic agent.

9. The method of claim 1, wherein the antibody in said composition is an anti-αvβ6 antibody comprising an amino acid sequence of any one of SEQ ID NOs:19-45 and SEQ ID NOs 61-64.

10. The method of claim 1, wherein the antibody in said composition comprises heavy chain complementarity determining regions 1, 2, and 3 and light chain complementarity determining regions 1, 2, and 3 wherein the heavy chain complementarity determining regions (CDR) 1, 2 and 3 comprise SEQ ID NOs:3, 6 and 9, respectively and wherein the light chain CDRs comprise SEQ ID NOs:12, 14 and 18, respectively.

11. The method of claim 1, wherein said antibody in said composition is a monoclonal antibody that binds soluble αvβ6 but does not bind the β6 subunit.

12. The method of claim 1, wherein said monoclonal antibody in said composition prevents the activation of TGF-β.

13. The method of claim 1 wherein the antibody in said composition comprises heavy chain complementarity determining regions 1, 2, and 3 and light chain complementarity determining regions 1, 2, and 3, wherein said antibody competes with 6.8G6 (ATCC accession number PTA-3645) for binding to αvβ6 and contains an FXY motif in CDR3 of the heavy chain.

14. The method of claim 1, wherein said antibody in said composition contains a mutation at an amino acid residue that is a site for glycosylation such that the glycosylation site is eliminated.

15. The method of claim 1, wherein said composition comprises:

(a) an antibody produced by hybridoma 6.1A8 (ATCC accession number PTA-3647) or an antigen binding fragment of an antibody produced by hybridoma 6.1A8 (ATCC accession number PTA-3647); or (b) an antibody produced by hybridoma 6.2B10 (ATCC accession number PTA-3648) or an antigen binding fragment of an antibody produced by hybridoma 6.2B10 (ATCC accession number PTA-3648); or (c) an antibody produced by hybridoma 6.3G9 (ATCC accession number PTA-3649) or an antigen binding fragment of an antibody produced by hybridoma 6.3G9 (ATCC accession number PTA-3649); or (d) an antibody produced by hybridoma 6.8G6 (ATCC accession number PTA-3645) or an antigen binding fragment of an antibody produced by hybridoma 6.8G6 (ATCC accession number PTA-3645); or (e) an antibody produced by hybridoma 6.2B1 (ATCC accession number PTA-3646) or an antigen binding fragment of an antibody produced by hybridoma 6.2B1 (ATCC accession number PTA-3646); or (f) an antibody produced by hybridoma 6.2A1 (ATCC accession number PTA-3896) or an antigen binding fragment of an antibody produced by hybridoma 6.2A1 (ATCC accession number PTA-3896); or (g) an antibody produced by hybridoma 6.2E5 (ATCC accession number PTA-3897) or an antigen binding fragment of an antibody produced by hybridoma 6.2E5 (ATCC accession number PTA-3897); or (h) an antibody produced by hybridoma 7.1G10 (ATCC accession number PTA-3898) or an antigen binding fragment of an antibody produced by hybridoma 7.1G10 (ATCC accession number PTA-3898) or;

(i) an antibody produced by hybridoma 7.7G5 (ATCC accession number PTA-3899) or an antigen binding fragment of an antibody produced by hybridoma 7.7G5 (ATCC accession number PTA-3899); or (j) an antibody produced by hybridoma 7.1C5 (ATCC accession number PTA-3900) or an antigen binding fragment of an antibody produced by hybridoma 7.1C5 (ATCC accession number PTA-3900).

16. The method of claim 1, wherein the disease is acute lung injury.

* * * * *

SEQUENCE LISTING

```
<160> NUMBER OF SEQ ID NOS: 64

<210> SEQ ID NO 1
<211> LENGTH: 10
<212> TYPE: PRT
<213> ORGANISM: Homo sapiens

<400> SEQUENCE: 1

Ser Tyr Thr Phe Thr Asp Tyr Ala Met His
1               5                   10

<210> SEQ ID NO 2
<211> LENGTH: 10
<212> TYPE: PRT
<213> ORGANISM: Homo sapiens

<400> SEQUENCE: 2

Ser Tyr Thr Phe Thr Asp Tyr Thr Met His
1               5                   10

<210> SEQ ID NO 3
<211> LENGTH: 10
<212> TYPE: PRT
<213> ORGANISM: Homo sapiens

<400> SEQUENCE: 3

Gly Phe Thr Phe Ser Arg Tyr Val Met Ser
1               5                   10
```

```
<210> SEQ ID NO 4
<211> LENGTH: 17
<212> TYPE: PRT
<213> ORGANISM: Homo sapiens

<400> SEQUENCE: 4

Val Ile Ser Thr Tyr Tyr Gly Asn Thr Asn Tyr Asn Gln Lys Phe Lys
 1               5                  10                  15

Gly

<210> SEQ ID NO 5
<211> LENGTH: 16
<212> TYPE: PRT
<213> ORGANISM: Homo sapiens

<400> SEQUENCE: 5

Ser Ile Ser Ser Gly Gly Ser Thr Tyr Tyr Pro Asp Ser Val Lys Gly
 1               5                  10                  15

<210> SEQ ID NO 6
<211> LENGTH: 16
<212> TYPE: PRT
<213> ORGANISM: Homo sapiens

<400> SEQUENCE: 6

Ser Ile Ser Ser Gly Gly Arg Met Tyr Tyr Pro Asp Thr Val Lys Gly
 1               5                  10                  15

<210> SEQ ID NO 7
<211> LENGTH: 17
<212> TYPE: PRT
<213> ORGANISM: Homo sapiens
<220> FEATURE:
<221> NAME/KEY: MOD_RES
<222> LOCATION: (12)
<223> OTHER INFORMATION: Arg or Gln

<400> SEQUENCE: 7

Gly Gly Leu Arg Arg Gly Asp Arg Pro Ser Leu Xaa Tyr Ala Met Asp
 1               5                  10                  15

Tyr

<210> SEQ ID NO 8
<211> LENGTH: 12
<212> TYPE: PRT
<213> ORGANISM: Homo sapiens

<400> SEQUENCE: 8

Gly Ala Ile Tyr Asp Gly Tyr Tyr Val Phe Ala Tyr
 1               5                  10

<210> SEQ ID NO 9
<211> LENGTH: 12
<212> TYPE: PRT
<213> ORGANISM: Homo sapiens

<400> SEQUENCE: 9

Gly Ser Ile Tyr Asp Gly Tyr Tyr Val Phe Pro Tyr
 1               5                  10

<210> SEQ ID NO 10
<211> LENGTH: 15
<212> TYPE: PRT
<213> ORGANISM: Homo sapiens

<400> SEQUENCE: 10
```

Arg Ala Ser Gln Ser Val Ser Thr Ser Ser Tyr Ser Tyr Met Tyr
1               5                   10                  15

<210> SEQ ID NO 11
<211> LENGTH: 12
<212> TYPE: PRT
<213> ORGANISM: Homo sapiens

<400> SEQUENCE: 11

Ser Ala Ser Ser Ser Val Ser Ser Ser Tyr Leu Tyr
1               5                   10

<210> SEQ ID NO 12
<211> LENGTH: 12
<212> TYPE: PRT
<213> ORGANISM: Homo sapiens

<400> SEQUENCE: 12

Ser Ala Asn Ser Ser Val Ser Ser Ser Tyr Leu Tyr
1               5                   10

<210> SEQ ID NO 13
<211> LENGTH: 7
<212> TYPE: PRT
<213> ORGANISM: Homo sapiens

<400> SEQUENCE: 13

Tyr Ala Ser Asn Leu Glu Ser
1               5

<210> SEQ ID NO 14
<211> LENGTH: 7
<212> TYPE: PRT
<213> ORGANISM: Homo sapiens

<400> SEQUENCE: 14

Ser Thr Ser Asn Leu Ala Ser
1               5

<210> SEQ ID NO 15
<211> LENGTH: 9
<212> TYPE: PRT
<213> ORGANISM: Homo sapiens

<400> SEQUENCE: 15

Gln His Asn Trp Glu Ile Pro Phe Thr
1               5

<210> SEQ ID NO 16
<211> LENGTH: 9
<212> TYPE: PRT
<213> ORGANISM: Homo sapiens

<400> SEQUENCE: 16

Gln His Ser Trp Glu Ile Pro Tyr Thr
1               5

<210> SEQ ID NO 17
<211> LENGTH: 9
<212> TYPE: PRT
<213> ORGANISM: Homo sapiens

<400> SEQUENCE: 17

His Gln Trp Ser Ser Tyr Pro Pro Thr
1               5

```
<210> SEQ ID NO 18
<211> LENGTH: 9
<212> TYPE: PRT
<213> ORGANISM: Homo sapiens

<400> SEQUENCE: 18

His Gln Trp Ser Thr Tyr Pro Pro Thr
 1               5

<210> SEQ ID NO 19
<211> LENGTH: 126
<212> TYPE: PRT
<213> ORGANISM: Homo sapiens

<400> SEQUENCE: 19

Gln Val Gln Phe Gln Gln Ser Gly Pro Glu Leu Val Arg Pro Gly Val
 1               5                  10                  15

Ser Val Lys Leu Ser Cys Lys Gly Ser Ser Tyr Thr Phe Thr Asp Tyr
                20                  25                  30

Thr Met His Trp Val Lys Leu Ser His Ala Lys Thr Leu Glu Trp Ile
            35                  40                  45

Gly Val Ile Asp Thr Tyr Tyr Gly Lys Thr Asn Tyr Asn Gln Lys Phe
    50                  55                  60

Glu Gly Lys Ala Thr Met Thr Val Asp Lys Ser Ser Thr Ala Tyr
 65                  70                  75                  80

Met Asp Leu Ala Arg Leu Thr Ser Glu Asp Ser Ala Val Tyr Tyr Cys
                85                  90                  95

Ala Arg Gly Gly Phe Arg Arg Gly Asp Arg Pro Ser Leu Arg Tyr Ala
                100                 105                 110

Met Asp Ser Trp Gly Gln Gly Thr Ser Val Thr Val Ser Ser
            115                 120                 125

<210> SEQ ID NO 20
<211> LENGTH: 126
<212> TYPE: PRT
<213> ORGANISM: Homo sapiens

<400> SEQUENCE: 20

Gln Val Gln Leu Gln Gln Ser Gly Pro Glu Leu Val Arg Pro Gly Val
 1               5                  10                  15

Ser Val Lys Ile Ser Cys Lys Gly Ser Ser Tyr Thr Phe Thr Asp Tyr
                20                  25                  30

Ala Met His Trp Val Lys Leu Ser His Ala Lys Ser Leu Glu Trp Ile
            35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Lys Ser Ser Ser Thr Ala Tyr
 65                  70                  75                  80

Met Glu Leu Ala Arg Leu Thr Ser Glu Asp Ser Ala Val Tyr Tyr Cys
                85                  90                  95

Ala Arg Gly Gly Leu Arg Arg Gly Asp Arg Pro Ser Leu Arg Tyr Ala
                100                 105                 110

Met Asp Tyr Trp Gly Gln Gly Thr Ser Val Thr Val Ser Ser
            115                 120                 125

<210> SEQ ID NO 21
<211> LENGTH: 126
<212> TYPE: PRT
```

<213> ORGANISM: Homo sapiens

<400> SEQUENCE: 21

Gln Val Gln Leu Gln Gln Ser Gly Pro Glu Leu Val Arg Pro Gly Val
1               5                   10                  15

Ser Val Lys Ile Ser Cys Lys Gly Ser Ser Tyr Thr Phe Thr Asp Tyr
            20                  25                  30

Ala Met His Trp Val Lys Leu Ser His Ala Lys Ser Leu Glu Trp Ile
        35                  40                  45

Gly Val Ile Ser Thr Tyr Tyr Gly Asn Thr Asn Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Val Tyr Tyr Cys
                85                  90                  95

Ala Arg Gly Gly Leu Arg Arg Gly Asp Arg Pro Ser Leu Gln Tyr Ala
            100                 105                 110

Met Asp Tyr Trp Gly Gln Gly Thr Ser Val Thr Val Ser Ser
        115                 120                 125

<210> SEQ ID NO 22
<211> LENGTH: 119
<212> TYPE: PRT
<213> ORGANISM: Homo sapiens

<400> SEQUENCE: 22

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Met Gln Ser His Gly Lys Ser Leu Glu Trp Ile
        35                  40                  45

Gly Arg Ile Lys Pro Tyr Asn Gly Asp Asn Phe Tyr Asn Gln Lys Phe
    50                  55                  60

Met Gly Lys Ala Thr Leu Thr Val Asp Lys Ser Ser Ser Thr Val His
65                  70                  75                  80

Met Glu Leu Arg Ser Leu Ala Ser Glu Asp Ser Ala Val Tyr Tyr Cys
                85                  90                  95

Ala Arg Asp Arg Tyr Gly Thr Tyr Gly Met Asp Tyr Trp Gly Gln Gly
            100                 105                 110

Thr Ser Val Thr Val Ser Ser
        115

<210> SEQ ID NO 23
<211> LENGTH: 120
<212> TYPE: PRT
<213> ORGANISM: Homo sapiens

<400> SEQUENCE: 23

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Val Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

```
Gly Arg Phe Thr Ile Ser Arg Asp Ser Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Gly Ala Ile Tyr Asp Gly Tyr Tyr Val Phe Ala Tyr Trp Gly Gln
            100                 105                 110

Gly Thr Leu Val Thr Val Ser Ala
        115                 120

<210> SEQ ID NO 24
<211> LENGTH: 120
<212> TYPE: PRT
<213> ORGANISM: Homo sapiens

<400> SEQUENCE: 24

Glu Val Met Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Arg Tyr
                20                  25                  30

Val Met Ser Trp Val Arg Gln Thr Pro Glu Lys Arg Leu Glu Trp Val
            35                  40                  45

Ala Ser Ile Ser Ser Gly Gly Arg Met Tyr Tyr Pro Asp Thr Val Lys
        50                  55                  60

Gly Arg Phe Thr Ile Ser Arg Asp Ser Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Gly Ser Ile Tyr Asp Gly Tyr Tyr Val Phe Pro Tyr Trp Gly Gln
            100                 105                 110

Gly Thr Leu Val Thr Val Ser Ala
        115                 120

<210> SEQ ID NO 25
<211> LENGTH: 121
<212> TYPE: PRT
<213> ORGANISM: Homo sapiens

<400> SEQUENCE: 25

Gln Val Gln Leu Gln Gln Pro Gly Ala Glu Leu Val Arg Pro Gly Thr
 1               5                  10                  15

Ser Val Lys Leu Ser Cys Lys Ala Ser Gly Tyr Ser Phe Thr Ser Tyr
                20                  25                  30

Trp Met Asn Trp Val Lys Gln Arg Pro Gly Gln Gly Leu Glu Trp Ile
            35                  40                  45

Gly Met Ile His Pro Ser Ile Ser Glu Thr Arg Leu Asn Pro Lys Phe
        50                  55                  60

Lys Asp Lys Ala Thr Leu Thr Val Asp Thr Ser Ser Ser Thr Val Tyr
 65                  70                  75                  80

Met Gln Leu Ser Ser Pro Thr Ser Glu Asp Ser Ala Val Tyr Tyr Cys
                 85                  90                  95

Ala Arg Tyr Leu Gly Tyr Tyr Thr Tyr Tyr Gly Ser Asp Cys Trp Gly
            100                 105                 110

Gln Gly Thr Ser Val Thr Val Ser Ser
        115                 120

<210> SEQ ID NO 26
<211> LENGTH: 121
<212> TYPE: PRT
```

<213> ORGANISM: Homo sapiens

<400> SEQUENCE: 26

```
Gln Val Gln Leu Gln Gln Pro Gly Ala Glu Leu Val Pro Gly Thr
 1               5                  10                  15
Ser Val Lys Leu Ser Cys Lys Ala Ser Gly Tyr Ser Phe Thr Ser Tyr
                20                  25                  30
Trp Met Asn Trp Val Lys Gln Arg Pro Gly Gln Gly Leu Glu Trp Ile
            35                  40                  45
Gly Met Ile His Pro Ser Ile Ser Glu Thr Arg Leu Asn Pro Lys Phe
        50                  55                  60
Lys Asp Lys Ala Thr Leu Thr Val Asp Thr Ser Ser Thr Val Tyr
 65                  70                  75                  80
Met Gln Leu Ser Ser Pro Thr Ser Glu Asp Ser Ala Val Tyr Tyr Cys
                85                  90                  95
Ala Arg Tyr Leu Gly Tyr Tyr Thr Tyr Tyr Gly Leu Asp Tyr Trp Gly
            100                 105                 110
Gln Gly Thr Ser Val Thr Val Ser Ser
        115                 120
```

<210> SEQ ID NO 27
<211> LENGTH: 119
<212> TYPE: PRT
<213> ORGANISM: Homo sapiens

<400> SEQUENCE: 27

```
Gln Val Gln Leu Gln Gln Ser Gly Ala Val Leu Met Lys Pro Gly Ala
 1               5                  10                  15
Ser Val Lys Ile Ser Cys Lys Ala Thr Gly Tyr Ser Phe Thr Asn Tyr
                20                  25                  30
Trp Ile Asp Trp Ile Lys Gln Arg Pro Gly His Gly Leu Glu Trp Ile
            35                  40                  45
Gly Glu Asn Leu Pro Gly Thr Arg Asn Asn Tyr Asn Glu Asn Phe Lys
        50                  55                  60
Gly Lys Ala Thr Phe Thr Ala Asp Pro Ser Ser Asn Thr Ala Tyr Ile
 65                  70                  75                  80
Gln Leu Asn Ser Leu Thr Ser Asp Asp Ser Ala Val Tyr Tyr Cys Ala
                85                  90                  95
Arg Glu Ala Leu Gly Gly Asp Tyr Gly Leu Asp Tyr Trp Gly Gln Gly
            100                 105                 110
Thr Ser Leu Thr Val Ser Ser
        115
```

<210> SEQ ID NO 28
<211> LENGTH: 119
<212> TYPE: PRT
<213> ORGANISM: Homo sapiens

<400> SEQUENCE: 28

```
Gln Val Gln Leu Gln Gln Ser Gly Ala Val Leu Met Lys Pro Gly Ala
 1               5                  10                  15
Ser Val Lys Ile Ser Cys Lys Ala Thr Gly Tyr Ser Phe Thr Asn Tyr
                20                  25                  30
Trp Ile Asp Trp Ile Lys Gln Arg Pro Gly His Gly Leu Glu Trp Ile
            35                  40                  45
Gly Glu Asn Leu Pro Gly Thr Arg Asn Asn Tyr Asn Glu Asn Phe Lys
        50                  55                  60
```

-continued

Gly Lys Ala Thr Phe Thr Ala Asp Pro Ser Ser Asn Thr Ala Tyr Ile
65                  70                  75                  80

Gln Leu Asn Ser Leu Thr Ser Asp Asp Ser Ala Val Tyr Tyr Cys Ala
            85                  90                  95

Arg Glu Ala Leu Gly Gly Asp Tyr Val Leu Asp Tyr Trp Gly Gln Gly
        100                 105                 110

Thr Ser Leu Thr Val Ser Ser
        115

<210> SEQ ID NO 29
<211> LENGTH: 119
<212> TYPE: PRT
<213> ORGANISM: Homo sapiens

<400> SEQUENCE: 29

Gln Val Gln Leu Gln Gln Ser Gly Ala Val Leu Met Lys Pro Gly Ala
1               5                   10                  15

Ser Val Lys Ile Ser Cys Lys Ala Thr Gly Tyr Ser Phe Thr Asn Tyr
            20                  25                  30

Trp Met Asp Trp Ile Lys Gln Arg Pro Gly His Gly Leu Glu Trp Ile
        35                  40                  45

Gly Glu Asn Leu Pro Gly Thr Arg Asn Asn Tyr Asn Glu Asn Phe Lys
    50                  55                  60

Gly Arg Ala Thr Phe Thr Ala Asp Pro Ser Ser Asn Thr Ala Tyr Ile
65                  70                  75                  80

Gln Leu Asn Ser Leu Thr Ser Asp Asp Ser Ala Val Tyr Tyr Cys Ala
            85                  90                  95

Arg Glu Ala Leu Gly Gly Asp Tyr Gly Leu Asp Tyr Trp Gly Gln Gly
        100                 105                 110

Thr Ser Leu Thr Val Ser Ser
        115

<210> SEQ ID NO 30
<211> LENGTH: 118
<212> TYPE: PRT
<213> ORGANISM: Homo sapiens

<400> SEQUENCE: 30

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Ile Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg His Val Leu Ser Gly Asn Phe Asp Tyr Trp Gly Gln Gly Thr
        100                 105                 110

Thr Leu Thr Val Ser Ser
        115

<210> SEQ ID NO 31
<211> LENGTH: 118
<212> TYPE: PRT

<213> ORGANISM: Homo sapiens

<400> SEQUENCE: 31

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Ile Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg His Val Leu Ser Gly Asn Phe Asp Tyr Trp Gly Gln Gly Thr
            100                 105                 110

Thr Leu Thr Val Ser Ser
        115

<210> SEQ ID NO 32
<211> LENGTH: 118
<212> TYPE: PRT
<213> ORGANISM: Homo sapiens

<400> SEQUENCE: 32

Gln Val Gln Leu Gln Gln Ser Arg Pro Glu Leu Val Lys Pro Gly Ala
1               5                   10                  15

Ser Val Arg Ile Ser Cys Lys Ala Ser Gly Tyr Ile Phe Thr Ser Tyr
            20                  25                  30

Tyr Leu His Trp Val Lys Gln Arg Pro Gly Gln Gly Leu Glu Trp Ile
        35                  40                  45

Gly Trp Ile Tyr Pro Gly Asn Gly Asn Thr Lys Tyr Asn Glu Lys Phe
    50                  55                  60

Lys Asp Lys Ala Thr Leu Thr Ser Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg His Val Leu Ser Gly Asn Phe Asp Tyr Trp Gly Gln Gly Thr
            100                 105                 110

Thr Leu Thr Val Ser Ser
        115

<210> SEQ ID NO 33
<211> LENGTH: 118
<212> TYPE: PRT
<213> ORGANISM: Homo sapiens

<400> SEQUENCE: 33

Gln Val Gln Leu Gln Gln Ser Arg Pro Glu Leu Val Lys Pro Gly Ala
1               5                   10                  15

Ser Val Arg Ile Ser Cys Lys Ala Ser Gly Tyr Ile Phe Thr Ser Tyr
            20                  25                  30

Tyr Leu His Trp Val Lys Gln Arg Pro Gly Gln Gly Leu Glu Trp Ile
        35                  40                  45

Gly Trp Ile Tyr Pro Gly Asn Gly Asn Thr Lys Tyr Ser Glu Lys Phe
    50                  55                  60

```
Lys Asp Lys Ala Thr Leu Thr Ser Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg His Val Leu Ser Gly Asn Phe Asp Tyr Trp Gly Gln Gly Thr
            100                 105                 110

Thr Leu Thr Val Ser Ser
        115

<210> SEQ ID NO 34
<211> LENGTH: 118
<212> TYPE: PRT
<213> ORGANISM: Homo sapiens

<400> SEQUENCE: 34

Gln Leu Gln Val Gln Leu Gln Gln Ser Gly Pro Glu Leu Val Lys Pro
  1               5                  10                  15

Gly Ala Ser Leu Arg Ile Ser Cys Lys Ala Ser Gly Tyr Thr Phe Lys
             20                  25                  30

Ser Tyr Tyr Ile His Trp Val Arg Gln Arg Pro Gly Gln Gly Leu Glu
         35                  40                  45

Trp Ile Gly Trp Ile Tyr Pro Gly Asn Leu Asn Thr Lys Tyr Asn Glu
 50                  55                  60

Lys Phe Lys Gly Lys Ala Thr Leu Thr Ala Asp Lys Ser Ser Ser Thr
 65                  70                  75                  80

Val Tyr Met Ser Ser Leu Thr Ser Glu Asp Ser Ala Val Tyr Phe Cys
                 85                  90                  95

Ala Arg His Glu Leu Asn Gly Asn Phe Asp Tyr Trp Gly Gln Gly Thr
            100                 105                 110

Thr Leu Thr Val Ser Ser
        115

<210> SEQ ID NO 35
<211> LENGTH: 118
<212> TYPE: PRT
<213> ORGANISM: Homo sapiens

<400> SEQUENCE: 35

Gln Val Gln Leu Gln Gln Ser Gly Pro Glu Leu Val Lys Pro Gly Ala
  1               5                  10                  15

Ser Leu Arg Ile Ser Cys Lys Ala Ser Gly Tyr Thr Glu Lys Ser Tyr
             20                  25                  30

Tyr Ile His Trp Val Arg Gln Arg Pro Gly Gln Gly Leu Glu Trp Ile
         35                  40                  45

Gly Trp Ile Tyr Pro Gly Asn Pro Asn Thr Lys Tyr Asn Glu Lys Phe
 50                  55                  60

Lys Gly Lys Ala Thr Leu Thr Ala Asp Lys Ser Ser Ser Thr Val Tyr
 65                  70                  75                  80

Met Gln Leu Ser Ser Leu Thr Ser Glu Asp Ser Ala Val Tyr Phe Cys
                 85                  90                  95

Ala Arg His Glu Leu Asn Gly Asn Phe Asp Tyr Trp Gly Gln Gly Thr
            100                 105                 110

Thr Leu Thr Val Ser Ser
        115

<210> SEQ ID NO 36
<211> LENGTH: 118
<212> TYPE: PRT
```

<213> ORGANISM: Homo sapiens

<400> SEQUENCE: 36

Gln Val Gln Leu Gln Gln Ser Gly Pro Glu Leu Val Lys Pro Gly Ala
 1               5                  10                  15

Ser Val Arg Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Leu Tyr Pro Gly Lys Ile Asn Thr Arg Tyr Asn Glu Lys Phe
    50                  55                  60

Lys Gly Lys Ala Thr Leu Ile Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg His Val Leu Asn Gly Asn Phe Asp Tyr Trp Gly Gln Gly Thr
            100                 105                 110

Thr Leu Thr Val Ser Ser
        115

<210> SEQ ID NO 37
<211> LENGTH: 111
<212> TYPE: PRT
<213> ORGANISM: Homo sapiens

<400> SEQUENCE: 37

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Ile Ser
            20                  25                  30

Thr Tyr Ser Tyr Ile His Trp Phe Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Ile Tyr Tyr Cys Gln His Ser Trp
                85                  90                  95

Glu Ile Pro Tyr Thr Phe Gly Gly Gly Thr Lys Val Glu Ile Lys
            100                 105                 110

<210> SEQ ID NO 38
<211> LENGTH: 111
<212> TYPE: PRT
<213> ORGANISM: Homo sapiens

<400> SEQUENCE: 38

Asp Ile Val Leu Thr Gln Ser Pro Ala Ser Leu Ala Val Ser Leu Gly
 1               5                  10                  15

Gln Arg Ala Ile Ile Ser Cys Arg Ala Ser Gln Ser Val Ser Thr Ser
            20                  25                  30

Ser Tyr Ser Tyr Met Tyr Trp Tyr Gln Gln Lys Pro Gly Gln Ser Pro
        35                  40                  45

Lys Phe Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

```
Pro Val Glu Glu Asp Thr Ala Thr Tyr Tyr Cys Gln His Asn Trp
            85                  90                  95

Glu Ile Pro Phe Thr Phe Gly Gly Gly Thr Lys Leu Glu Ile Lys
        100                 105                 110
```

<210> SEQ ID NO 39
<211> LENGTH: 112
<212> TYPE: PRT
<213> ORGANISM: Homo sapiens

<400> SEQUENCE: 39

```
Asp Val Val Met Thr Gln Thr Pro Arg Ser Leu Pro Val Ser Leu
 1               5                  10                  15

Asp Gln Ala Ser Met Ser Cys Arg Ser Gln Ser Leu Lys His Ser
             20                  25                  30

Asn Gly Asp Thr Tyr Leu His Trp Tyr Leu Gln Lys Pro Gly Gln Ser
         35                  40                  45

Pro Asn Leu Leu Ile Tyr Lys Val Ser Asn Arg Phe Ser Gly Val Pro
 50                  55                  60

Asp Arg Phe Ser Gly Ser Gly Ser Gly Thr Glu Phe Thr Phe Lys Ile
 65                  70                  75                  80

Ser Arg Val Glu Ala Glu Asp Leu Gly Val Tyr Phe Cys Gln Ser
             85                  90                  95

Thr His Val Pro Tyr Thr Phe Gly Gly Gly Thr Arg Leu Glu Ile Lys
        100                 105                 110
```

<210> SEQ ID NO 40
<211> LENGTH: 107
<212> TYPE: PRT
<213> ORGANISM: Homo sapiens

<400> SEQUENCE: 40

```
Asp Ile Gln Met Thr Gln Ser Pro Ser Ser Leu Ser Ala Ser Leu Gly
 1               5                  10                  15

Glu Arg Val Asn Leu Thr Cys Arg Ala Ser Gln Glu Ile Ser Gly Tyr
             20                  25                  30

Leu Ser Trp Leu Gln Gln Lys Pro Asp Gly Thr Ile Lys Arg Leu Ile
         35                  40                  45

Tyr Ala Ala Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
 65                  70                  75                  80

Glu Asp Phe Gly Asp Tyr Tyr Cys Leu Gln Tyr Ala Ser Tyr Pro Tyr
             85                  90                  95

Thr Phe Gly Gly Gly Ala Lys Leu Glu Ile Lys
        100                 105
```

<210> SEQ ID NO 41
<211> LENGTH: 107
<212> TYPE: PRT
<213> ORGANISM: Homo sapiens

<400> SEQUENCE: 41

```
Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Glu Ile Ser Gly Tyr
             20                  25                  30

Leu Ser Trp Leu Gln Gln Lys Pro Asp Gly Ser Ile Lys Arg Leu Ile
         35                  40                  45
```

```
Tyr Ala Ala Ser Thr Leu Asp Ser Gly Val Pro Lys Arg Phe Ser Gly
            50                  55                  60

Ser Arg Ser Gly Ala Asp Tyr Ser Leu Thr Ile Ser Ser Leu Glu Ser
 65                  70                  75                  80

Glu Asp Phe Ala Asp Tyr Tyr Cys Leu Gln Tyr Ala Thr Tyr Pro Tyr
                 85                  90                  95

Thr Phe Gly Gly Gly Thr Lys Leu Glu Ile Lys
                100                 105
```

<210> SEQ ID NO 42
<211> LENGTH: 106
<212> TYPE: PRT
<213> ORGANISM: Homo sapiens

<400> SEQUENCE: 42

```
Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
                 20                  25                  30

His Trp Tyr Gln Gln Lys Ser Gly Thr Ser Pro Arg Arg Trp Ile Tyr
             35                  40                  45

Asp Thr Ser Lys Leu Ala Ser Gly Val Pro Ala Arg Phe Ser Gly Ser
         50                  55                  60

Gly Ser Gly Thr Ser Tyr Ser Leu Thr Ile Ser Ser Met Glu Ala Val
 65                  70                  75                  80

Asp Ala Ala Thr Tyr Tyr Cys Gln Gln Trp Thr Ser Asn Pro Phe Thr
                 85                  90                  95

Phe Gly Ser Gly Thr Lys Leu Gly Ile Lys
                100                 105
```

<210> SEQ ID NO 43
<211> LENGTH: 106
<212> TYPE: PRT
<213> ORGANISM: Homo sapiens

<400> SEQUENCE: 43

```
Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Thr Ser Lys Leu Ala Ser Gly Val Pro Thr Arg Phe Ser Gly Ser
         50                  55                  60

Gly Ser Gly Thr Ser Tyr Ser Leu Thr Ile Asn Ser Met Glu Ala Glu
 65                  70                  75                  80

Asp Ala Ala Thr Tyr Tyr Cys Gln Gln Trp Ser Ser His Pro Pro Thr
                 85                  90                  95

Phe Gly Ala Gly Thr Lys Leu Glu Leu Lys
                100                 105
```

<210> SEQ ID NO 44
<211> LENGTH: 108
<212> TYPE: PRT
<213> ORGANISM: Homo sapiens

<400> SEQUENCE: 44

```
Gln Ile Val Leu Thr Gln Ser Pro Ala Ile Met Ser Ala Ser Pro Gly
```

```
                1               5                  10                  15
Glu Lys Val Thr Leu Thr Cys Ser Ala Ser Ser Val Ser Ser
                20                  25                  30

Tyr Leu Tyr Trp Tyr Gln Gln Lys Pro Gly Ser Ser Pro Lys Leu Trp
                35                  40                  45

Ile Tyr Ser Thr Ser Asn Leu Ala Ser Arg Val Pro Ala Arg Phe Ser
                50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                    85                  90                  95

Pro Thr Phe Gly Gly Gly Thr Lys Leu Glu Ile Lys
                100                 105

<210> SEQ ID NO 45
<211> LENGTH: 108
<212> TYPE: PRT
<213> ORGANISM: Homo sapiens

<400> SEQUENCE: 45

Gln Ile Val Leu Thr Gln Ser Pro Ala Ile Met Ser Ala Ser Pro Gly
 1               5                  10                  15

Glu Lys Val Thr Leu Thr Cys Ser Ala Asn Ser Ser Val Ser Ser
                20                  25                  30

Tyr Leu Tyr Trp Tyr Gln Gln Lys Ser Gly Ser Ser Pro Lys Leu Trp
                35                  40                  45

Ile Tyr Ser Thr Ser Asn Leu Ala Ser Gly Val Pro Val Arg Phe Ser
                50                  55                  60

Gly Ser Gly Ser Gly Thr Ser Phe Ser Leu Thr Ile Ser Ser Met Glu
 65                  70                  75                  80

Ala Glu Asp Ala Ala Ser Tyr Phe Cys His Gln Trp Ser Thr Tyr Pro
                    85                  90                  95

Pro Thr Phe Gly Gly Gly Thr Lys Leu Glu Ile Lys
                100                 105

<210> SEQ ID NO 46
<211> LENGTH: 17
<212> TYPE: PRT
<213> ORGANISM: Homo sapiens

<400> SEQUENCE: 46

Val Ile Asp Thr Tyr Tyr Gly Lys Thr Asn Tyr Asn Gln Lys Phe Glu
 1               5                  10                  15

Gly

<210> SEQ ID NO 47
<211> LENGTH: 17
<212> TYPE: PRT
<213> ORGANISM: Homo sapiens

<400> SEQUENCE: 47

Gly Gly Phe Arg Arg Gly Asp Arg Pro Ser Leu Arg Tyr Ala Met Asp
 1               5                  10                  15

Ser

<210> SEQ ID NO 48
<211> LENGTH: 15
<212> TYPE: PRT
<213> ORGANISM: Homo sapiens
```

<400> SEQUENCE: 48

Arg Ala Ser Gln Ser Val Ser Ile Ser Thr Tyr Ser Tyr Ile His
1               5                   10                  15

<210> SEQ ID NO 49
<211> LENGTH: 10
<212> TYPE: PRT
<213> ORGANISM: Homo sapiens

<400> SEQUENCE: 49

Gly Tyr Asp Phe Asn Asn Asp Leu Ile Glu
1               5                   10

<210> SEQ ID NO 50
<211> LENGTH: 10
<212> TYPE: PRT
<213> ORGANISM: Homo sapiens

<400> SEQUENCE: 50

Gly Tyr Ala Phe Thr Asn Tyr Leu Ile Glu
1               5                   10

<210> SEQ ID NO 51
<211> LENGTH: 17
<212> TYPE: PRT
<213> ORGANISM: Homo sapiens

<400> SEQUENCE: 51

Val Ile Asn Pro Gly Ser Gly Arg Thr Asn Tyr Asn Glu Lys Phe Lys
1               5                   10                  15

Gly

<210> SEQ ID NO 52
<211> LENGTH: 17
<212> TYPE: PRT
<213> ORGANISM: Homo sapiens

<400> SEQUENCE: 52

Val Ile Ser Pro Gly Ser Gly Ile Ile Asn Tyr Asn Glu Lys Phe Lys
1               5                   10                  15

Gly

<210> SEQ ID NO 53
<211> LENGTH: 12
<212> TYPE: PRT
<213> ORGANISM: Homo sapiens

<400> SEQUENCE: 53

Ile Tyr Tyr Gly Pro His Ser Tyr Ala Met Asp Tyr
1               5                   10

<210> SEQ ID NO 54
<211> LENGTH: 11
<212> TYPE: PRT
<213> ORGANISM: Homo sapiens

<400> SEQUENCE: 54

Ile Asp Tyr Ser Gly Pro Tyr Ala Val Asp Asp
1               5                   10

<210> SEQ ID NO 55
<211> LENGTH: 11
<212> TYPE: PRT

<213> ORGANISM: Homo sapiens

<400> SEQUENCE: 55

Lys Ala Ser Leu Asp Val Arg Thr Ala Val Ala
1               5                   10

<210> SEQ ID NO 56
<211> LENGTH: 11
<212> TYPE: PRT
<213> ORGANISM: Homo sapiens

<400> SEQUENCE: 56

Lys Ala Ser Gln Ala Val Asn Thr Ala Val Ala
1               5                   10

<210> SEQ ID NO 57
<211> LENGTH: 7
<212> TYPE: PRT
<213> ORGANISM: Homo sapiens

<400> SEQUENCE: 57

Ser Ala Ser Tyr Arg Tyr Thr
1               5

<210> SEQ ID NO 58
<211> LENGTH: 7
<212> TYPE: PRT
<213> ORGANISM: Homo sapiens

<400> SEQUENCE: 58

Ser Ala Ser Tyr Gln Tyr Thr
1               5

<210> SEQ ID NO 59
<211> LENGTH: 9
<212> TYPE: PRT
<213> ORGANISM: Homo sapiens

<400> SEQUENCE: 59

Gln Gln His Tyr Gly Ile Pro Trp Thr
1               5

<210> SEQ ID NO 60
<211> LENGTH: 9
<212> TYPE: PRT
<213> ORGANISM: Homo sapiens

<400> SEQUENCE: 60

Gln His His Tyr Gly Val Pro Trp Thr
1               5

<210> SEQ ID NO 61
<211> LENGTH: 120
<212> TYPE: PRT
<213> ORGANISM: Homo sapiens

<400> SEQUENCE: 61

Gln Val Gln Leu Gln Gln Ser Gly Ala Glu Leu Ala Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
        35                  40                  45

Gly Val Ile Ser Pro Gly Ser Gly Ile Ile Asn Tyr Asn Glu Lys Phe

```
                50                  55                  60
Lys Gly Lys Ala Thr Leu Thr Ala Asp Lys Ser Ser Ser Thr Ala Tyr
 65                  70                  75                  80

Met Gln Leu Ser Ser Leu Thr Ser Asp Ser Ala Val Tyr Phe Cys
                 85                  90                  95

Ala Ala Ile Asp Tyr Ser Gly Pro Tyr Ala Val Asp Asp Trp Gly Gln
                100                 105                 110

Gly Thr Ser Val Thr Val Ser Ser
            115                 120

<210> SEQ ID NO 62
<211> LENGTH: 121
<212> TYPE: PRT
<213> ORGANISM: Homo sapiens

<400> SEQUENCE: 62

Gln Val Gln Leu Gln Gln Ser Gly Ala Glu Leu Val Arg Pro Gly Thr
  1               5                  10                  15

Ser Val Lys Val Ser Cys Lys Ala Ser Gly Tyr Asp Phe Asn Asn Asp
                 20                  25                  30

Leu Ile Glu Trp Val Lys Gln Arg Pro Gly Gln Gly Leu Glu Trp Ile
             35                  40                  45

Ala Val Ile Asn Pro Gly Ser Gly Arg Thr Asn Tyr Asn Glu Lys Phe
         50                  55                  60

Lys Gly Lys Ala Thr Leu Thr Ala Asp Lys Ser Ser Ser Thr Val Tyr
 65                  70                  75                  80

Met Gln Leu Ser Ser Leu Thr Ser Asp Ser Ala Val Tyr Phe Cys
                 85                  90                  95

Ala Met Ile Tyr Tyr Gly Pro His Ser Tyr Ala Met Asp Tyr Trp Gly
                100                 105                 110

Gln Gly Thr Ser Val Thr Val Ser Ser
            115                 120

<210> SEQ ID NO 63
<211> LENGTH: 107
<212> TYPE: PRT
<213> ORGANISM: Homo sapiens

<400> SEQUENCE: 63

Asp Ile Val Met Thr Gln Ser His Lys Phe Met Ser Thr Val Val Gly
  1               5                  10                  15

Asp Arg Val Ser Ile Thr Cys Lys Ala Ser Leu Asp Val Arg Thr Ala
                 20                  25                  30

Val Ala Trp Tyr Gln Gln Lys Pro Gly Gln Ser Pro Lys Leu Leu Ile
             35                  40                  45

Tyr Ser Ala Ser Tyr Arg Tyr Thr Gly Val Pro Asp Arg Phe Thr Gly
         50                  55                  60

Ser Gly Ser Gly Thr Asp Phe Thr Phe Asn Ile Arg Ser Val Gln Ala
 65                  70                  75                  80

Glu Asp Leu Ala Val Tyr Tyr Cys Gln Gln His Tyr Gly Ile Pro Trp
                 85                  90                  95

Thr Phe Gly Gly Gly Thr Lys Leu Glu Ile Lys
                100                 105

<210> SEQ ID NO 64
<211> LENGTH: 107
<212> TYPE: PRT
<213> ORGANISM: Homo sapiens
```

```
<400> SEQUENCE: 64

Asp Ile Val Met Thr Gln Ser His Lys Phe Met Ser Thr Ser Val Gly
 1               5                  10                  15

Asp Arg Val Ser Val Thr Cys Lys Ala Ser Gln Ala Val Asn Thr Ala
             20                  25                  30

Val Ala Trp Tyr Gln Gln Lys Pro Gly Gln Ser Pro Lys Leu Leu Ile
         35                  40                  45

Tyr Ser Ala Ser Tyr Gly Tyr Thr Gly Val Pro Asp Arg Phe Thr Gly
     50                  55                  60

Ser Gly Ser Gly Thr Asp Phe Thr Leu Thr Ile Ser Ser Val Gln Ala
 65                  70                  75                  80

Glu Asp Leu Ala Val Tyr Tyr Cys Gln His His Tyr Gly Val Pro Trp
                 85                  90                  95

Thr Phe Gly Gly Gly Thr Lys Leu Glu Ile Lys
                100                 105
```